(12) United States Patent
Blackburn et al.

(10) Patent No.: US 9,248,133 B2
(45) Date of Patent: Feb. 2, 2016

(54) SALTS OF LORCASERIN WITH OPTICALLY ACTIVE ACIDS

(75) Inventors: Anthony C. Blackburn, San Diego, CA (US); William Lucas Betts, III, San Diego, CA (US); Jaimie Karyn Rueter, San Diego, CA (US); Yun Shan, San Diego, CA (US); Anna Shifrina, San Diego, CA (US); Scott Stirn, San Diego, CA (US)

(73) Assignee: Arena Pharmaceuticals, Inc., San Diego, CA (US)

( * ) Notice: Subject to any disclaimer, the term of this patent is extended or adjusted under 35 U.S.C. 154(b) by 121 days.

(21) Appl. No.: 13/820,126

(22) PCT Filed: Aug. 31, 2011

(86) PCT No.: PCT/US2011/049935
§ 371 (c)(1),
(2), (4) Date: Aug. 8, 2013

(87) PCT Pub. No.: WO2012/030938
PCT Pub. Date: Mar. 8, 2012

(65) Prior Publication Data
US 2013/0310369 A1    Nov. 21, 2013

Related U.S. Application Data

(60) Provisional application No. 61/402,580, filed on Sep. 1, 2010.

(51) Int. Cl.
*A61K 31/55* (2006.01)
*C07D 223/16* (2006.01)
*A61K 31/155* (2006.01)

(52) U.S. Cl.
CPC .............. *A61K 31/55* (2013.01); *A61K 31/155* (2013.01); *C07D 223/16* (2013.01)

(58) Field of Classification Search
CPC .............................. A61K 31/55; C07D 223/16
USPC ...................................... 514/217.01; 540/594
See application file for complete search history.

(56) References Cited

U.S. PATENT DOCUMENTS

| | | |
|---|---|---|
| 2,900,415 A | 8/1959 | Biel |
| 3,652,543 A | 3/1972 | Hoegerle |
| 3,716,639 A | 2/1973 | Hoegerle et al. |
| 3,795,683 A | 3/1974 | Brossi et al. |
| 4,108,989 A | 8/1978 | Holden |
| 4,111,957 A | 9/1978 | Holden et al. |
| 4,210,729 A | 7/1980 | Hermans et al. |
| 4,210,749 A | 7/1980 | Shetty |
| 4,233,217 A | 11/1980 | Shetty |
| 4,477,378 A | 10/1984 | Gold et al. |
| 4,541,954 A | 9/1985 | Borowski et al. |
| 4,584,293 A | 4/1986 | Reiffen et al. |
| 4,737,495 A | 4/1988 | Bomhard et al. |
| 4,762,845 A | 8/1988 | Chu et al. |
| 4,957,914 A | 9/1990 | Clark et al. |
| 4,988,690 A | 1/1991 | Effland et al. |
| 5,015,639 A | 5/1991 | Berger et al. |
| 5,178,786 A | 1/1993 | Jahnke et al. |
| 5,247,080 A | 9/1993 | Berger et al. |
| 5,275,915 A | 1/1994 | Kojima et al. |
| 5,387,685 A | 2/1995 | Powell et al. |
| 5,397,793 A | 3/1995 | Shaber et al. |
| 5,412,119 A | 5/1995 | Brussee et al. |
| 5,422,355 A | 6/1995 | White et al. |
| 5,691,362 A | 11/1997 | McCormick et al. |
| 5,750,520 A | 5/1998 | Danilewicz et al. |
| 5,795,895 A | 8/1998 | Anchors |
| 5,856,503 A | 1/1999 | Aebi et al. |
| 5,861,393 A | 1/1999 | Danilewicz et al. |
| 5,908,830 A | 6/1999 | Smith et al. |
| 5,925,651 A | 7/1999 | Hutchinson |
| 5,939,415 A | 8/1999 | Laufer et al. |
| 5,942,535 A | 8/1999 | Laufer et al. |
| 5,958,943 A | 9/1999 | Laufer et al. |
| 6,087,346 A | 7/2000 | Glennon et al. |
| 6,218,385 B1 | 4/2001 | Adam et al. |
| 6,900,313 B2 | 5/2005 | Wasserscheid et al. |
| 6,953,787 B2 | 10/2005 | Smith et al. |
| 6,972,295 B2 | 12/2005 | Hagmann et al. |
| 7,105,523 B2 | 9/2006 | Stasch et al. |
| 7,157,466 B2 | 1/2007 | McClure et al. |
| 7,173,037 B2 | 2/2007 | Alonso-Alija et al. |
| 7,211,591 B2 | 5/2007 | Tajima et al. |

(Continued)

FOREIGN PATENT DOCUMENTS

| | | |
|---|---|---|
| AU | 515 236 B2 | 3/1981 |
| CA | 1090797 | 12/1980 |
| CA | 2197789 | 2/1996 |
| CA | 2325741 | 10/1999 |
| CH | 500194 | 1/1971 |
| CN | 102126988 | 7/2011 |
| DE | 1914456 | 6/1971 |
| DE | 1944121 | 11/1983 |
| DE | 3315106 A1 | 11/1983 |
| DE | 3418270 A1 | 11/1985 |

(Continued)

OTHER PUBLICATIONS

U.S. Appl. No. 60/372,058, filed Apr. 12, 2002, Smith et al.
U.S. Appl. No. 60/405,495, filed Aug. 23, 2002, Smith et al.
U.S. Appl. No. 60/434,607, filed Dec. 18, 2002, Smith et al.
U.S. Appl. No. 60/479,280, filed Jun. 17, 2003, Smith et al.
U.S. Appl. No. 60/512,967, filed Oct. 21, 2003, Burbaum et al.
U.S. Appl. No. 60/638,221, filed Dec. 21, 2004, Agarwal et al.
U.S. Appl. No. 60/789,191, filed Apr. 3, 2006, Lu et al.
U.S. Appl. No. 60/873,036, filed Dec. 5, 2006, Gharbaoui et al.
U.S. Appl. No. 61/068,102, filed Mar. 4, 2008, Carlos et al.
U.S. Appl. No. 61/268,930, filed Jun. 18, 2009, Demattei et al.

(Continued)

*Primary Examiner* — Brenda Coleman

(57) ABSTRACT

Salts of 8-chloro-1-methyl-2,3,4,5-tetrahydro-1H-3-benzazepine with optically active acids, and pharmaceutical compositions comprising them that are useful for, inter alia, weight management.

24 Claims, 24 Drawing Sheets

(56) References Cited

U.S. PATENT DOCUMENTS

| | | |
|---|---|---|
| 7,229,991 B2 | 6/2007 | Merla et al. |
| 7,230,024 B2 | 6/2007 | Carpino et al. |
| 7,232,823 B2 | 6/2007 | Carpino et al. |
| 7,514,422 B2 | 4/2009 | Smith et al. |
| 7,704,993 B2 | 4/2010 | Smith et al. |
| 7,977,329 B2 | 7/2011 | Smith et al. |
| 8,153,621 B2 | 4/2012 | Behan et al. |
| 8,168,624 B2 | 5/2012 | Agarwal et al. |
| 8,168,782 B2 | 5/2012 | Weigl et al. |
| 8,207,158 B2 | 6/2012 | Smith et al. |
| 8,273,734 B1 | 9/2012 | Smith et al. |
| 8,299,241 B2 | 10/2012 | Gharbaoui et al. |
| 2003/0105106 A1 | 6/2003 | Chiang et al. |
| 2003/0225057 A1 | 12/2003 | Smith et al. |
| 2004/0101575 A1 | 5/2004 | Hinz |
| 2005/0020573 A1 | 1/2005 | Smith et al. |
| 2007/0060568 A1 | 3/2007 | Smith et al. |
| 2007/0275949 A1 | 11/2007 | Smith et al. |
| 2008/0009478 A1 | 1/2008 | Smith et al. |
| 2008/0045502 A1 | 2/2008 | Wolgast et al. |
| 2009/0143576 A1 | 6/2009 | Weigl et al. |
| 2010/0004223 A1 | 1/2010 | Agarwal et al. |
| 2010/0173894 A1 | 7/2010 | Brian et al. |
| 2010/0305316 A1 | 12/2010 | Gharbaoui et al. |
| 2011/0015438 A1 | 1/2011 | Carlos et al. |
| 2012/0135982 A1 | 5/2012 | Smith et al. |
| 2012/0142967 A1 | 6/2012 | De Mattei et al. |
| 2012/0252786 A1 | 10/2012 | Behan et al. |
| 2012/0252787 A1 | 10/2012 | Anderson et al. |
| 2012/0252788 A1 | 10/2012 | Smith et al. |
| 2012/0264743 A1 | 10/2012 | Agarwal et al. |

FOREIGN PATENT DOCUMENTS

| | | |
|---|---|---|
| EP | 0 002 765 A1 | 7/1979 |
| EP | 0 027 695 B1 | 10/1980 |
| EP | 0 007 070 A1 | 1/1983 |
| EP | 0 161 350 A1 | 11/1985 |
| EP | 0 174 118 A3 | 3/1986 |
| EP | 0 080 779 B1 | 7/1986 |
| EP | 0 204 349 A2 | 12/1986 |
| EP | 0 096 838 A1 | 4/1987 |
| EP | 0 245 997 A2 | 11/1987 |
| EP | 0 285 287 A2 | 10/1988 |
| EP | 0 285 287 A3 | 10/1988 |
| EP | 0 331 130 A1 | 9/1989 |
| EP | 0 331 130 B1 | 9/1993 |
| EP | 0 285 919 B1 | 10/1994 |
| EP | 0 987 235 A1 | 3/2000 |
| EP | 1 074 549 A2 | 2/2001 |
| EP | 0 987 235 B1 | 3/2003 |
| EP | 1 074 549 B1 | 11/2003 |
| EP | 1 411 881 A2 | 4/2004 |
| EP | 1 411 881 B1 | 5/2005 |
| EP | 1 838 677 B1 | 9/2009 |
| FR | 2 518 544 A1 | 6/1983 |
| GB | 1196229 | 6/1970 |
| GB | 1221324 | 2/1971 |
| GB | 1225053 | 3/1971 |
| GB | 1247306 | 9/1971 |
| GB | 1268243 | 3/1972 |
| GB | 1542317 | 3/1979 |
| GB | 1599705 | 10/1981 |
| GB | 2133401 | 7/1984 |
| JP | 62-267250 | 11/1987 |
| JP | 2-502723 | 8/1990 |
| JP | 5-339263 | 12/1993 |
| JP | 6-62574 | 8/1994 |
| JP | 6-298746 | 10/1994 |
| JP | 8-134048 | 5/1996 |
| JP | 9-30960 | 2/1997 |
| JP | 9-87258 | 3/1997 |
| JP | 2000-44533 | 2/2000 |
| JP | 2001-76413 | 3/2001 |
| JP | 2001-89472 | 4/2001 |
| NL | 7807819 | 7/1978 |
| SU | 1238732 A3 | 6/1986 |
| WO | WO 88/07526 A1 | 10/1988 |
| WO | WO 88/07858 A1 | 10/1988 |
| WO | WO 91/19698 A1 | 12/1991 |
| WO | WO 93/00094 A2 | 1/1993 |
| WO | WO 93/03015 A1 | 2/1993 |
| WO | WO 93/16997 A1 | 9/1993 |
| WO | WO 95/13274 A1 | 5/1995 |
| WO | WO 96/04271 A1 | 2/1996 |
| WO | WO 96/05194 A1 | 2/1996 |
| WO | WO 96/33993 A1 | 10/1996 |
| WO | WO 97/24364 A1 | 7/1997 |
| WO | WO 98/06701 A1 | 2/1998 |
| WO | WO 98/40385 A1 | 9/1998 |
| WO | WO 99/24411 A1 | 5/1999 |
| WO | WO 02/40471 A2 | 5/2002 |
| WO | WO 02/48124 A2 | 6/2002 |
| WO | WO 02/074746 A1 | 9/2002 |
| WO | WO 03/000663 A1 | 1/2003 |
| WO | WO 03/027068 A2 | 4/2003 |
| WO | WO 03/057161 A2 | 7/2003 |
| WO | WO 03/062205 A1 | 7/2003 |
| WO | WO 03/062392 A2 | 7/2003 |
| WO | WO 03/086306 A2 | 10/2003 |
| WO | WO 03/086306 A3 | 2/2004 |
| WO | WO 2004/037788 A1 | 5/2004 |
| WO | WO 2005/003096 A1 | 1/2005 |
| WO | WO 2005/016902 A1 | 2/2005 |
| WO | WO 2005/019179 A2 | 3/2005 |
| WO | WO 2005/019179 A3 | 3/2005 |
| WO | WO 2005/019180 A1 | 3/2005 |
| WO | WO 2005/042490 A1 | 5/2005 |
| WO | WO 2005/042491 A1 | 5/2005 |
| WO | WO 2005/082859 A1 | 9/2005 |
| WO | WO 2006/006933 A2 | 1/2006 |
| WO | WO 2006/013209 A2 | 2/2006 |
| WO | WO 2006/043710 A1 | 4/2006 |
| WO | WO 2006/069363 A2 | 6/2006 |
| WO | WO 2006/071740 A2 | 7/2006 |
| WO | WO 2006/069363 A3 | 5/2007 |
| WO | WO 2007/120517 A2 | 10/2007 |
| WO | WO 2007/120517 A3 | 6/2008 |
| WO | WO 2008/070111 A2 | 6/2008 |
| WO | WO 2008/070111 A3 | 8/2008 |
| WO | WO 2008/153632 A2 | 12/2008 |
| WO | WO 2008/156707 A1 | 12/2008 |
| WO | WO 2009/080691 A2 | 7/2009 |
| WO | WO 2009/097416 A1 | 8/2009 |
| WO | WO 2009/111004 A1 | 9/2009 |
| WO | WO 2010/148207 A2 | 12/2010 |
| WO | WO 2012/030927 A2 | 3/2012 |
| WO | WO 2012/030951 A1 | 3/2012 |
| WO | WO 2012/030953 A1 | 3/2012 |
| WO | WO 2012/030957 A1 | 3/2012 |

OTHER PUBLICATIONS

"Arena Pharmaceuticals Announces Results of its Phase 1b Safety Study for its Novel Anti-Obesity Compound," Press Release, Nov. 30, 2004, 2 pages.

"Arena Pharmaceuticals Initiates Clinical Trial of Novel Anti-Obesity Drug," Press Release, Feb. 24, 2004, 1 page.

"Arena Pharmaceuticals Initiates Phase 1b Clinical Trial of Novel Anti-Obesity Drug," Press Release, Jul. 26, 2004, 1 page.

"Arena Pharmaceuticals Initiates Phase 2 Efficacy Study for its Novel Anti-Obesity Compound," Press Release, Dec. 22, 2004, 2 pages.

"Arena Pharmaceuticals Reports Successful Phase 1a Safety and Clinical Pharmacology Trial Results of Novel Anti-Obesity Compound," Press Release, Jul. 14, 2004, 2 pages.

"Silver Lining to the Cloud Over Anorexogen-Related Cardiac Valvulpathy?" Editorial, Annals of Internal Medicine, 134(4): 335-337 (2001).

Bagnol et al., "Obesity and Hypothalamic Signaling: Role of GPCRs," Presentation, Arena Pharmaceuticals, Inc., Jul. 30, 2010, 30 pages.

(56) References Cited

OTHER PUBLICATIONS

Baindur et al., "(±)-3-Allyl-7-halo-8-hydroxy-1-phenyl-2,3,4,5-tetrahydro-1H-3-benzazepines as Selective High Affinity D1 Dopamine Receptor Antagonists: Synthesis and Structure-Activity Relationship," J. Med. Chem., 35:67-72 (1992).
Barbière, "Estérification Nitrique et Nitration d'Amino-alcools," Bulletin de la Société Chimique de France, 5(11):470-480 (1944).
Barnes, "Pharmacological Strategies for Relapse Prevention in Schizophrenia," Psychiatry 3(10): 37-40 (2004).
Berge et al., "Pharmaceutical Salts," Journal of Pharmaceutical Sciences 66(1):1-19 (1977).
Bickerdike, "5-HT2C Receptor Agonists as Potential Drugs for the Treatment of Obesity," Current Topics in Medicinal Chemistry, 3:885-897 (2003).
Biel, "Bronchodilators, N-substituted Derivatives of 1-(3',4'-Dihydroxyphenyl)-2-aminoethanol (Arterenol)," J. Am. Chem. Soc. 76:3149-3153 (1954).
Binetti et al. "Behavior Disorders in Alzheimer Disease: A Transcultural Perspective.," Arch Neurol., 55:539-544 (1998).
Bosch et al., "Studies on the Synthesis of Pentacyclic Strychnos Indole Alkaloids. Photocyclization of N-Chloroacetyl-l,2,3,4,5,6-hexahydro-1,5-methanoazocino [4,3-b] Indole Derivatives," Tetrahedron, 41(12):2557-66 (1985).
Bos et al., "Novel Agonists of 5HT2C receptors. Synthesis & biological evaluation of Substituted 2-{Indol-1-yl)-1-methylethylamines and 2-(Indeno[1,2-b]pyrrol-1-yl)-1-methylethylamines," Improved Therapeutics for Obsessive Compulsive Disorder, J. Med. Chem. 40(17):2762-2769 (1997).
Bremner "Seven Membered Rings," Institute for Biomolecular Science, Dept. of Chemistry, University of Wollongong; "Progress in Heterocyclic Chemistry 13," Pergamon Press, Ch. 7:340-77 (2001).
Byrn et al., "Pharmaceutical solids: A strategic approach to regulatory consideration," Pharmaceutical Research 12(7):945-954 (1995).
Caira, "Crystalline polymorphism of organic compounds," Topics in Current Chemistry 198(2): 163-208 (1998).
Callahan et al., "Fluoxetine Increases the Anorectic and Long-Term Dopamine-Depleting Effects of Phentermine," Synapse, 38(4):471-6 (2000).
Carey, F and Sunderg, R., "Advanced Organic Chemistry, Part B: Reactions and Synthesis, second edition" 1983, Plenum Press, New York, pp. 96-98.
CAS Registry No. 006640-24-01 (2007).
CAS Registry No. 27487-50-9 (1984).
CAS Registry No. 27487-51-0 (1984).
CAS Registry No. 46906-45-0 (1984).
CAS Registry No. 149454-12-6 (1993).
CAS Registry No. 400878-20-8 (2002).
CAS Registry No. 620948-34-7 and 620948-93-8 (2007).
Casy, et al., "Some Arylalkylamino Analogs of Acyclic Analgetics," J. Med. Chem., 11(3):599-601 (1968).
Chahal et al., IDdb Meeting Report 2000, May 17-18.
Chang et al., "Dopamine Receptor Binding Properties of Some 2,3,4,5-tetrahydro-1H-3-benzazepine-7-ols with Non-Aromatic Substituents in the 5-Position," Bioorganic & Medicinal Chemistry Letters, 2(5):399-402 (1992).
Chemical abstract (online) Accession No. 1980:407990.
Cheng. "Fen/Phen and Valvular Heart Disease: The Final Link Has Now Been Established," Circulation 2000;102;e180.
Chumpradit et al., "(±)-7-Chloro-8-hydroxyl-1-(4'-[125I]iodophenyl)-3-methyl-2,3,4,5-tetrahydro-1H-3-benzazepine: A Potential CNS D-1 Dopamine Receptor Imaging Agent," J. Med. Chem., 32:1431-35 (1989).
Clark et al., "1,9-Alkano-bridged 2,3,4,5-tetrahydro-1H-3-benzazepines with Affinity for the α2-Adrenoceptor and the 5-HT1A Receptor," J. Med. Chem., 33:633-41 (1990).
Clinical Trial NCT00768612. "Study Evaluating Safety and Tolerability of Vabicaserin in Patients With Sudden Worsening of Schizophrenia Study," (2008).
Connolly et al., "Selections from Current Literature: Pharmacological Treatment of Obesity," Family Practice, 15(1):88-93 (1998).
Deady et al., "Synthesis of Some Tetrahydro-2- and 3-benzazepines, and of Hexahydro-3-benzazocine," JCS Perkin I, 782-3 (1973).
Demarinis et al., "Development of an Affinity Ligand for Purification of α2-Adrenoceptors from Human Platelet Membranes," J. Med. Chem., 27:918-921 (1984).
Dhonnchadha et al., "Anxiolytic-Like Effects of 5-HT2 Ligands on Three Mouse Models of Anxiety," Behav. Brain Res. 140:203-214 (2003).
Diagnostic and Statistical Manual of Mental Disorders, 4th edition, Text Revision, Washington, DC, American Psychiatric Association, 2000.
Di Chiara et al., "Nucleus Accumbens Shell and Core Dopamine: Differential Role in Behavior and Addiction," Behavioural Brain Research, 137: 75-114 (2002).
Di Chiara et al., "Reward System and Addiction: What Dopamine Does and Doesn't Do," Current Opinion in Pharmacology 7:69-76 (2007).
Di Giovanni et al., "Serotonin/Dopamine Interaction—Focus on 5-HT2C Receptor, a New Target of Psychotropic Drugs," Indian Journal of Experimental Biology, 40:1344-1352 (2002).
Di Matteo et al., "Role of 5-HT2C Receptors in the Control of Central Dopamine Function," Trends in Pharmacological Sciences, 22(5):229-232 (2001).
Dixit et al. "Agents Acting on Central Nervous System: Part XXIII-2-Substituted 1, 2, 3, 4, 6, 7, 12, 12a-Octahydropyrazino[2,1-b][3] benzazepines & 3-Substituted 1, 2, 3, 4, 4a, 5, 6, 11-Octahydropyrazino[l,2-b][2] benzazepines," CDRI Communication No. 1969, 893-97 (1974).
Draper et al., "Novel Stereoselective Syntheses of the Fused Benzazepine Dopamine D1 Antagonist (6aS, 13bR)-11-chloro-6, 6a,7,8,9, 13b-hexahydro-7-methyl-5H-benzo[d]naphth[2, 1-b]azepin-12-ol (Sch 39166): 1. Aziridinium Salt Based Syntheses," Organic Process Research & Development, 2(3):175-85 (1998).
Flannery-Schroeder, "Reducing Anxiety to Prevent Depression," Am. J. Prev. Med. 31(6S1):S136-S142 (2006).
Frankel et al., "Brain Serotonin Transporterdistribution in Subjects With Impulsive Aggressivity: A Positron Emission Study With [11C]McN 5652." Am. J. Psychiatry,162:915-923 (2005).
Fuchs et al., "Total Synthesis of (+/−)-Lennoxamine and (+/−)-Aphanorphine by Intramolecular Electrophilic Aromatic Substitution Reactions of 2-Amidoacroleins," Organic Letters, 3(24):3923-3925 (2001).
Gallant et al., "U-22,394A: A Controlled Evaluation in Chronic Schizophrenic Patients," Current Therapy Research, 9(11):579-81(1967).
Gardent et al., "Sur Quelques Proprietes De L'amino-2-Bromo-4 1H Benzazepine-3 Et De Ses Derives," Bulletin de la Societe Chimique de France, 2:600-5 (1968).
Garrison, "Defining Obesity: An Adventure in Cardiovascular Disease Epidemiology," J. Nutritional Biochem. 9(9):493-500 (1998).
Gerace et al., "Predictors of Weight Increases over 7 Years in Fire Fighters and Paramedics," Preventive Medicine 25:593-600 (1996).
Gerritz et al., "Two General Routes to 1,4-Disubstituted-2,3,4,5-tetrahydro-1H-3-benzazepines," Organic Letters, 2(25):4099-102 (2000).
Gobert et al., "Serotonin$_{2c}$ Receptors Tonically Suppress the Activity of Mesocortical Dopaminergic and Adrenergic, But Not Serotonergic, Pathways: A Combined Dialysis and Electrophysiological Analysis in the Rat," Synapse 36: 205-221 (2000).
Gombar et al., "Pharmacokinetics of a Series of 6-Chloro-2, 3, 4, 5-Tetrahydro-3-Substituted-1H-3-Benzazepines in Rats," Drug Metab. Disposition ,16:367-372 (1988).
Greene, "Protective Groups in Organic Synthesis," 3rd Ed., Wiley and Sons (1999).
Greene et al., Protective Groups in Organic Syntheses, 2nd Ed., Wiley and Sons, NY (1991).
Griesser "Polymorphism in the Pharmaceutical Industry," ed. Rolf Hilfier, Wiley-VCH Verlag GmbH & Co.: pp. 211-233 (2006).
Guillory, "Polymorphism in Pharmaceutical Solids," ed. Harry G. Brittain, Marcel Dekker, Inc., vol. 95: pp. 202-209 (1999).
Halford et al., "Serotonergic Drugs: Effects on Appetite Expression and Use for the Treatment of Obesity," Drugs 67(1):27-55 (2007).

(56) References Cited

OTHER PUBLICATIONS

Halford et al., "o-Phenylenediacetimide and Other Compounds Related to 3,1 H-benzazepine," J. Org. Chem., 17:1646-52 (1952).
Halford, "Obesity Drugs in Clinical Development," Current Opinion in Investigational Drugs 7(4):312-318 (2006).
Hasan et al., "Syntheses of N-Chloroacyl-β-phenylethylamine Derivatives," Indian J. Chem., 9:1022-4 (1971).
Hashima et al., "Syntheses and Biological Activities of the Marine Bryozoan Alkaloids Convolutamines A, C and F and Lutamides A and C," Bioorg & Med. Chem., 8:1757 (2000).
Hassine-Coniac, et al., "Preparation Et Propriétés D'aldéhydes Dans La Série De La Benzazépine-3," Bulletin de La Société Chimique de France, 11:3985-92 (1971) French Lang Only.
Haynes et al., "Occurrence of Pharmaceutically Acceptable Anions and Cations in the Cambridge Structural Database," J. Pharm. Sci. 94(10):2111-2120 (2005).
Hazebroucq, "Accès a Des I-H, Tètrahydro-2, 3, 4,5 Benzazèpines-3 One-I, et a Des Hexahydro Imidazo Isoquinoléines," Ann. Chim., t.1:221-54 (1966) French Lang Only.
Heisler et al., "Activation of Central Melanocortin Pathways by Fenfluramine," Science, 297:609-611 (2002).
Helferich et al., "Uber Derivate Einger Chinolincarbonsauren," J. Fur Praktische Chemie, 33:39-48 (1966).
Hester et al., "Azepinoindoles. I. Hexahydroazepino[4,5-b]indoles," J. Med. Chem., 11(1): 101-106 (1968).
Heys et al., "A New Entry into C7-Oxygenated Tetrahydro-1H-3-benzazepines: Efficient Labeling with Carbon-14 in the Benzo Ring," J. Org. Chem., 54(19):4702-6 (1989).
Higgins et al. "Serotonin and Drug Reward: Focus on 5-HT2C Receptors," European Journal of Pharmacology, 480: 151-162 (2003).
Hitzig, "Combined Serotonin and Dopamine Indirect Agonists Correct Alcohol Craving and Alcohol-Associated Neuroses," Journal of Substance Abuse Treatment, 11(5):489-90 (1994).
Ichii, "Friedel-Crafts Aralkylation. II. The AlCl3 CH2NO2-Catalyzed Phenethylation of Benzene and Toluene With 2-Arylethyl Chlorides in a Nitromethane Solution," Bulletin of the Chemical Society of Japan, 45(9):2810-2813 (1972).
Im et al., "Positive Allosteric Modulator of the Human 5-HT2C Receptor," Molecular Pharmacology, 64: 78-84 (2003).
Isaac, "The 5-HT2C Receptor as a Potential Therapeutic Target for the Design of Antiobesity and Antiepileptic Drugs," Drugs of the Future 26(4), 383-393 (2001).
Jandacek, "APD-356 (Arena)," Current Opinion in Investigational Drugs 6(10):1051-1055 (2005).
Jenck, et al., "Antiaversive Effects of 5HT2C Receptor Agonists and Fluoxetine in a Model of Panic-Like Anxiety in Rats," European Neuropsychopharmacology 8: 161 (1998).
Jensen et al., "Potential Role of New Therapies in Modifying Cardiovascular Risk in Overweight Patients with Metabolic Risk Facts," Obesity 14 (Suppl. 3):143S-149S (2006).
Kaiser et al., "6-(Phenylthio)-substituted 2,3,4,5-tetrahydro-1H-3-benzazepines, a Novel Class of Dopamine Receptor Antagonists and Neuroleptics," J. Med. Chem., 23(9):975-6 (1980).
Karasu et al., Practice Guideline for the Treatment of Patients with Major Depressive Disorder (2000).
Klein, "Outcome Success in Obesity," Obesity Res., 9(suppl. 4):354S-358S (2001).
Klohr et al., "An Intramolecular Photocyclization to Form the Azepino[3,4,5-cd]Indole System," Synthetic Communications 18(7):671-4 (1988).
Koplan et al., "Preventing Childhood Obesity: Health in the Balance, Executive Summary," The National Academies Press, Washington, D.C., 436 pages (excerpt includes pp. 1-19, v-xix) (2005).
Krull et al., "Synthesis and Structure/NMDA Receptor Affinity Relationships of 1-Substituted Tetrahydro-3-Benzazepines,"Bioorganic & Medicinal Chem. 12(6):1439-1451 (2004).
Kuenburg et al., "Development of a Pilot Scale Process for the Anti-Alzheimer Drug (−−)-Galanthamine Using Large-Scale Phenolic Oxidative Coupling and Crystallisation-Induced Chiral Conversion," Organic Process Research & Development, 3(6):425-31 (1999).
Lacivita et al., "Selective Agents for Serotonin2C (5-HTC2C) Receptor," Current Topics in Medicinal Chemistry, 6: 1927-1970 (2006).
Ladd et al., "Synthesis of a Dopaminergic Binding of 2-Aryldopamine Analogues: Phenethylamines, 3-Benzazepines, and 9-(Aminomethyl) Fluorenes," J. Med. Chem., 29(10):1904-12 (1986).
Lam et al., Canadian Consensus Guidelines for the Treatment of Seasonal Affective Disorder, Clinical & Academic Publishing, Vancouver, BC, Canada (1999).
Lanteri et al., "Drugs of abuse specifically sensitive noradrenergic and serotonergic neurons via a non-dopaminergic mechanism," Neuropsychopharmacology 33(7):1724-1734 (2008).
Lennon et al., "Azabenzocycloheptenones. Part XVIII. Amines and Amino-ketones of the Tetrahydro-3-benzazepin-1-one Series," J.C. S. Perkin I, 7:622-6 (1975).
Lin et al, "Benzindene Prostaglandins. Synthesis of Optically Pure 15-Deoxy-U-68,215 and its Enantiomer via a Modified Intramolecular Wadsworth-Emmons-Wittig Reaction," J. Org. Chem., 52(25):5594-601 (1987).
Loke et al., "Appetite Suppressants and Valvular Heart Disease—A Systematic Review," BMC Clinical Pharmacology, 2(6):1-10 (2002).
MacDonald et al., "Design and Synthesis of trans-3-(2-(4-((3-(3-(5-methyl-1,2,4-oxadiazolyl))-phenyl)carboxamido)cyclohexyl)ethyl)-7-methylsulfonyl-2,3,4,5-tetrahydro-1H-3-benzazepine (SB-414796): A Potent and Selective Dopamine D3 Receptor Antagonist," J. Med. Chem., 46(23):4952-64 (2003).
March, "Advanced Organic Chemistry, Reactions, Mechanisms and Structure; Third edition," 1985, John Wiley &Sons (Wiley-Interscience Publication), New-York, pp. 382-384.
Martin et al.,"5HT2C Receptor Agonists Pharmacological Characteristics and Therapeutic Potential," J. Pharmacol. Exp. Therap., 286(2):913-924 (1998).
Millan et al., "5HT2C Receptors Mediate Penile Erections in Rats: Actions of Novel and Selective Agonists and Antagonists." Eur. J. Pharmacol., 325:9-12 (1997).
Millan et al., "Serotonin (5-HT)2C receptors tonically inhibit dopamine (DA) and noradrenaline (NA), but not 5-HT, release in the frontal cortex in vivo," Neuropharmalogy 37(7):953-955 (1998).
Moline et al., "Postpartum Depression: A Guide for Patients and Families," Expert Consensus Guidelines Series—Treatment of Depression in Woman,112-113 (2001).
Mondeshka et al., "Racemische und optisch active 2-Chlorethylcarbamoyl-Derivate des 7,8-Dimethoxy-1-phenyl-1H-3-benzazepins: Neue Strukturtypen von DA, NE und 5-HT Uptake Inhibitoren," Arch. Pharm., 323:829-832 (1990).
Morisette et al., "High-throughput crystallization: polymorphs, salts, co-crystals and solcates of pharmaceutical solids," Advanced Drug Delivery Reviews 56(3):275-300 (2004).
Muller et al., "Intracellular 5-HT2C-Receptor Dephosphorylation: A New Target for Treating Drug Addiction," Trends in Pharmacological Sciences, 27(9):455-58 (2006).
Nagase et al., "An Anhydrous Polymorphic Form of Trehalose," Carbohydrate Research 337(2):167-173 (2002).
Nagle et al., "Efficient Synthesis of β-amino Bromides," Tetrahedron Letters, 41:3011-4 (2000).
Nair et al., "Preparation of 2,3,4,5-Tetrahydro-3,1H-benzazepine-2-one," Indian J. Chem., 5:169-70 (1967).
National Institute on Drug Abuse, Proc. 41st Ann. Scientific Mtg. 356-401 (1979).
Navarro-Vazquez et al., "A Study of Aryl Radical Cyclization in Enaminone Esters," J. Org. Chem., 67:3213-20 (2002).
Neumeyer et al., "Development of a High Affinty and Stereoselective Photaffinty Label for the D-1 Dopamine Receptor: Synthesis and Resolution of 7-]125I]Iodo-8-hydroxy-3-methyl-1-4'-azidophenyl)-2,3,4,5-tetrahydro-1H-3-benzazepine," J. Med. Chem., 33(2);521-6 (1990).

(56) References Cited

OTHER PUBLICATIONS

Niendam et al., "Neurocognitive Performance and Functional Disability in the Psychosis Prodrome," Schizophrenia Research, 84:100-111 (2006).
Ohnmacht et al., "Naphtho[2,1-b][1,5]-and [1,2-f][1,4]oxazocines as Selective NK1 Antagonists," Biorganic & Medicinal Chem. 12(10):2653-2666 (2004).
Okuno et al., "Photocyclization of N-chloroacetyl-2,5-dimethoxyphenethylamine. Synthesis of Pyrroloindoles," Chem. Pharm. Bull., 23(11):2584-90 (1975).
Orito et al., "Benzolactams-1: Alkylation of 1,2,4,5-Tetrahydro-3-Methyl-3H-3-Benzazepin-2-One With Sodium Hydride and Alkyl Halide," Tetrahedron 36:1017-1021 (1980).
Orito et al., "Total Synthesis of Pseudo Type of Protopine Alkaloids," Heterocycles, 14(1)11-14 (1980).
Orito, et al., "Synthetic Studies of Heterocyclic Compounds I, Alkylation and Acylation of 1,2,4,5-Tetrahydro-3-Methyl-3H-3-Benzazepin-2-one," CASREACT, 93:7990 (1979).
Paulekuhn et al., "Trends in Active Pharmaceutical Ingredient Salt Selection Based on Analysis of the Orange Book Database." J. Med. Chem., 50(26):6665-6672 (2007).
Pauvert et al., "Silver Nitrate-Promoted Ring Enlargement of 1-tribromomethyl-1,2-dihydro- and 1-tribromethyl-1,2, 3,4-tetrahydro-isoquinoline Derivatives: Application to the Synthesis of the Anti-anginal Zatebradine," Tetrahedron Letters, 44:4203-6 (2003).
Pawan et al., "Preliminary Study on the Effects of Fenfluramine Derivative, 'S992' in Man," British Journal of Pharmacology, 41(2): 416P-417P (1971).
Pecherer et al., "The Synthesis of Some 7- and 7,8-Substituted 2,3,4,5-tetrahydro-1H-3-benzazepines," J. Het. Chem., 8(5):779-783 (1971).
Pecherer et al., "A Novel Synthesis of Aromatic Methoxy and Methylenedioxy Substituted 2,3,4,5-tetrahydro-1H-3-benzazepines," J. Het. Chem., 9:609-16 (1972).
Perry et al., "Prospective Study of Risk Factors for Development on Non-Insulin Dependent Diabetes in Middle Aged British Men," BMJ, 310:560-564 (1995).
Pfeiffer et al., "Dopaminergic Activity of Substituted 6-Chloro-1-phenyl-2,3,4,5-tetrahydro-1H-3-benzazepines," J. Med. Chem., 25(4):352-8 (1982).
Piesla et al., "Atypical Antipsychotic-Like Effects of 5-HT2C Agonists," Schizophrenia Research 49:95 (2001).
Porras, et al., "5-HT2A and 5-HT2C/2B Receptor Subtypes Modulate Dopamine Release Induced in Vivo by Amphetamine and Morphine in Both the Rat Nucleus Accumbens and Striatum," Neuropsychopharmacology 26: 311-324 (2002).
Remington's Pharmaceutical Sciences 17th ed., Mack Publishing Company, Easton Pa.: xv-xvi, 1409-1423 (1985).
Rosenzweig-Lipson et al., "Vabicaserin: Effects of a Novel 5HT2C Agaonist on Medial Prefrontal Cortex Neurotransmission, Cognition and Sensorimotor Gating," 29th ECNP Congress, Vienna, Austria (2007).
Roth et al., "Anorectic Efficacy of the Fenfluramine/Phentermine Combination in Rats: Additivity or Synergy?" Eur. J. Pharmacol., 373(2-3):127-34 (1999).
Rothman, "Treatment of Alcohol and Cocaine Addiction by the Combination of Pemoline and Fenfluramine: A Preliminary Case Series," Journal of Substance Abuse Treatment, 12(6):449-53 (1995).
Rothman, et al., "Evidence of Possible Involvement of 5-HT2B Receptors in the Cardiac Valvulopathy Associated with Fenfluramine and Other Serotonergic Medications," Circulation, 2836-41 (2000).
Rowland et al., "Acute Anorectic Effect of Single and Combined Drugs in Mice Using a Non-deprivation Protocol," Psychopharmacology (Berl), 157(2):193-6 (2001).
Rowland et al., "Anorectic Effect of Dehydroepiandrosterone Combined with Dexfenfluramine or Thionisoxetine," Eur. J. Pharmacol., 419(1):61-4 (2001).

Rowland et al., "Comparison of Either Norepinephrine-uptake Inhibitors or Phentermine Combined with Serotonergic Agents on Food Intake in Rats," Psychopharmacology (Berl), 149(1):77-83 (2000).
Rowland et al., "Effects of the Cannabinoid Receptor Antagonist SR 141716, Alone and in Combination with Dexfenfluramine or Naloxone, on Food Intake in Rats," Psychopharmacology (Berl), 159(1):111-6 (2001).
Schaffner et al., "Preventing Severe Mental Illnesses—New Prospects and Ethical Challenges," Schizophrenia Research, 51:3-15 (2001).
Schlademan et al., "Synthesis of Oxo- and 1-Hydroxy-azobenzocycloalkanes," J. Chem. Soc. Perkin Trans., 2:213-215 (1972).
Serajuddin et al., "Salt formation to improve drug solubility," Advanced Drug Delivery Reviews 59(7):603-616 (2007).
Silverstone, "Appetite Suppressants: a Review." Drugs. 43:6, (1992). Abstract.
Smith et al., "Discovery and SAR of New Benzazepines as Potent and Selective 5HT2c Receptor Agonists for the Treatment of Obesity," Bioorganic & Medicinal Chemistry Letters, 15(5)1467-1470 (2005).
Smith, "5-HT2C Receptor Agonists for the Treatment of Obesity," Presentation, Arena Pharmaceuticals, Inc., Jul. 28, 2010, 30 pages.
Smith, "Discovery of Lorcaserin (APD356): A Selective 5HT2C Agonist for the Treatment of Obesity," Presentation, Arena Pharmaceuticals, Inc., (2006).
Smith, et al., "Discovery and Structure—Activity Relationship of (1R)-8-Chloro-2,3,4,5-tetrahydro-1-methyl-1H-3-benzazepine (Lorcaserin), a Selective Serotonin 5-HT2c Receptor Agonist for the Treatment of Obesity," J. Med. Chem. 51:305-313 (2008).
Sussman et al., "Effects of Nefazodone on Body Weight: A Pooled Analysis of Selective Serotonin Reuptake Inhibitor- and Imipramine-Controlled Trails," J. Clin. Psychiatry, 62:4:256-60 (2001).
Tecott et al., "Eating Disorder and Epilepsy in Mice Lacking 5-HT2C Serotonin Receptors." Nature, 374:542-546 (1996).
Tietze et al., "Efficient Synthesis of 2, 3, 4, 5-Tetrahydro-1H-3-Benzazepines by Intramolecular Heck Reaction," Synthesis, 876-880 (1993).
Tohda et al., "Molecular Pathopharmacology of 5-HT2C Receptors and the RNA Editing in the Brain." J. Pharma. Science, 100: 427-432 (2006).
Tsuang et al., "Towards the Prevention of Schizophrenia," Biol. Psychiatry, 48:349-356 (2000).
Van Oekelen et al., "5-HT2A and 5-HT2C Receptors and Their Atypical Regulation Properties," Life Sciences, 72:2429-2449 (2003).
Vanderlaan et al., "Synthesis and Oxidative Coupling of (±)-3-Sxoreticuline," J. Org. Chem., 50(6):743-7 (1985).
Vink et al., "Risk Factors for Anxiety and Depression in the Elderly: A Review," J. Affect. Disord., 106:29-44 (2008).
Webb, "APD356, A Potential New Treatment for Obesity," Presentation, Arena Pharmaceuticals, Inc., Aug. 11, 2005, 43 pages.
Weinstock et al., "Separation of Potent Central and Renal Dopamine Agonist Activity in Substituted 6-Chloro-2,3,4,5-tetrahydro-7,8-dihydroxy-1-phenyl-1H-3-benzazepines," J. Med. Chem., 23(9):973-5 (1980).
Wellman et al., "Synergistic Interactions Between Fenfluramine and Phentermine," Int. J. Obes., 23(7):723-32 (1999).
Wilk, "Exchange Type Reactions Between Oxiranes or Thiiranes and 2-Hydroxyalkyl or 2-Thioalkyl Amines and Sulfides," Pol. J. Chem. 62:895 (1988).
Williams, Chemistry Demystified, pp. 123, 126 (2003).
Winkler, "Obesity and Hemostasis" Archives of Gynecology & Obst. 261(1):25-29 (1997).
Wise, "Addiction Becomes a Brain Disease," Neuron, 26: 27-33 (2000).
Wisner et al., "Postpartum Depression," N. Engl. J. Med., 347(3):194-199 (2002).

(56) References Cited

OTHER PUBLICATIONS

Woods et al., "Annual Report: Evaluation of New Compounds for Opoid Activity," National Institute on Drug Abuse, Proceedings of the 41st Annual Scientific Meeting pp. 356-401 (1979).

Wu et al., "Amino Diol Based Asymmetric Syntheses of a Fused Benzazepine as a Selective D1 Dopamine Receptor," Organic Process Research & Development, 1(5):359-64 (1997).

Yasuda et al., "A Novel and Stereoselective Synthesis of (±)-Cephalotaxine and its Analogue," Tetrahedron Letters, 27(18):2023-6 (1986).

Yonemitsu et al., "Photolysis of N-Chloracetyl-O-methyl-L-tyrosine to an Azaazulene," J. Am. Chem. Soc.,, 89(4): 1039-40 (1967).

Yonemitsu et al., "Photocyclization of Pharmacodynamic Amines. IV. Novel Heterocycles from N-chloroacetyl-3,4-dimethoxyphenethylamine," J. Am. Chem. Soc., 92(19):5686-90 (1970).

Yonemitsu et al., "Photocyclization of Pharmodynamic Amines. II. X-Ray Analysis of a Noncentrosymmetric Tetracyclic Indole," J. Am. Chem. Soc., 90(23):6522-3 (1968).

Yonemitsu et al., "Photocyclizations of Tyrosines, Tyramines, Catecholamines, and Normescaline," J. Am. Chem. Soc., 90(3):776-84 (1968).

Yoshinaga et al., "Prevention of Mildly Overweight Children from Development of More Overweight Condition," Prevention Medicine, 38:172-174 (2004).

Zhang et al., "Convolutamines A-E, Novel β-Phenylethylamine Alkaloids from Marine Bryozoan Amathia convolute," Chem. Lett., 12:2271-2274 (1994).

SALTS OF LORCASERIN WITH OPTICALLY ACTIVE ACIDS

This application is a 35 USC 371 National Stage Entry of PCT/US2011/049935 filed Aug. 31, 2011, and claims the benefit of U.S. Provisional Application No. 61/402,580 filed Sep. 1, 2010, each of which is incorporated by reference in its entirety for all purposes.

FIELD OF THE INVENTION

The present invention relates to salts of 8-chloro-1-methyl-2,3,4,5-tetrahydro-1H-3-benzazepine with optically active acids, and pharmaceutical compositions comprising them that are useful for, inter alia, weight management.

BACKGROUND OF THE INVENTION

Obesity is a life-threatening disorder in which there is an increased risk of morbidity and mortality arising from concomitant diseases such as type II diabetes, hypertension, stroke, cancer and gallbladder disease.

Obesity is now a major healthcare issue in the Western World and increasingly in some third world countries. The increase in numbers of obese people is due largely to the increasing preference for high fat content foods but also the decrease in activity in most people's lives. Currently about 30% of the population of the USA is now considered obese.

Whether someone is classified as overweight or obese is generally determined on the basis of their body mass index (BMI) which is calculated by dividing body weight (kg) by height squared (m2). Thus, the units of BMI are $kg/m^2$ and it is possible to calculate the BMI range associated with minimum mortality in each decade of life. Overweight is defined as a BMI in the range 25-30 $kg/m^2$, and obesity as a BMI greater than 30 $kg/m^2$ (see table below).

| Classification Of Weight By Body Mass Index (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases there is an increased risk of death from a variety of causes that are independent of other risk factors. The most common diseases associated with obesity are cardiovascular disease (particularly hypertension), diabetes (obesity aggravates the development of diabetes), gall bladder disease (particularly cancer) and diseases of reproduction. The strength of the link between obesity and specific conditions varies. One of the strongest is the link with type 2 diabetes. Excess body fat underlies 64% of cases of diabetes in men and 77% of cases in women (Seidell, *Semin Vasc Med*, 5:3-14 (2005)). Research has shown that even a modest reduction in body weight can correspond to a significant reduction in the risk of developing coronary heart disease.

There are problems however with the BMI definition in that it does not take into account the proportion of body mass that is muscle in relation to fat (adipose tissue). To account for this, obesity can also be defined on the basis of body fat content: greater than 25% in males and greater than 30% in females.

Obesity considerably increases the risk of developing cardiovascular diseases as well. Coronary insufficiency, atheromatous disease, and cardiac insufficiency are at the forefront of the cardiovascular complications induced by obesity. It is estimated that if the entire population had an ideal weight, the risk of coronary insufficiency would decrease by 25% and the risk of cardiac insufficiency and of cerebral vascular accidents would decrease by 35%. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for diabetes and coronary heart disease and the potential value of an integrated approach to the prevention of these conditions based on the prevention of obesity (Perry, I. J., et al., *BMJ* 310, 560-564 (1995)).

Diabetes has also been implicated in the development of kidney disease, eye diseases and nervous system problems. Kidney disease, also called nephropathy, occurs when the kidney's "filter mechanism" is damaged and protein leaks into urine in excessive amounts and eventually the kidney fails. Diabetes is also a leading cause of damage to the retina at the back of the eye and increases risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment is to offer diet and life style advice to patients such as reducing the fat content of their diet and increasing their physical activity. However, many patients find this difficult and need additional help from drug therapy to maintain results from these efforts.

Most currently marketed products have been unsuccessful as treatments for obesity because of a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of patients led to its withdrawal by the FDA in 1998.

In addition, two drugs have been launched in the USA and Europe: Orlistat (Xenical™) a drug that prevents absorption of fat by the inhibition of pancreatic lipase, and Sibutramine (Reductil™), a 5-HT/noradrenaline re-uptake inhibitor. However, side effects associated with these products may limit their long-term utility. Treatment with Xenical™ is reported to induce gastrointestinal distress in some patients, while Sibutramine has been associated with raised blood pressure in some patients.

Serotonin (5-HT) neurotransmission plays an important role in numerous physiological processes both in physical and in psychiatric disorders. 5-HT has been implicated in the regulation of feeding behavior. 5-HT is believed to work by inducing a feeling of satiety, such that a subject with enhanced 5-HT stops eating earlier and fewer calories are consumed. It has been shown that a stimulatory action of 5-HT on the $5-HT_{2C}$ receptor plays an important role in the control of eating and in the anti-obesity effect of d-fenfluramine. As the $5-HT_{2C}$ receptor is expressed in high density in the brain (notably in the limbic structures, extrapyramidal pathways, thalamus and hypothalamus i.e. PVN and DMH, and predominantly in the choroid plexus) and is expressed in low density or is absent in peripheral tissues, a selective $5-HT_{2C}$ receptor agonist can be a more effective and safe anti-obesity agent. Also, 5-HT$_{2C}$ knockout mice are overweight with cognitive impairment and susceptibility to seizure.

It is believed that the 5-HT$_{2C}$ receptor may play a role in obsessive compulsive disorder, some forms of depression, and epilepsy. Accordingly, agonists can have anti-panic properties, and properties useful for the treatment of sexual dysfunction.

In sum, the 5-HT$_{2C}$ receptor is a receptor target for the treatment of obesity and psychiatric disorders, and it can be seen that there is a need for selective 5-HT$_{2C}$ agonists which safely decrease food intake and body weight.

The present invention pertains to certain salts of the selective 5-HT$_{2C}$-receptor agonist 8-chloro-1-methyl-2,3,4,5-tetrahydro-1H-3-benzazepine, and pharmaceutical compositions comprising them. Like many pharmaceutically useful compounds, 8-chloro-1-methyl-2,3,4,5-tetrahydro-1H-3-benzazepine contains an asymmetric carbon atom and thus it can exist as different optical isomers. Optical isomers of pharmaceutically useful compounds may posses significantly different physiological activity and therefore, compounds useful for resolving mixtures of optical isomers are needed. One method of resolving pharmaceutically useful compounds containing one or more asymmetric carbon atom is by the formation of diastereoisomeric salts. Once resolved, such salts are useful for preparing pharmaceutical compositions directly, without the need for further processing the resolved pharmaceutically useful compound to another salt form, or to the free base or free acid.

One aspect of the present invention pertains to optically active acid salts of (R)-8-chloro-1-methyl-2,3,4,5-tetrahydro-1H-3-benzazepine (Compound 1), and are useful for, inter alia, weight management, including weight loss and the maintenance of weight loss. Compound 1 is disclosed in PCT patent publication WO2003/086303, which is incorporated herein by reference in its entirety.

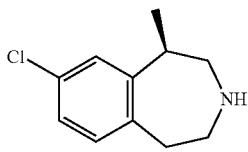

1

Various synthetic routes to (R)-8-chloro-1-methyl-2,3,4,5-tetrahydro-1H-3-benzazepine, its related salts, enantiomers, crystalline forms, and intermediates, have been reported in PCT publications, WO 2005/019179, WO 2006/069363, WO 2007/120517, WO 2008/070111, WO 2009/111004, and in U.S. provisional application 61/396,752 each of which is incorporated herein by reference in its entirety.

Combinations of (R)-8-Chloro-1-methyl-2,3,4,5-tetrahydro-1H-3-benzazepine with other agents, including without limitation, phentermine, and uses of such combinations in therapy are described in WO 2006/071740, which is incorporated herein by reference in its entirety The following United States provisional applications are related to (R)-8-chloro-1-methyl-2,3,4,5-tetrahydro-1H-3-benzazepine: 61/402,578; 61/403,143; 61/402,580; 61/402,628; 61/403,149; 61/402,589; 61/402,611; 61/402,565; 61/403,185; each of which is incorporated herein by reference in its entirety.

The following applications are related to (R)-8-chloro-1-methyl-2,3,4,5-tetrahydro-1H-3-benzazepine and have the same filing date as the subject application: PCT/US11/49914, a PCT application which claims priority to United States provisional applications 61/402,578 and 61/403,143; PCT/US11/49936, a PCT application which claims priority to United States provisional applications 61/402,628 and 61/403,149; PCT/US11/49953, a PCT application which claims priority to U.S. provisional application 61/402,589; PCT/US11/49960, a PCT application which claims priority to U.S. provisional application 61/402,611; and PCT/US11/49955, a PCT application which claims priority to United States provisional applications 61/402,565 and 61/403,185; each of which is incorporated herein by reference in its entirety.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans. In December 2009, Arena Pharmaceuticals submitted a New Drug Application, or NDA, for lorcaserin to the FDA. The NDA submission is based on an extensive data package from lorcaserin's clinical development program that includes 18 clinical trials totaling 8,576 patients. The pivotal phase 3 clinical trial program evaluated nearly 7,200 patients treated for up to two years, and showed that lorcaserin consistently produced significant weight loss with excellent tolerability. About two-thirds of patients achieved at least 5% weight loss and over one-third achieved at least 10% weight loss. On average, patients lost 17 to 18 pounds or about 8% of their weight. Secondary endpoints, including body composition, lipids, cardiovascular risk factors and glycemic parameters improved compared to placebo. In addition, heart rate and blood pressure went down. Lorcaserin did not increase the risk of cardiac valvulopathy. Lorcaserin improved quality of life, and there was no signal for depression or suicidal ideation. The only adverse event that exceeded the placebo rate by 5% was generally mild or moderate, transient headache. Based on a normal BMI of 25, patients in the first phase 3 trial lost about one-third of their excess body weight. The average weight loss was 35 pounds or 16% of body weight for the top quartile of patients in the second phase 3 trial.

In view of the growing demand for compounds useful in the treatment of disorders related to the 5-HT$_{2C}$ receptor, (R)-8-chloro-1-methyl-2,3,4,5-tetrahydro-1H-3-benzazepine has emerged has an important new compound. Accordingly, new salts and pharmaceutical compositions of (R)-8-chloro-1-methyl-2,3,4,5-tetrahydro-1H-3-benzazepine, and processes for their preparation are needed. The salts and processes described herein help meet these and other needs.

SUMMARY OF THE INVENTION

A priori, it is difficult to predict with confidence which salts of a particular compound will be solid, stable, and readily isolable. Salts of chiral amines with optically active acids are no exception. It is only through diligent experimentation that a stable, solid-state salt may be discovered; once that salt is in-hand however, the artisan of ordinary skill is equipped to resolve its diastereoisomers. In the course of preparing the salts of the present invention, many salt-forming agents commonly used in the pharmaceutical industry (see e.g. Berge, et al., *Journal of Pharmaceutical Sciences*, 66:1-19 (1977)) were investigated. DL-lactate, D-gluconate, and D-lactobionate salts of (R)-8-chloro-1-methyl-2,3,4,5-tetrahydro-1H-3-benzazepine were prepared, but in contrast to the crystalline salts of the present invention, they failed to crystallize.

One aspect of the present invention pertains to certain optically active acid salts of (R)-8-chloro-1-methyl-2,3,4,5- tetrahydro-1H-3-benzazepine (Compound 1) and pharmaceutically acceptable solvates and hydrates thereof.

One aspect of the present invention pertains to certain optically active acid salts of (R)-8-chloro-1-methyl-2,3,4,5-tetrahydro-1H-3-benzazepine Compound 1.

One aspect of the present invention pertains to salts selected from: (R)-8-chloro-1-methyl-2,3,4,5-tetrahydro-1H-3-benzazepine (1S)-(+)-10-camsylate salt; (R)-8-chloro-1-methyl-2,3,4,5-tetrahydro-1H-3-benzazepine hemi-L-malate salt; (R)-8-chloro-1-methyl-2,3,4,5-tetrahydro-1H-3-benzazepine L-glutamate salt; (R)-8-chloro-1-methyl-2,3,4,5-tetrahydro-1H-3-benzazepine L-aspartate salt; (R)-8-chloro-1-methyl-2,3,4,5-tetrahydro-1H-3-benzazepine hemimucate salt; (R)-8-chloro-1-methyl-2,3,4,5-tetrahydro-1H-3-benzazepine pyroglutamate salt; (R)-8-chloro-1-methyl-2,3,4,5-tetrahydro-1H-3-benzazepine glucuronate salt; and (R)-8-chloro-1-methyl-2,3,4,5-tetrahydro-1H-3-benzazepine di-camphorate salt; and pharmaceutically acceptable solvates and hydrates thereof.

One aspect of the present invention pertains to pharmaceutical compositions comprising a salt of the present invention and a pharmaceutically acceptable carrier.

One aspect of the present invention pertains to processes for preparing a pharmaceutical composition comprising admixing a salt of the present invention, and a pharmaceutically acceptable carrier.

One aspect of the present invention pertains to bulk pharmaceutical compositions suitable for the manufacture of dosage forms for weight management, comprising a salt of the present invention, and a pharmaceutically acceptable carrier.

One aspect of the present invention pertains to processes for preparing bulk pharmaceutical compositions suitable for the manufacture of dosage forms for weight management, comprising admixing a salt of the present invention, and a pharmaceutically acceptable carrier.

One aspect of the present invention pertains to methods for weight management, comprising administering to an individual in need thereof, a therapeutically effective amount of a salt or a pharmaceutical composition of the present invention.

One aspect of the present invention pertains to the use of salts of the present invention in the manufacture of a medicament for weight management in an individual.

One aspect of the present invention pertains to salts and pharmaceutical compositions of the present invention, for use in a method of treatment of the human or animal body by therapy.

DETAILED DESCRIPTION

Figure 1:
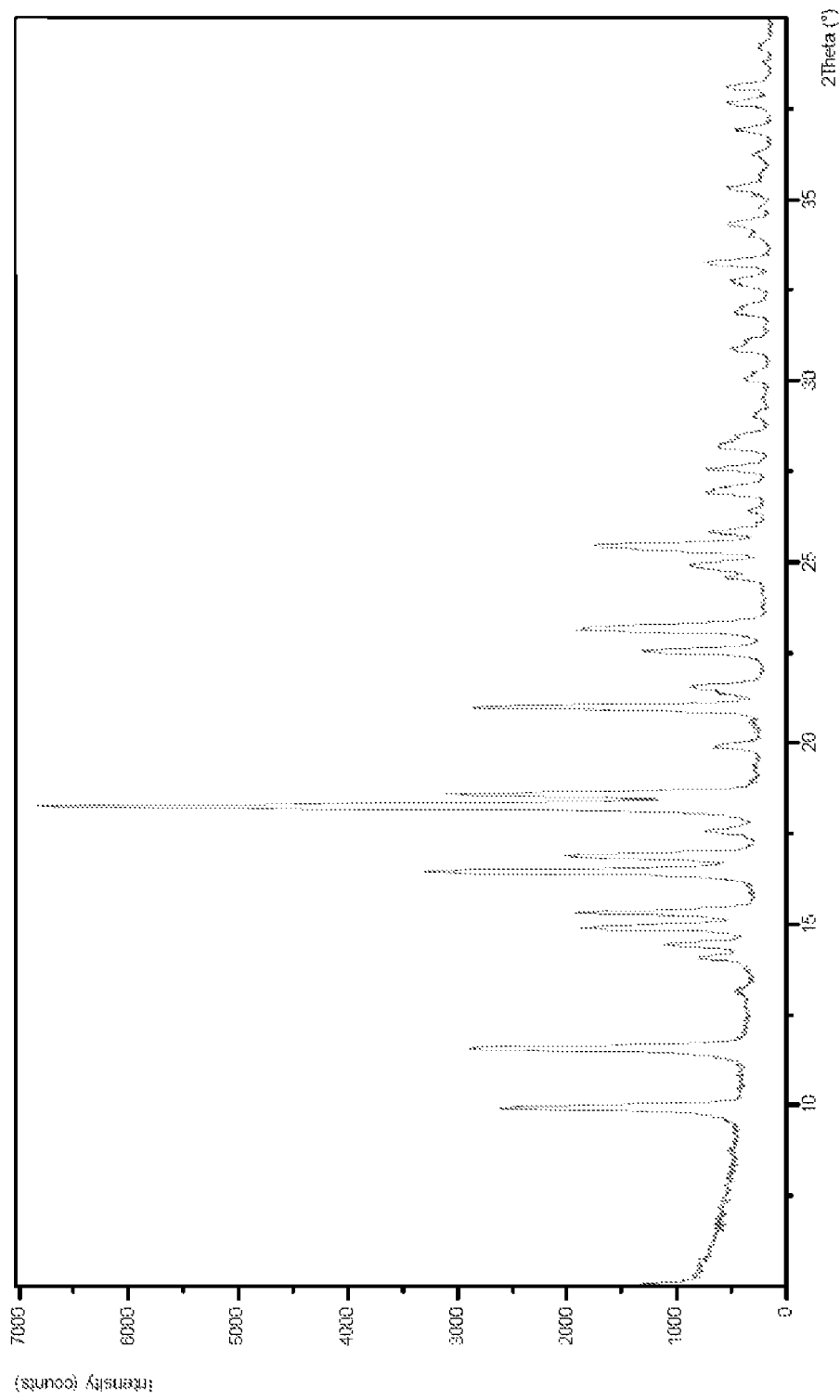
FIG. 1: PXRD of Compound 1 (1S)-(+)-10-Camsylate Salt, Form I.

It should be appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable subcombination.

DEFINITIONS

For clarity and consistency, the following definitions will be used throughout this patent document.

The term "agonist" refers to a moiety that interacts with and activates a receptor, such as the 5-HT$_{2C}$ serotonin receptor, and initiates a physiological or pharmacological response characteristic of that receptor.

The term "individual" refers to both humans and non-human mammals. Non-human mammals include but are not limited to rodents such as mice and rats, etc. rabbits, dogs, cats, swine, cattle, sheep, horses, and non-human primates such as monkeys and apes, etc.

The term "pharmaceutical composition" refers to a composition comprising at least one active ingredient; including but not limited to Compound 1 and pharmaceutically acceptable salts, solvates and hydrates thereof, whereby the composition is amenable to investigation for a specified, efficacious outcome in a mammal (for example, without limitation, a human). Those of ordinary skill in the art will understand and appreciate the techniques appropriate for determining whether an active ingredient has a desired efficacious outcome based upon the needs of the artisan.

The term "therapeutically effective amount" refers to the amount of active compound or pharmaceutical agent that elicits the biological or medicinal response in a tissue, system, animal, individual or human that is being sought by a researcher, veterinarian, medical doctor or other clinician or caregiver or by an individual, which includes one or more of the following:

(1) Preventing the disease, for example, preventing a disease, condition or disorder in an individual that may be predisposed to the disease, condition or disorder but does not yet experience or display the pathology or symptomatology of the disease;

(2) Inhibiting the disease, for example, inhibiting a disease, condition or disorder in an individual that is experiencing or displaying the pathology or symptomatology of the disease, condition or disorder (i.e., arresting further development of the pathology and/or symptomatology); and (3) Ameliorating the disease, for example, ameliorating a disease, condition or disorder in an individual that is experiencing or displaying the pathology or symptomatology of the disease, condition or disorder (i.e., reversing the pathology and/or symptomatology).

The term "treatment" as used herein refers to one or more of the following:

(1) prevention of a disease, for example, prevention of a disease, condition or disorder in an individual that may be predisposed to the disease, condition or disorder but does not yet experience or display the pathology or symptomatology of the disease;

(2) inhibition of a disease, for example, inhibition of a disease, condition or disorder in an individual that is experiencing or displaying the pathology or symptomatology of the disease, condition or disorder (i.e., arresting further development of the pathology and/or symptomatology); and (3) amelioration of a disease, for example, amelioration of a disease, condition or disorder in an individual that is experiencing or displaying the pathology or symptomatology of the disease, condition or disorder (i.e., reversing the pathology and/or symptomatology).

Whether an individual is in need of treatment is a judgment made by a caregiver (e.g. nurse practitioner, physician, physician assistant, nurse, etc. in the case of humans; veterinarian in the case of animals, including non-human mammals) that an individual or animal requires or will benefit from treatment. This judgment is made based on a variety of factors that are in the realm of a caregiver's expertise, but that includes the knowledge that the individual or animal is ill, or will become ill, as the result of a disease, condition or disorder that is treatable by Compound 1 and pharmaceutically acceptable salts, solvates and hydrates thereof. Accordingly, Compound 1 and pharmaceutically acceptable salts, solvates and hydrates thereof can be used in a protective or preventive manner; or Compound 1 and pharmaceutically acceptable salts, solvates and hydrates thereof can be used to alleviate, inhibit or ameliorate a disease, condition or disorder.

The term "weight management" as used herein refers to controlling body weight and in the context of the present invention is directed toward weight loss and the maintenance of weight loss (also called weight maintenance herein). In addition to controlling body weight, weight management includes controlling parameters related to body weight, for example, BMI, percent body fat and waist circumference. For example, weight management for an individual who is overweight or obese can mean losing weight with the goal of keeping weight in a healthier range. Also, for example, weight management for an individual who is overweight or obese can include losing body fat or circumference around the waist with or without the loss of body weight.

The term "maintenance of weight loss" or "weight maintenance" as used herein refers to preventing, reducing or controlling weight gain after weight loss. It is well known that weight gain often occurs after weight loss. Weight loss can occur, for example, from dieting, exercising, illness, drug treatment, surgery or any combination of these methods, but often an individual that has lost weight will regain some or all of the lost weight. Therefore, weight maintenance in an individual who has lost weight can include preventing weight gain after weight loss, reducing the amount of weigh gained after weight loss, controlling weight gain after weight loss or slowing the rate of weight gain after weight loss.

The term "optically active acid salt" as used herein means a salt in which the anion is derived from the deprotonation of an optically active acid. The following table provides certain non-limiting examples of optically active acids.

| Chemical Name | Structure |
| --- | --- |
| (1S)-(+)-10-camphorsulfonic acid | 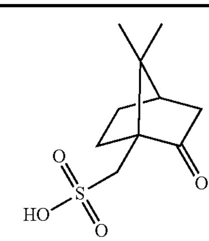 |
| L-malic acid | 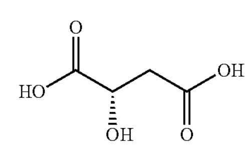 |
| L-glutamic acid | 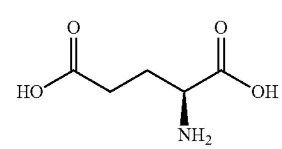 |
| L-aspartic acid | 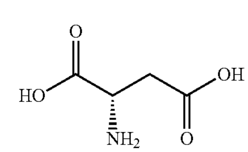 |

-continued

| Chemical Name | Structure |
|---|---|
| mucic acid | 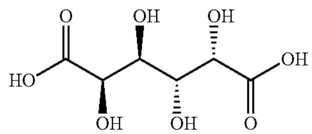 [SMILES: O=C(O)[C@@H](O)[C@H](O)[C@H](O)[C@@H](O)C(=O)O] |
| pyroglutamatic acid | 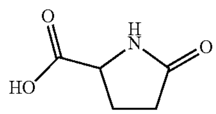 |
| glucuronic acid | 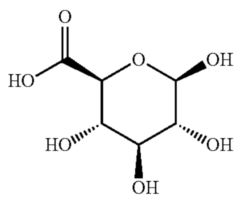 [SMILES: O=C(O)[C@H]1O[C@@H](O)[C@H](O)[C@@H](O)[C@@H]1O] |
| (1R,3S)-(+)-camphoric acid | 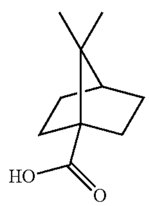 |
| D-gluconic acid | 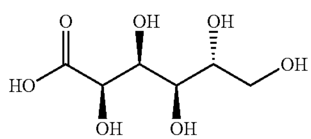 [SMILES: O=C(O)[C@H](O)[C@@H](O)[C@H](O)[C@H](O)CO] |
| L-lactic acid | 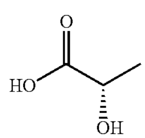 |
| L-tartaric acid | 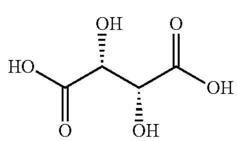 |
| D-glycero-D-gulo-heptonic acid | 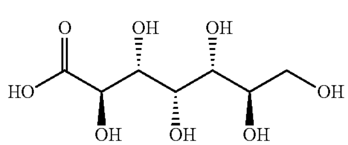 [SMILES: O=C(O)[C@H](O)[C@H](O)[C@@H](O)[C@H](O)[C@H](O)CO] |
| D-lactobionic acid | 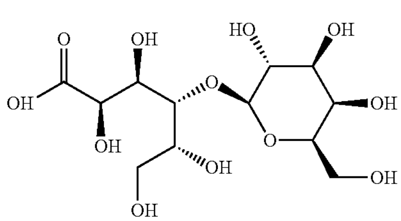 [SMILES: O=C(O)[C@H](O)[C@@H](O)[C@H](O[C@@H]1O[C@H](CO)[C@H](O)[C@H](O)[C@H]1O)[C@H](O)CO] |

-continued

| Chemical Name | Structure |
|---|---|
| L-mandelic acid | 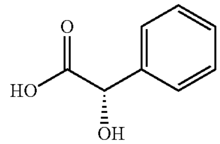 [SMILES: O=C(O)[C@@H](O)c1ccccc1] |
| (D)-(+)-pantothenic acid | 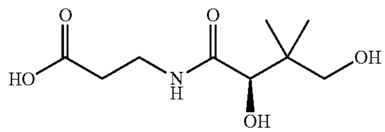 |
| dibenzoyl-L-tartaric acid | 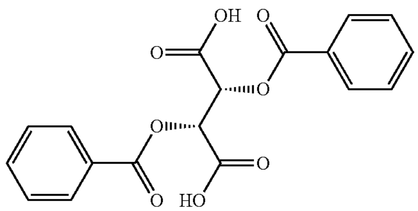 [SMILES: O=C(O[C@@H](C(=O)O)[C@@H](OC(=O)c1ccccc1)C(=O)O)c1ccccc1] |
| Di-p-toluoyl-L-tartaric acid | 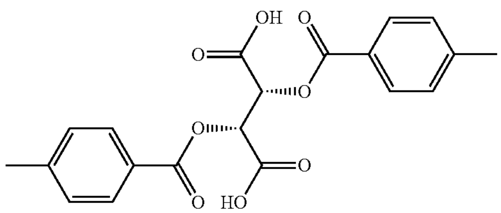 |
| (S)-2-phenylpropionic acid | 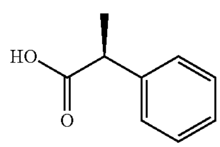 |
| L-N-acetylphenylalanine | 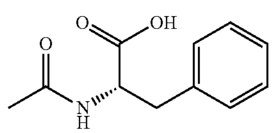 |
| (1R)-(+)-3-bromocamphor-8-sulfonic acid | 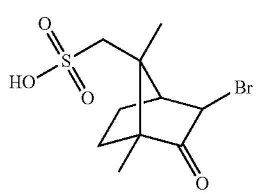 [SMILES: CC12CCC(C(Br)C1=O)C2(C)CS(=O)(=O)O] |
| (S)-2,3-isopropylideneglycerol hemiphthalate | 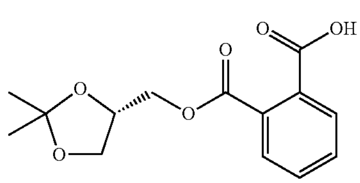 [SMILES: CC1(C)OC[C@@H](COC(=O)c2ccccc2C(=O)O)O1] |

| Chemical Name | Structure |
|---|---|
| Diacetyl-L-tartaric acid | 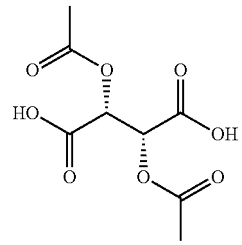 [SMILES: CC(=O)O[C@@H](C(=O)O)[C@@H](OC(C)=O)C(=O)O] |
| N-tosyl-L-glutamic acid | 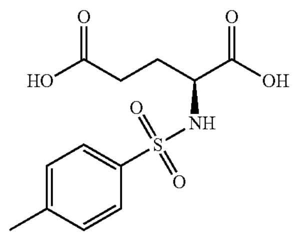 [SMILES: Cc1ccc(S(=O)(=O)N[C@@H](CCC(=O)O)C(=O)O)cc1] |
| (1S)-(−)-Camphanic acid | 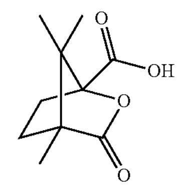 |

The term "diastereoisomeric" as used herein refers to the relationship between stereoisomers that are not enantiomers. Similarly, the term "diastereoisomeric salts" as used herein refers to the relationship between salts that comprise both a chiral anion and a chiral cation, wherein the salts are stereoisomers but are not enantiomers.

For example, in a salt consisting of an anion with one chiral center and a cation with one chiral center, there are four possible stereoisomers of the salt:
A. (R)-anion-(R)-cation;
B. (R)-anion-(S)-cation;
C. (S)-anion-(R)-cation; and
D. (S)-anion-(S)-cation.

In this example each salt has one enantiomeric salt and two diastereoisomeric salts. The various relationships between the four salts above is shown in the following table:

| Salt | Enantiomer of salt | Diastereoisomers of salt |
|---|---|---|
| A | D | B and C |
| B | C | A and D |
| C | B | A and D |
| D | A | B and C |

By way of further example, in a salt consisting of an anion with two chiral centers and a cation with one chiral center, there are eight possible stereoisomers of the salt:
E. (R,R)-anion-(R)-cation;
F. (R,R)-anion-(S)-cation;
G. (R,S)-anion-(R)-cation;
H. (R,S)-anion-(S)-cation;
I. (S,R)-anion-(R)-cation;
J. (S,R)-anion-(S)-cation;
K. (S,S)-anion-(R)-cation; and
L. (S,S)-anion-(S)-cation.

In this example each salt has one enantiomeric salt and six diastereoisomeric salts. The various relationships between the eight salts above is shown in the following table:

| Salt | Enantiomer of Salt | Diastereoisomers of Salt |
|---|---|---|
| E | L | F, G, H, I, J, and K |
| F | K | E, G, H, I, J, and L |
| G | J | E, F, H, I, K, and L |
| H | I | E, F, G, J, K, and L |
| I | H | E, F, G, J, K, and L |
| J | G | E, F, H, I, K, and L |
| K | F | E, G, H, I, J, and L |
| L | E | F, G, H, I, J, and K |

Salts of the Present Invention

The present invention is directed, inter alia, to solid, stable, and readily isolable salts of (R)-8-chloro-1-methyl-2,3,4,5-tetrahydro-1H-3-benzazepine and pharmaceutically acceptable solvates and hydrates thereof. The solid state properties of the crystalline forms of salts the present invention are summarized infra.

One aspect of the present invention pertains to salts selected from: (R)-8-chloro-1-methyl-2,3,4,5-tetrahydro-1H-3-benzazepine (1S)-(+)-10-camsylate salt; (R)-8-chloro-1-methyl-2,3,4,5-tetrahydro-1H-3-benzazepine hemi-L-malate salt; (R)-8-chloro-1-methyl-2,3,4,5-tetrahydro-1H-3-benzazepine L-glutamate salt; (R)-8-chloro-1-methyl-2,3,4,5-tetrahydro-1H-3-benzazepine L-aspartate salt; (R)-8-chloro-1-methyl-2,3,4,5-tetrahydro-1H-3-benzazepine hemimucate salt; (R)-8-chloro-1-methyl-2,3,4,5-tetrahydro-1H-3-benzazepine pyroglutamate salt; (R)-8-chloro-1-methyl-2,3,4,5-tetrahydro-1H-3-benzazepine glucuronate salt; and (R)-8-chloro-1-methyl-2,3,4,5-tetrahydro-1H-3-benzazepine di-camphorate salt; and pharmaceutically acceptable solvates and hydrates thereof.

One aspect of the present invention pertains to salts selected from: (R)-8-chloro-1-methyl-2,3,4,5-tetrahydro-1H-3-benzazepine (1S)-(+)-10-camsylate salt; (R)-8-chloro-1-methyl-2,3,4,5-tetrahydro-1H-3-benzazepine hemi-L-malate salt; (R)-8-chloro-1-methyl-2,3,4,5-tetrahydro-1H-3-benzazepine L-glutamate salt; (R)-8-chloro-1-methyl-2,3,4,5-tetrahydro-1H-3-benzazepine L-aspartate salt; (R)-8-chloro-1-methyl-2,3,4,5-tetrahydro-1H-3-benzazepine hemimucate salt; (R)-8-chloro-1-methyl-2,3,4,5-tetrahydro-1H-3-benzazepine pyroglutamate salt; and (R)-8-chloro-1-methyl-2,3,4,5-tetrahydro-1H-3-benzazepine glucuronate salt; and pharmaceutically acceptable solvates and hydrates thereof.

One aspect of the present invention pertains to salts selected from: (R)-8-chloro-1-methyl-2,3,4,5-tetrahydro-1H-3-benzazepine (1S)-(+)-10-camsylate salt; (R)-8-chloro-1-methyl-2,3,4,5-tetrahydro-1H-3-benzazepine hemi-L-malate salt; (R)-8-chloro-1-methyl-2,3,4,5-tetrahydro-1H-3-benzazepine L-glutamate salt; (R)-8-chloro-1-methyl-2,3,4,5-tetrahydro-1H-3-benzazepine L-aspartate salt; (R)-8-chloro-1-methyl-2,3,4,5-tetrahydro-1H-3-benzazepine hemimucate salt; (R)-8-chloro-1-methyl-2,3,4,5-tetrahydro-1H-3-benzazepine pyroglutamate salt; (R)-8-chloro-1-methyl-2,3,4,5-tetrahydro-1H-3-benzazepine glucuronate salt; and (R)-8-chloro-1-methyl-2,3,4,5-tetrahydro-1H-3-benzazepine di-camphorate salt solvate.

One aspect of the present invention pertains to (R)-8-chloro-1-methyl-2,3,4,5-tetrahydro-1H-3-benzazepine di-camphorate salt solvate.

One aspect of the present invention pertains to (R)-8-chloro-1-methyl-2,3,4,5-tetrahydro-1H-3-benzazepine (1S)-(+)-10-camsylate salt.

One aspect of the present invention pertains to (R)-8-chloro-1-methyl-2,3,4,5-tetrahydro-1H-3-benzazepine hemi-L-malate salt.

One aspect of the present invention pertains to (R)-8-chloro-1-methyl-2,3,4,5-tetrahydro-1H-3-benzazepine L-glutamate salt.

One aspect of the present invention pertains to (R)-8-chloro-1-methyl-2,3,4,5-tetrahydro-1H-3-benzazepine L-aspartate salt.

One aspect of the present invention pertains to (R)-8-chloro-1-methyl-2,3,4,5-tetrahydro-1H-3-benzazepine hemimucate salt.

One aspect of the present invention pertains to (R)-8-chloro-1-methyl-2,3,4,5-tetrahydro-1H-3-benzazepine pyroglutamate salt.

One aspect of the present invention pertains to (R)-8-chloro-1-methyl-2,3,4,5-tetrahydro-1H-3-benzazepine glucuronate salt.

One aspect of the present invention pertains to (R)-8-chloro-1-methyl-2,3,4,5-tetrahydro-1H-3-benzazepine di-camphorate salt solvate.

One aspect of the present invention pertains to 8-chloro-1-methyl-2,3,4,5-tetrahydro-1H-3-benzazepine (1S)-(+)-10-camsylate salt.

One aspect of the present invention pertains to 8-chloro-1-methyl-2,3,4,5-tetrahydro-1H-3-benzazepine hemi-L-malate salt.

One aspect of the present invention pertains to 8-chloro-1-methyl-2,3,4,5-tetrahydro-1H-3-benzazepine L-glutamate salt.

One aspect of the present invention pertains to 8-chloro-1-methyl-2,3,4,5-tetrahydro-1H-3-benzazepine L-aspartate salt.

One aspect of the present invention pertains to 8-chloro-1-methyl-2,3,4,5-tetrahydro-1H-3-benzazepine hemimucate salt.

One aspect of the present invention pertains to 8-chloro-1-methyl-2,3,4,5-tetrahydro-1H-3-benzazepine pyroglutamate salt.

One aspect of the present invention pertains to 8-chloro-1-methyl-2,3,4,5-tetrahydro-1H-3-benzazepine glucuronate salt.

One aspect of the present invention pertains to 8-chloro-1-methyl-2,3,4,5-tetrahydro-1H-3-benzazepine di-camphorate salt solvate.

One aspect of the present invention pertains to (±)-8-chloro-1-methyl-2,3,4,5-tetrahydro-1H-3-benzazepine (1S)-(+)-10-camsylate salt.

One aspect of the present invention pertains to (±)-8-chloro-1-methyl-2,3,4,5-tetrahydro-1H-3-benzazepine hemi-L-malate salt.

One aspect of the present invention pertains to (±)-8-chloro-1-methyl-2,3,4,5-tetrahydro-1H-3-benzazepine L-glutamate salt.

One aspect of the present invention pertains to (±)-8-chloro-1-methyl-2,3,4,5-tetrahydro-1H-3-benzazepine L-aspartate salt.

One aspect of the present invention pertains to (±)-8-chloro-1-methyl-2,3,4,5-tetrahydro-1H-3-benzazepine hemimucate salt.

One aspect of the present invention pertains to (±)-8-chloro-1-methyl-2,3,4,5-tetrahydro-1H-3-benzazepine pyroglutamate salt.

One aspect of the present invention pertains to (±)-8-chloro-1-methyl-2,3,4,5-tetrahydro-1H-3-benzazepine glucuronate salt.

One aspect of the present invention pertains to (±)-8-chloro-1-methyl-2,3,4,5-tetrahydro-1H-3-benzazepine di-camphorate salt solvate.

One aspect of the present invention pertains to (S)-8-chloro-1-methyl-2,3,4,5-tetrahydro-1H-3-benzazepine (1S)-(+)-10-camsylate salt.

One aspect of the present invention pertains to (S)-8-chloro-1-methyl-2,3,4,5-tetrahydro-1H-3-benzazepine hemi-L-malate salt.

One aspect of the present invention pertains to (S)-8-chloro-1-methyl-2,3,4,5-tetrahydro-1H-3-benzazepine L-glutamate salt.

One aspect of the present invention pertains to (S)-8-chloro-1-methyl-2,3,4,5-tetrahydro-1H-3-benzazepine L-aspartate salt.

One aspect of the present invention pertains to (S)-8-chloro-1-methyl-2,3,4,5-tetrahydro-1H-3-benzazepine hemimucate salt.

One aspect of the present invention pertains to (S)-8-chloro-1-methyl-2,3,4,5-tetrahydro-1H-3-benzazepine pyroglutamate salt.

One aspect of the present invention pertains to (S)-8-chloro-1-methyl-2,3,4,5-tetrahydro-1H-3-benzazepine glucuronate salt.

One aspect of the present invention pertains to (S)-8-chloro-1-methyl-2,3,4,5-tetrahydro-1H-3-benzazepine di-camphorate salt solvate.

One aspect of the present invention pertains to pharmaceutical compositions comprising a salt of the present invention.

One aspect of the present invention pertains to process for preparing a pharmaceutical composition comprising admixing a salt of the present invention and a pharmaceutically acceptable carrier.

One aspect of the present invention pertains to methods for weight management, comprising administering to an individual in need thereof, a therapeutically effective amount of a salt of the present invention.

One aspect of the present invention pertains to the use of salts of the present invention, in the manufacture of a medicament for weight management in an individual.

One aspect of the present invention pertains to salts of the present invention, for use in a method of treatment of the human or animal body by therapy.

One aspect of the present invention pertains to salts of the present invention, for use in a method of weight management.

One aspect of the present invention pertains to salts of the present invention, for use in a method of weight loss.

One aspect of the present invention pertains to salts of the present invention, for use in a method of maintenance of weight loss.

One aspect of the present invention pertains to salts of the present invention, for use in a method of decreasing food consumption.

One aspect of the present invention pertains to salts of the present invention, for use in a method of increasing meal-related satiety.

One aspect of the present invention pertains to salts of the present invention, for use in a method of reducing pre-meal hunger.

One aspect of the present invention pertains to salts of the present invention, for use in a method of reducing intra-meal food intake.

One aspect of the present invention pertains to salts of the present invention, for use in a method of weight management further comprising a reduced-calorie diet.

One aspect of the present invention pertains to salts of the present invention, for use in a method of weight management further comprising a program of regular exercise.

One aspect of the present invention pertains to salts of the present invention, for use in a method of weight management further comprising a reduced-calorie diet and a program of regular exercise.

One aspect of the present invention pertains to salts of the present invention, for use in a method of weight management in an obese patient with an initial body mass index ≥30 kg/m$^2$.

One aspect of the present invention pertains to salts of the present invention, for use in a method of weight management in an overweight patient with an initial body mass index ≥27 kg/m$^2$ in the presence of at least one weight related co-morbid condition.

One aspect of the present invention pertains to salts of the present invention, for use in a method of weight management in an overweight patient with an initial body mass index ≥27 kg/m$^2$ in the presence of at least one weight related co-morbid condition selected from: hypertension, dyslipidemia, cardiovascular disease, glucose intolerance, and sleep apnea.

On aspect of the present invention pertains to salts of the present invention, for use in a method of weight management in an individual with an initial body mass index ≥30 kg/m$^2$.

On aspect of the present invention pertains to salts of the present invention, for use in a method of weight management in an individual with an initial body mass index ≥27 kg/m$^2$.

On aspect of the present invention pertains to salts of the present invention, for use in a method of weight management in an individual with an initial body mass index ≥27 kg/m$^2$ in the presence of at least one weight related co-morbid condition.

On aspect of the present invention pertains to salts of the present invention, for use in a method of weight management in an individual with an initial body mass index ≥27 kg/m$^2$ in the presence of at least one weight related co-morbid condition selected from: hypertension, dyslipidemia, cardiovascular disease, glucose intolerance, and sleep apnea.

On aspect of the present invention pertains to salts of the present invention, for use in a method of weight management in an individual with an initial body mass index ≥25 kg/m$^2$.

On aspect of the present invention pertains to salts of the present invention, for use in a method of weight management in an individual with an initial body mass index ≥25 kg/m$^2$ in the presence of at least one weight related co-morbid condition.

On aspect of the present invention pertains to salts of the present invention, for use in a method of weight management in an individual with an initial body mass index ≥25 kg/m$^2$ in the presence of at least one weight related co-morbid condition selected from: hypertension, dyslipidemia, cardiovascular disease, glucose intolerance, and sleep apnea.

One aspect of the present invention pertains to salts of the present invention, for use in a method of weight management in combination with phentermine.

Crystalline Salts

Polymorphism is the ability of a substance to exist as two or more crystalline phases that have different arrangements and/or conformations of the molecules in the crystal lattice. Polymorphs show the same properties in the liquid or gaseous state but they may behave differently in the solid state.

Besides single-component polymorphs, drugs can also exist as salts and other multicomponent crystalline phases. For example, solvates and hydrates may contain an API host and either solvent or water molecules, respectively, as guests. Analogously, when the guest compound is a solid at room temperature, the resulting form is often called a cocrystal. Salts, solvates, hydrates, and cocrystals may show polymorphism as well. Crystalline phases that share the same API host, but differ with respect to their guests, may be referred to as pseudopolymorphs of one another.

Solvates contain molecules of the solvent of crystallization in a definite crystal lattice. Solvates, in which the solvent of crystallization is water, are termed hydrates. Because water is a constituent of the atmosphere, hydrates of drugs may be formed rather easily.

Recently, polymorph screens of 245 compounds revealed that about 90% of them exhibited multiple solid forms. Overall, approximately half the compounds were polymorphic, often having one to three forms. About one-third of the compounds formed hydrates, and about one-third formed solvates. Data from cocrystal screens of 64 compounds showed that 60% formed cocrystals other than hydrates or solvates. (G. P. Stahly, *Crystal Growth & Design* (2007), 7(6), 1007-1026.)

The present invention is directed, inter alia, to crystalline salts of (R)-8-chloro-1-methyl-2,3,4,5-tetrahydro-1H-3-benzazepine and hydrates and solvates thereof. The crystalline forms of the salts of the present invention can be identified by unique solid state signatures with respect to, for example, differential scanning calorimetry (DSC), X-ray powder diffraction (PXRD), and other solid state methods. Further characterization with respect to water or solvent content of the crystalline salts of the present invention can be gauged by any of the following methods for example, thermogravimetric analysis (TGA), DSC and the like. For DSC, it is known that the temperatures observed will depend upon sample purity, the rate of temperature change, as well as sample preparation technique and the particular instrument employed. Thus, the values reported herein relating to DSC thermograms can vary by about ±6° C. The values reported herein relating to DSC thermograms can also vary by about ±20 joules per gram. For PXRD, the relative intensities of the peaks can vary, depending upon the sample preparation technique, the sample mounting procedure and the particular instrument employed. Moreover, instrument variation and other factors can often affect the 2θ values. Therefore, the peak assignments of diffraction patterns can vary by about ±0.2° 2θ. The relative intensities of the reported peaks can also vary. For TGA, the features reported herein can vary by about ±5° C. The TGA features reported herein can also vary by about ±2% weight change due to, for example, sample variation. Further characterization with respect to hygroscopicity of the crystalline salt can be gauged by, for example, dynamic moisture sorption (DMS). The DMS features reported herein can vary by about ±5% relative humidity. The DMS features reported herein can also vary by about ±5% weight change. The deliquescence relative humidity (DRH) measurements by water activity meter are sensitive to sample quality and quantity. The DRH measurements reported herein can vary by about ±5% RH.

Compound 1 (1S)-(+)-10-Camsylate Salt.

One aspect of the present invention pertains to (R)-8-chloro-1-methyl-2,3,4,5-tetrahydro-1H-3-benzazepine (1 S)-(+)-10-camsylate salt, Form I (Compound 1 (1 S)-(+)-10-camsylate salt, Form I). The physical properties of Compound 1 (1S)-(+)-10-camsylate salt, Form I are summarized in Table 1 below.

TABLE 1

| | Compound 1 (1S)-(+)-10-Camsylate Salt, Form I |
|---|---|
| PXRD | FIG. 1: Peaks of >20% relative intensity at 9.93, 11.58, 14.90, 15.32, 16.45, 16.88, 18.25, 18.57, 20.97, 23.14, and 25.44 °2θ |
| TGA | FIG. 2: about 0.2% weight loss up to about 150° C. |
| DSC | FIG. 2: extrapolated onset temperature: 176° C.; enthalpy of fusion 92 J/g |
| DMS | FIG. 3: 0.49% weight increase out to 90% RH |

Form I of Compound 1 (1S)-(+)-10-camsylate salt held residual solvent or a small amount of water. The small weight loss by TGA (0.215%) is too small to be a stoichiometric solvate; it may be a mixture of anhydrous solvated crystal phases. The melting onset by DSC was 176° C.

Form I of Compound 1 (1S)-(+)-10-camsylate salt was non-hygroscopic by DMS analysis, picking up about 0.49% out to and including the 90% RH hold at 25° C. The DRH was determined to be 99.8% RH by water activity measurement of a saturated aqueous solution with excess solid at 25° C.

Certain X-ray powder diffraction peaks for Form I of Compound 1 (1S)-(+)-10-camsylate salt are shown in Table 2 below.

TABLE 2

| Pos. (°2θ) | Rel. Int. (%) |
|---|---|
| 9.93 | 33.89 |
| 11.58 | 38.89 |
| 13.15 | 2.15 |
| 14.08 | 8.07 |
| 14.43 | 12.50 |
| 14.90 | 24.42 |
| 15.32 | 25.17 |
| 16.45 | 46.36 |
| 16.88 | 26.94 |
| 17.57 | 7.59 |
| 18.25 | 100.00 |
| 18.57 | 44.04 |
| 19.89 | 5.97 |
| 20.97 | 41.20 |
| 21.36 | 5.76 |
| 21.56 | 10.34 |
| 22.54 | 17.03 |
| 23.14 | 25.60 |
| 23.28 | 16.29 |
| 24.58 | 6.00 |
| 24.90 | 10.60 |
| 25.30 | 14.05 |
| 25.44 | 23.97 |
| 25.82 | 8.07 |
| 26.41 | 2.45 |
| 26.92 | 8.25 |
| 27.56 | 8.59 |
| 28.18 | 6.81 |
| 28.51 | 3.91 |
| 29.06 | 1.78 |
| 29.52 | 0.89 |
| 30.05 | 3.29 |
| 30.86 | 5.09 |
| 31.11 | 3.09 |
| 31.88 | 4.87 |
| 32.02 | 3.96 |
| 32.75 | 5.23 |
| 33.23 | 8.73 |
| 33.29 | 8.45 |
| 34.01 | 2.81 |
| 34.32 | 5.81 |
| 34.79 | 1.47 |
| 35.31 | 5.87 |
| 36.24 | 2.66 |
| 36.93 | 4.84 |
| 37.61 | 5.57 |
| 38.09 | 6.29 |
| 38.76 | 1.26 |
| 39.20 | 1.78 |

One aspect of the present invention is directed to a Compound 1 (1S)-(+)-10-camsylate salt having an X-ray powder diffraction pattern comprising a peak, in terms of 2θ, at about 18.25°. In some embodiments, the crystalline form has an X-ray powder diffraction pattern comprising a peak, in terms of 2θ, at about 16.45°. In some embodiments, the crystalline form has an X-ray powder diffraction pattern comprising peaks, in terms of 2θ, at about 18.25° and about 16.45°. In some embodiments, the crystalline form has an X-ray powder diffraction pattern comprising peaks, in terms of 2θ, at about 18.25° and about 18.57°. In some embodiments, the crystalline form has an X-ray powder diffraction pattern comprising peaks, in terms of 2θ, at about 18.25°, about 16.45°, and about 18.57°. In some embodiments, the crystalline form has an X-ray powder diffraction pattern comprising peaks, in terms of 2θ, at about 18.25°, about 16.45°, about 18.57°, about 20.97°, about 11.58°, about 9.93°, and about 16.88°. In some embodiments, the crystalline form has an X-ray powder diffraction pattern comprising peaks, in terms of 2θ, at about 18.25°, about 16.45°, about 18.57°, about 20.97°, about 11.58°, about 9.93°, about 16.88°, about 23.14°, about 15.32°, and about 14.90°. One aspect of the present invention is directed to a Compound 1 (1S)-(+)-10-camsylate salt having an X-ray powder diffraction pattern comprising one or more peaks listed in Table 2. In some embodiments, the crystalline form has an X-ray powder diffraction pattern substantially as shown in FIG. 1, wherein by "substantially" is meant that the reported peaks can vary by about ±0.2° 2θ, and also that the relative intensities of the reported peaks can vary.

In some embodiments, the Compound 1 (1S)-(+)-10-camsylate salt has a differential scanning calorimetry thermogram comprising an endotherm with an extrapolated onset temperature between about 160° C. and about 190° C. In some embodiments, the Compound 1 (1S)-(+)-10-camsylate salt has a differential scanning calorimetry thermogram comprising an endotherm with an extrapolated onset temperature at about 176° C. In some embodiments, the Compound 1 (1S)-(+)-10-camsylate salt has a differential scanning calorimetry thermogram comprising an endotherm with an associated heat flow of about 92 joules per gram. In some embodiments, the Compound 1 (1S)-(+)-10-camsylate salt has a differential scanning calorimetry thermogram substantially as shown in FIG. 2, wherein by "substantially" is meant that the reported DSC features can vary by about ±6° C. and by about ±20 joules per gram.

Figure 2:
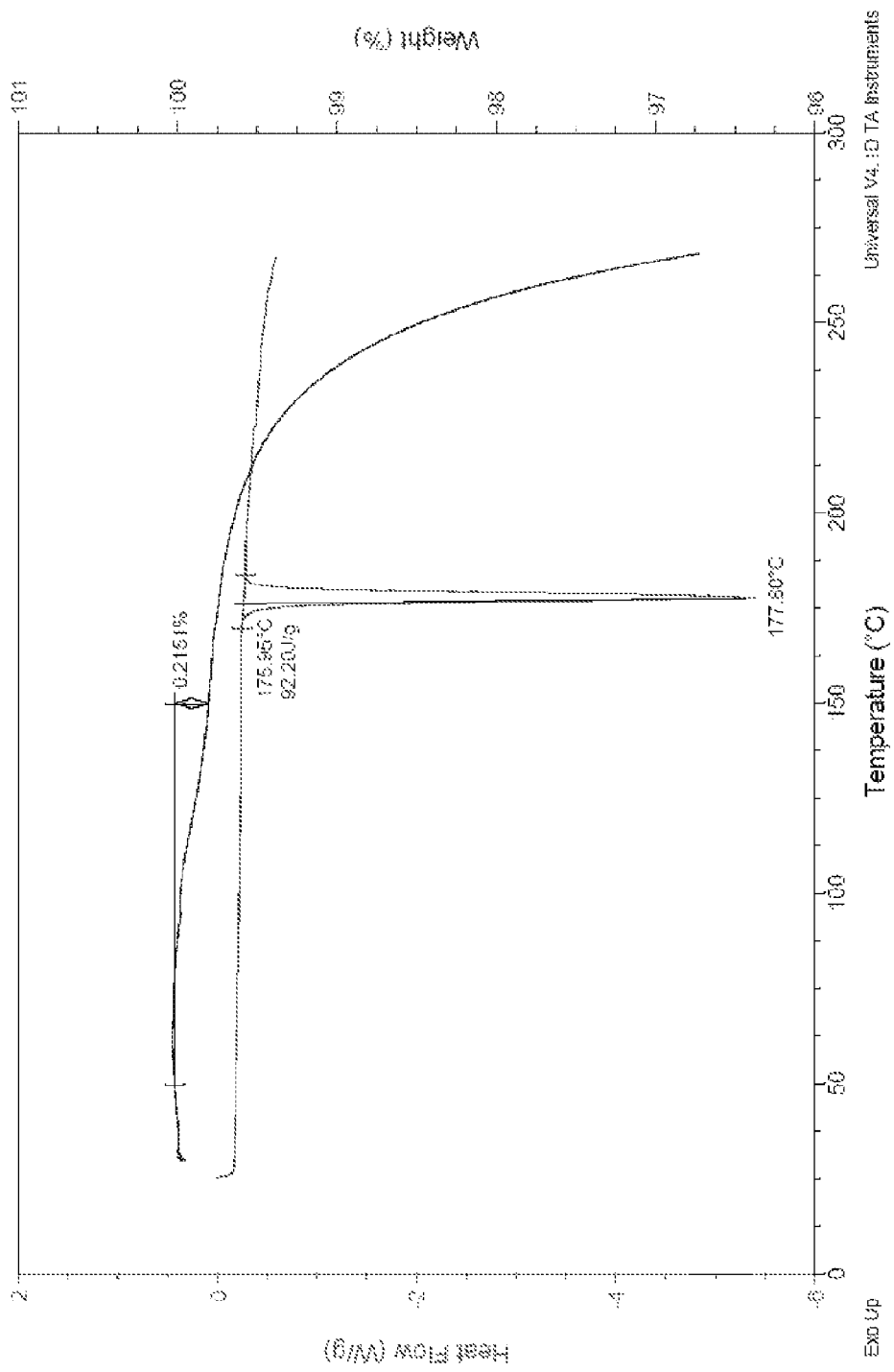
FIG. 2: DSC and TGA of Compound 1 (1S)-(+)-10-Camsylate Salt, Form I.

In some embodiments, the Compound 1 (1S)-(+)-10-camsylate salt has a thermogravimetric analysis profile substantially as shown in FIG. 2, wherein by "substantially" is meant that the reported TGA features can vary by about ±5° C. and by about ±2% weight change.

Figure 3:
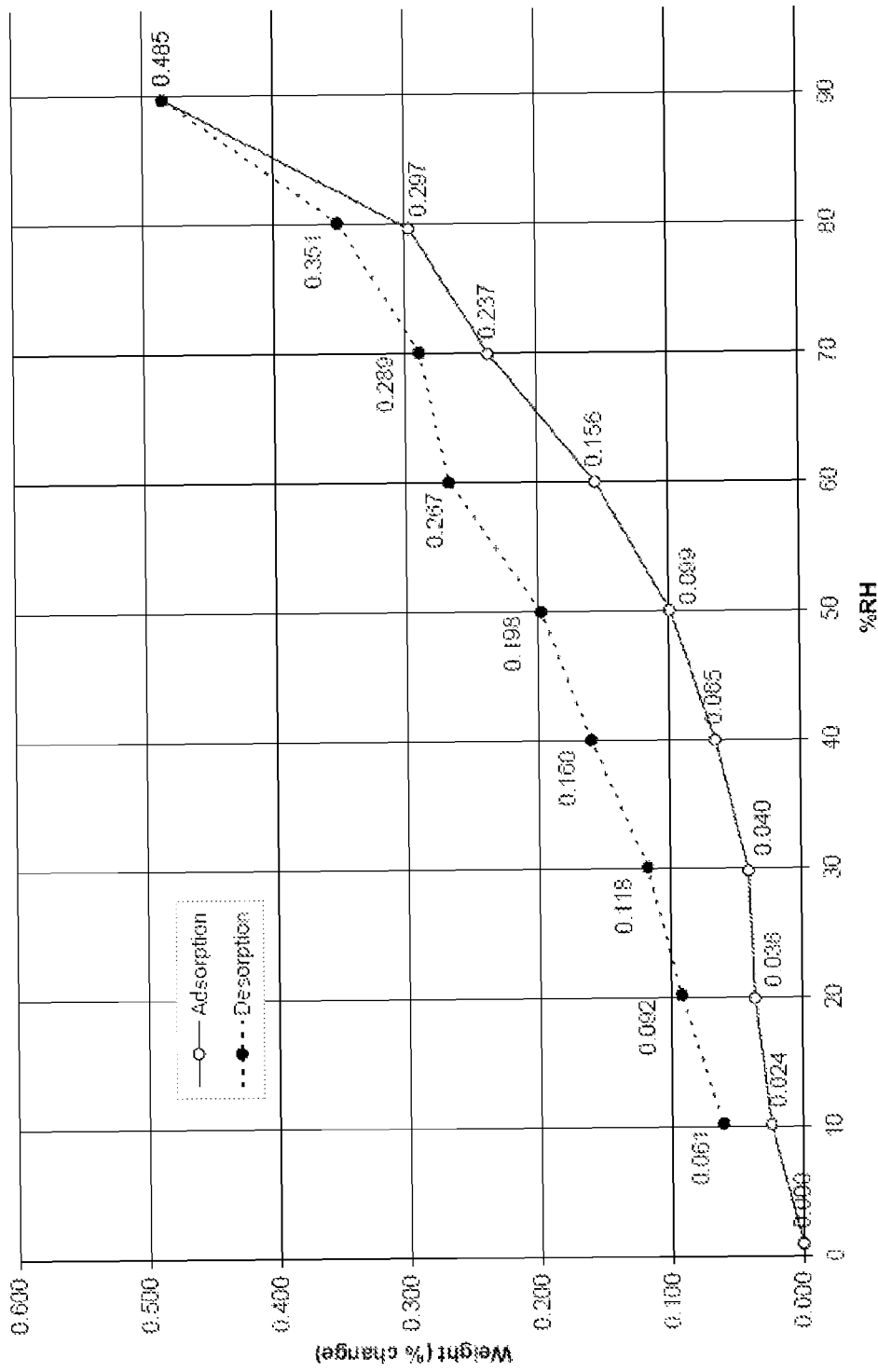
FIG. 3: DMS of Compound 1 (1S)-(+)-10-Camsylate Salt, Form I.

In some embodiments, the Compound 1 (1S)-(+)-10-camsylate salt has a dynamic moisture sorption profile substantially as shown in FIG. 3, wherein by "substantially" is meant that the reported DMS features can vary by about ±5% relative humidity and by about ±5% weight change.

Form I of Compound 1 (1S)-(+)-10-camsylate salt can be prepared by any of the suitable procedures known in the art for preparing crystalline polymorphs. In some embodiments Form I of Compound 1 (1S)-(+)-10-camsylate salt can be prepared as described in Example 1. In some embodiments, Form I of Compound 1 (1S)-(+)-10-camsylate salt can be prepared by slurrying crystalline Compound 1 (1S)-(+)-10-camsylate salt containing one or more crystalline forms other than Form I. In some embodiments, Form I of Compound 1 (1S)-(+)-10-camsylate salt can be prepared by recrystallizing crystalline Compound 1 (1S)-(+)-10-camsylate salt containing one or more crystalline forms other than Form I.

Compound 1 Hemi-L-Malate Salt

One aspect of the present invention pertains to (R)-8-chloro-1-methyl-2,3,4,5-tetrahydro-1H-3-benzazepine hemi-L-malate salt, Form I (Compound 1 hemi-L-malate salt, Form I). The physical properties of Compound 1 hemi-L-malate salt, Form I are summarized in Table 3 below.

TABLE 3

Figure 4:
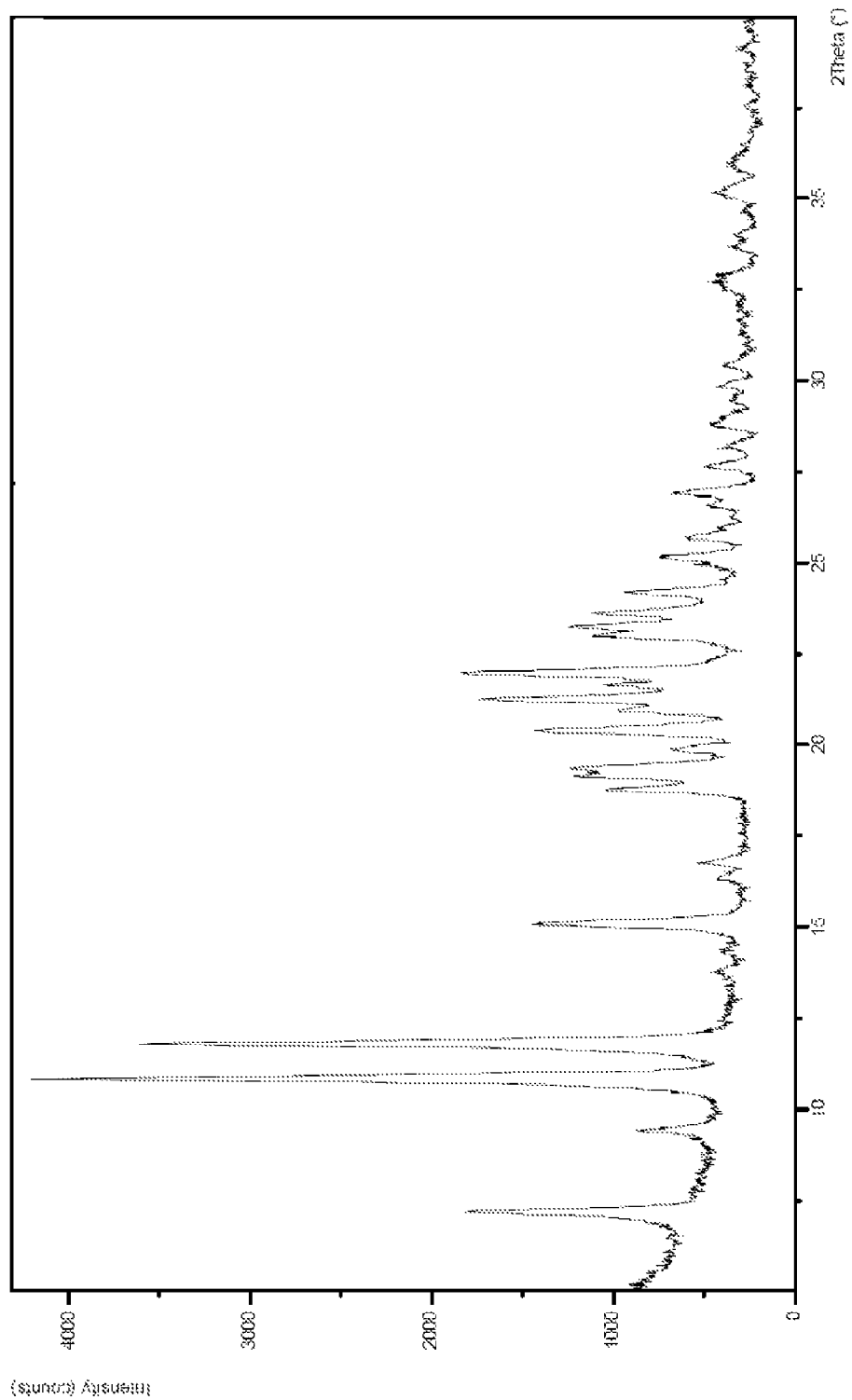
FIG. 4: PXRD of Compound 1 Hemi-L-Malate Salt, Form I.

| | Compound 1 Hemi-L-Malate Salt, Form I |
|---|---|
| PXRD | FIG. 4: Peaks of ≥25% relative intensity at 7.18, 10.84, 11.7932, 15.09, 19.14, 19.36, 20.34, 20.45, 21.26, 21.97, and 23.25 °2θ |
| TGA | FIG. 5: less than 0.3% weight loss up to about 120° C. |
| DSC | FIG. 5: extrapolated onset temperature about 156° C.; enthalpy of fusion 106 J/g |
| DMS | FIG. 6: deliquescence between 80 and 90% RH |

Compound 1 hemi-L-malate salt, Form I was crystalline and melted with an onset temperature of 155-156° C. It demonstrated deliquescence between 80 and 90% RH by DMS analysis.

Certain X-ray powder diffraction peaks for Form I of Compound 1 hemi-L-malate salt are shown in Table 4 below.

TABLE 4

| Pos. (°2θ) | Rel. Int. (%) |
|---|---|
| 7.18 | 33.59 |
| 9.41 | 12.07 |
| 10.84 | 100.00 |
| 11.79 | 88.54 |
| 13.78 | 3.71 |
| 14.34 | 2.76 |
| 15.09 | 31.06 |
| 16.36 | 4.57 |
| 16.77 | 7.82 |
| 18.76 | 21.71 |
| 19.14 | 26.02 |
| 19.36 | 26.41 |
| 19.87 | 11.41 |
| 20.34 | 29.98 |
| 20.45 | 28.55 |
| 20.94 | 19.62 |
| 21.26 | 39.19 |
| 21.64 | 20.60 |
| 21.97 | 42.90 |
| 23.01 | 23.35 |
| 23.25 | 26.66 |
| 23.61 | 23.48 |
| 24.19 | 18.55 |
| 25.16 | 13.20 |
| 25.69 | 9.53 |
| 26.58 | 6.73 |
| 26.92 | 12.21 |
| 27.65 | 7.52 |
| 28.20 | 4.75 |
| 28.81 | 6.71 |
| 29.50 | 3.72 |
| 29.88 | 5.71 |
| 30.43 | 4.91 |
| 32.75 | 6.12 |
| 33.68 | 3.88 |
| 34.02 | 3.72 |
| 35.16 | 6.57 |
| 35.95 | 4.32 |
| 36.85 | 1.25 |
| 37.53 | 1.99 |
| 38.11 | 1.54 |
| 39.1250 | 2.61 |

One aspect of the present invention is directed to a Compound 1 hemi-L-malate salt having an X-ray powder diffraction pattern comprising a peak, in terms of 2θ, at about 10.84°. In some embodiments, the crystalline form has an X-ray powder diffraction pattern comprising a peak, in terms of 2θ, at about 11.7932°. In some embodiments, the crystalline form has an X-ray powder diffraction pattern comprising peaks, in terms of 2θ, at about 10.84° and about 11.7932°. In some embodiments, the crystalline form has an X-ray powder diffraction pattern comprising peaks, in terms of 2θ, at about 10.84° and about 21.97°. In some embodiments, the crystalline form has an X-ray powder diffraction pattern comprising peaks, in terms of 2θ, at about 10.84°, about 11.7932°, and about 21.97°. In some embodiments, the crystalline form has an X-ray powder diffraction pattern comprising peaks, in terms of 2θ, at about 10.84°, about 11.7932°, about 21.97°, about 21.26°, about 7.18°, about 15.09°, and about 20.34°. In some embodiments, the crystalline form has an X-ray powder diffraction pattern comprising peaks, in terms of 2θ, at about 10.84°, about 11.7932°, about 21.97°, about 21.26°, about 7.18°, about 15.09°, about 20.34°, about 20.45°, about 23.25°, and about 19.36°. One aspect of the present invention is directed to a Compound 1 hemi-L-malate salt having an X-ray powder diffraction pattern comprising one or more peaks listed in Table 4. In some embodiments, the crystalline form has an X-ray powder diffraction pattern substantially as shown in FIG. 4, wherein by "substantially" is meant that the reported peaks can vary by about ±0.2° 2θ, and also that the relative intensities of the reported peaks can vary.

In some embodiments, the Compound 1 hemi-L-malate salt has a differential scanning calorimetry thermogram comprising an endotherm with an extrapolated onset temperature between about 140° C. and about 170° C. In some embodiments, the Compound 1 hemi-L-malate salt has a differential scanning calorimetry thermogram comprising an endotherm with an extrapolated onset temperature at about 156° C. In some embodiments, the Compound 1 hemi-L-malate salt has a differential scanning calorimetry thermogram comprising an endotherm with an associated heat flow of about 106 joules per gram. In some embodiments, the Compound 1 hemi-L-malate salt has a thermogravimetric analysis profile substantially as shown in FIG. 5, wherein by "substantially" is meant that the reported TGA features can vary by about ±5° C. and by about ±2% weight change.

Figure 5:
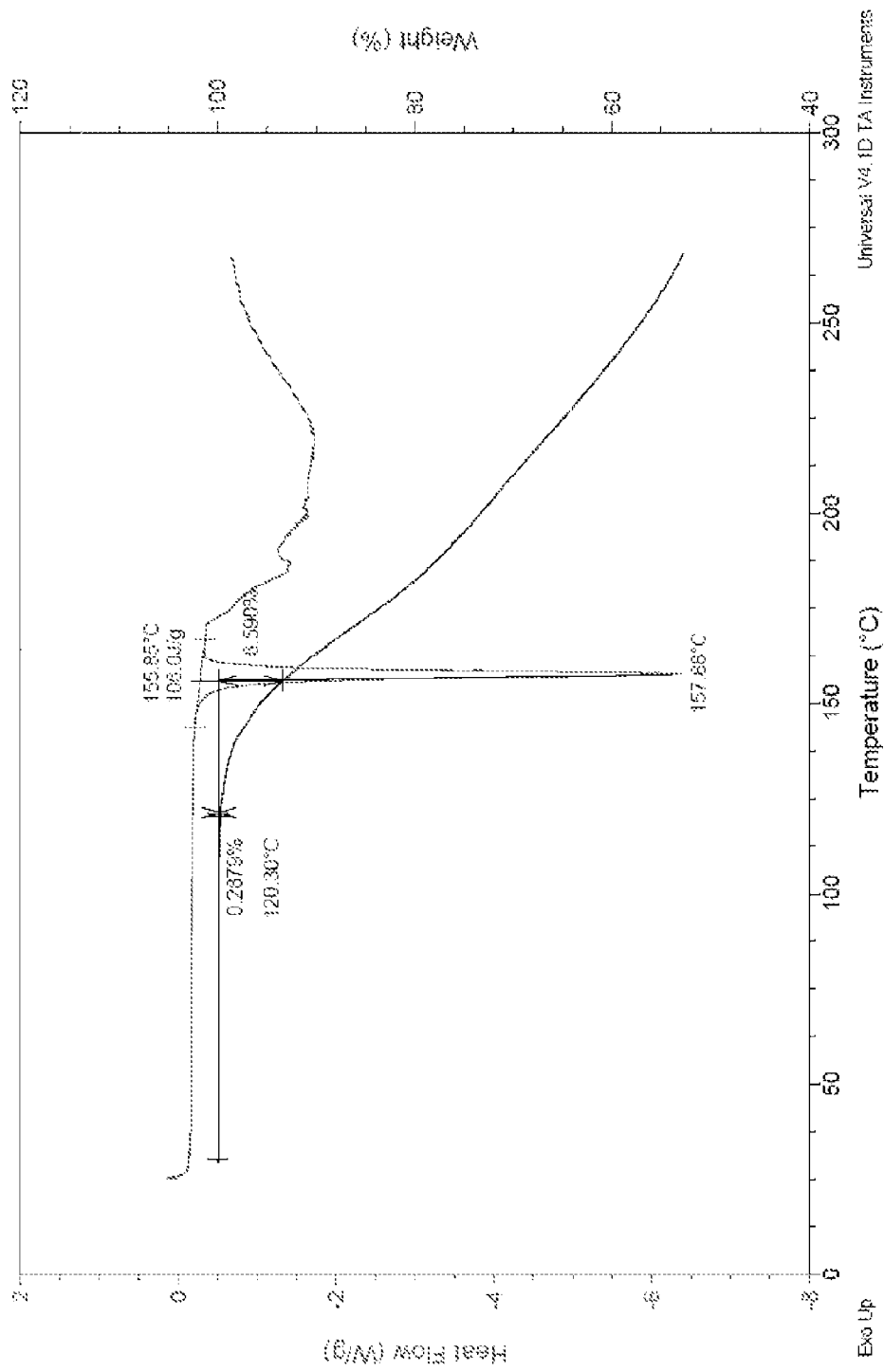
FIG. 5: DSC and TGA of Compound 1 Hemi-L-Malate Salt, Form I.

In some embodiments, the Compound 1 hemi-L-malate salt has a differential scanning calorimetry thermogram substantially as shown in FIG. 5, wherein by "substantially" is meant that the reported DSC features can vary by about ±6° C. and by about ±20 joules per gram.

Figure 6:
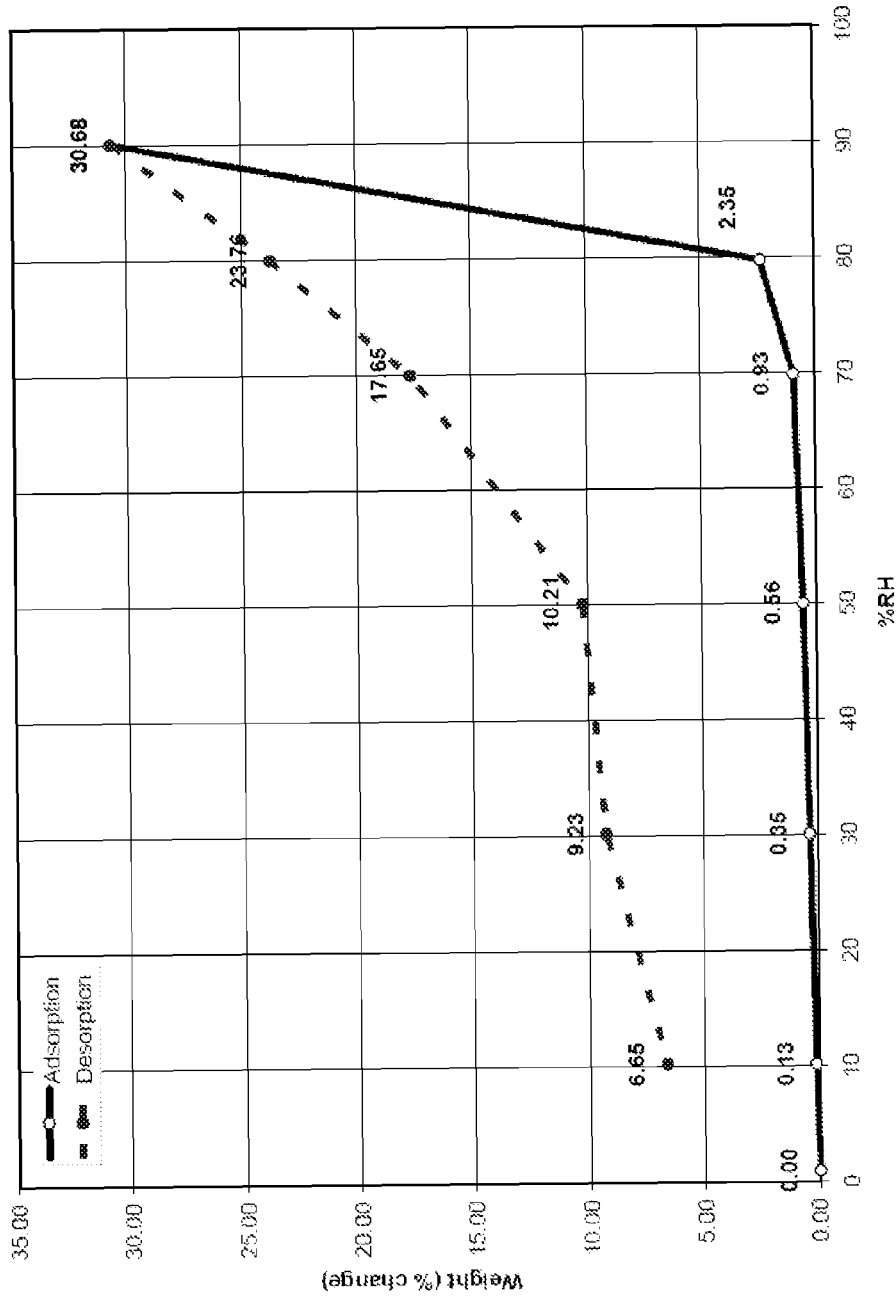
FIG. 6: DMS of Compound 1 Hemi-L-Malate Salt, Form I.

In some embodiments, the Compound 1 hemi-L-malate salt has a dynamic moisture sorption profile substantially as shown in FIG. 6, wherein by "substantially" is meant that the reported DMS features can vary by about ±5% relative humidity and by about ±5% weight change.

Form I of Compound 1 hemi-L-malate salt can be prepared by any of the suitable procedures known in the art for preparing crystalline polymorphs. In some embodiments Form I of Compound 1 hemi-L-malate salt can be prepared as described in Example 2. In some embodiments, Form I of Compound 1 hemi-L-malate salt can be prepared by slurrying crystalline Compound 1 hemi-L-malate salt containing one or more crystalline forms other than Form I. In some embodiments, Form I of Compound 1 hemi-L-malate salt can be prepared by recrystallizing crystalline Compound 1 hemi-L-malate salt containing one or more crystalline forms other than Form I.

Compound 1 L-Glutamate Salt

One aspect of the present invention pertains to a (R)-8-chloro-1-methyl-2,3,4,5-tetrahydro-1H-3-benzazepine L-glutamate salt (Compound 1 L-glutamate salt). In some embodiments, the (R)-8-chloro-1-methyl-2,3,4,5-tetrahydro-1H-3-benzazepine L-glutamate salt is Form I (Compound 1 L-glutamate salt, Form I). The physical properties of Form I of Compound 1 L-glutamate salt are summarized in Table 5 below.

TABLE 5

Figure 7:
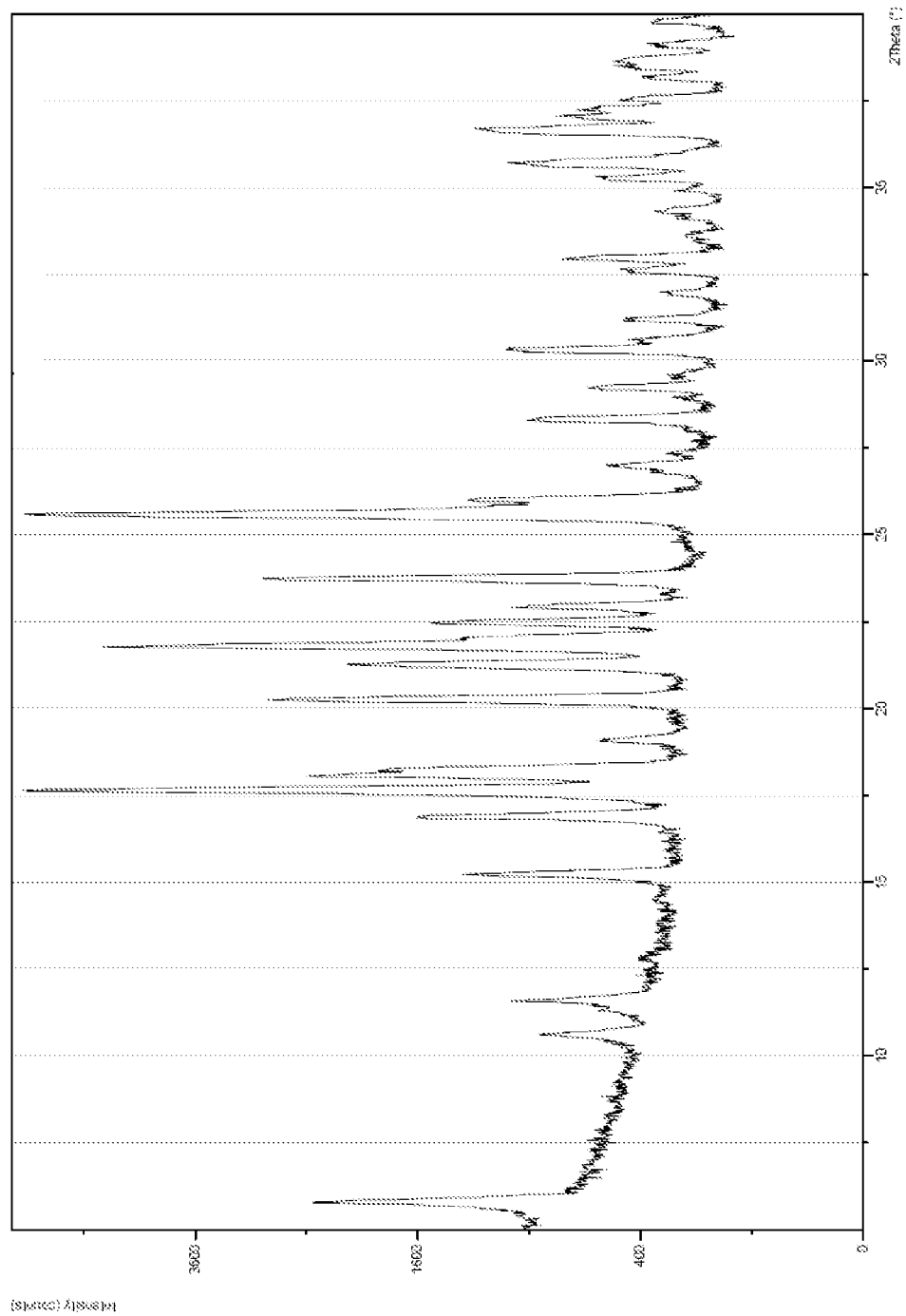
FIG. 7: PXRD of Compound 1 L-Glutamate Salt, Form I.

| Compound 1 L-Glutamate Salt, Form I | |
|---|---|
| PXRD | FIG. 7: Peaks of ≥20% relative intensity at 5.79, 16.88, 17.63, 18.06, 18.24, 20.25, 21.27, 21.78, 22.46, 23.73, and 25.59 °2θ |
| TGA | FIG. 8: about 0.25% weight loss up to about 124° C. |
| DSC | FIG. 8: extrapolated onset temperature about 187° C.; enthalpy of fusion 288 J/g |
| DMS | FIG. 9: non-hygroscopic, about 0.1% weight gain out 90% RH |

Compound 1 L-glutamate salt, Form I had a melting onset of 187° C. A large portion of the salt, a degradant or component, was lost prior to melting, based on the TGA result. The salt was anhydrous and non-hygroscopic.

Certain X-ray powder diffraction peaks for Form I of Compound 1 L-glutamate salt are shown in Table 6 below.

TABLE 6

| Pos. (°2θ) | Rel. Int. (%) |
|---|---|
| 5.79 | 31.50 |
| 10.61 | 8.24 |
| 11.59 | 10.80 |
| 12.83 | 1.38 |
| 15.22 | 17.13 |
| 16.88 | 24.59 |
| 17.63 | 99.12 |
| 18.06 | 41.01 |
| 18.24 | 29.49 |
| 19.07 | 5.69 |
| 20.25 | 47.15 |
| 21.27 | 34.93 |
| 21.78 | 80.76 |
| 22.46 | 23.35 |
| 22.92 | 13.91 |
| 23.73 | 49.50 |
| 25.59 | 100.00 |
| 26.00 | 19.27 |
| 26.98 | 5.80 |
| 27.36 | 2.03 |
| 28.32 | 13.14 |
| 28.94 | 2.08 |
| 29.2382 | 7.91 |
| 29.5508 | 2.11 |
| 30.2671 | 13.89 |
| 30.6035 | 4.84 |
| 31.20 | 5.22 |
| 31.96 | 2.89 |
| 32.61 | 5.41 |
| 32.94 | 10.36 |
| 33.62 | 1.96 |
| 34.31 | 3.53 |
| 34.93 | 2.03 |
| 35.24 | 7.29 |
| 35.60 | 11.62 |
| 36.66 | 18.40 |
| 37.03 | 10.33 |
| 37.25 | 8.52 |
| 37.54 | 5.74 |
| 38.17 | 4.11 |
| 38.49 | 5.75 |
| 38.76 | 4.61 |
| 39.10 | 3.60 |

One aspect of the present invention is directed to a Compound 1 L-glutamate salt having an X-ray powder diffraction pattern comprising a peak, in terms of 2θ, at about 25.59°. In some embodiments, the crystalline form has an X-ray powder diffraction pattern comprising a peak, in terms of 2θ, at about 17.63°. In some embodiments, the crystalline form has an X-ray powder diffraction pattern comprising peaks, in terms of 2θ, at about 25.59° and about 17.63°. In some embodiments, the crystalline form has an X-ray powder diffraction pattern comprising peaks, in terms of 2θ, at about 25.59° and about 21.78°. In some embodiments, the crystalline form has an X-ray powder diffraction pattern comprising peaks, in terms of 2θ, at about 25.59°, about 17.63°, and about 21.78°. In some embodiments, the crystalline form has an X-ray powder diffraction pattern comprising peaks, in terms of 2θ, at about 25.59°, about 17.63°, about 21.78°, about 23.73°, about 20.25°, about 18.06°, and about 21.27°. In some embodiments, the crystalline form has an X-ray powder diffraction pattern comprising peaks, in terms of 2θ, at about 25.59°, about 17.63°, about 21.78°, about 23.73°, about 20.25°, about 18.06°, about 21.27°, about 5.79°, about 18.24°, and about 16.88°. One aspect of the present invention is directed to a Compound 1 L-glutamate salt having an X-ray powder diffraction pattern comprising one or more peaks listed in Table 6. In some embodiments, the crystalline form has an X-ray powder diffraction pattern substantially as shown in FIG. 7, wherein by "substantially" is meant that the reported peaks can vary by about ±0.2° 2θ, and also that the relative intensities of the reported peaks can vary.

In some embodiments, the Compound 1 L-glutamate salt has a differential scanning calorimetry thermogram comprising an endotherm with an extrapolated onset temperature between about 170° C. and about 200° C. In some embodiments, the Compound 1 L-glutamate salt has a differential scanning calorimetry thermogram comprising an endotherm with an extrapolated onset temperature at about 187° C. In some embodiments, the Compound 1 L-glutamate salt has a differential scanning calorimetry thermogram comprising an endotherm with an associated heat flow of about 288 joules per gram. In some embodiments, the Compound 1 L-glutamate salt has a thermogravimetric analysis profile substantially as shown in FIG. 8, wherein by "substantially" is meant that the reported TGA features can vary by about ±5° C. and by about ±2% weight change.

Figure 8:
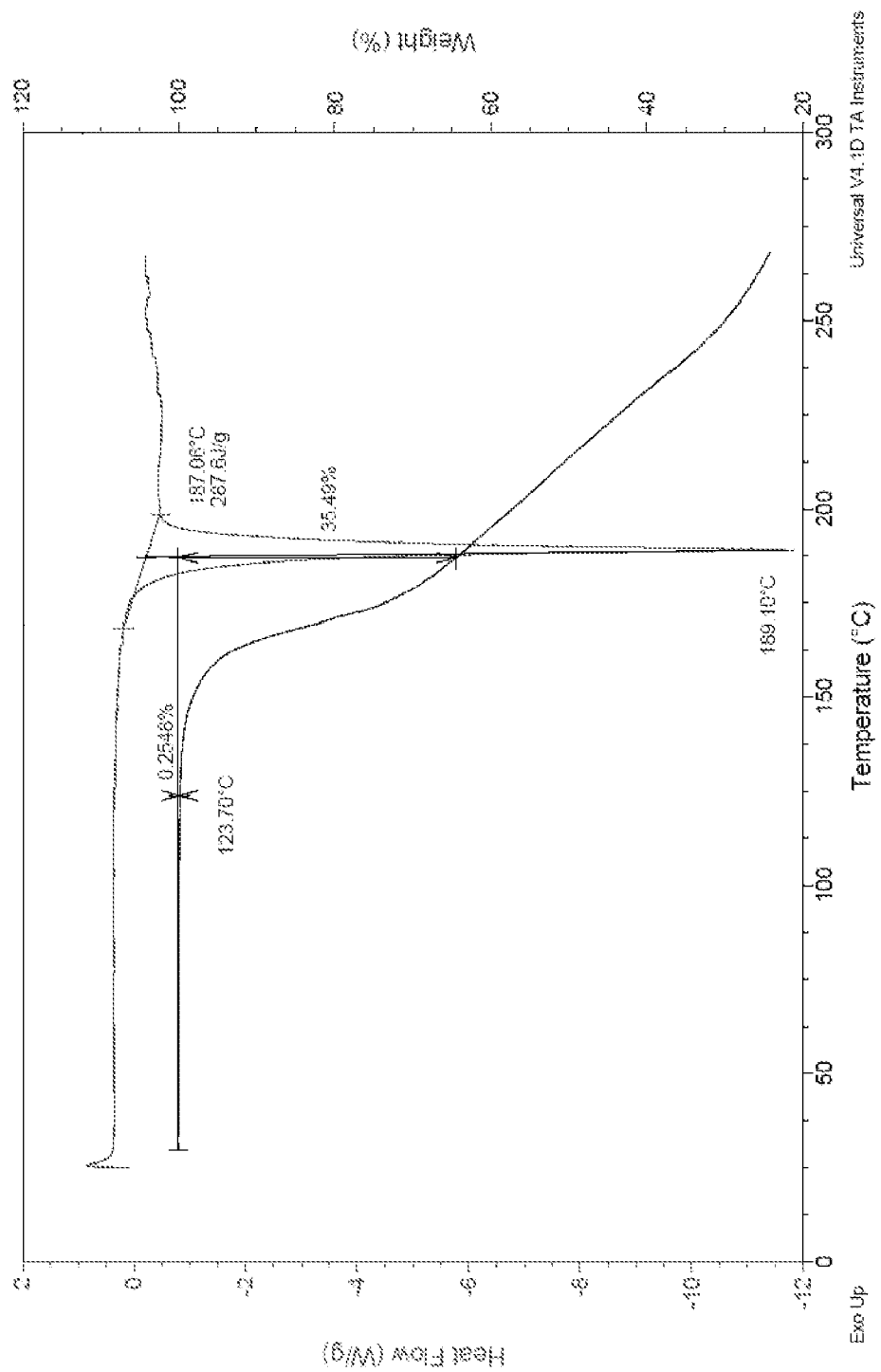
FIG. 8: DSC and TGA of Compound 1 L-Glutamate Salt, Form I.

In some embodiments, the Compound 1 L-glutamate salt has a differential scanning calorimetry thermogram substantially as shown in FIG. 8, wherein by "substantially" is meant that the reported DSC features can vary by about ±6° C. and by about ±20 joules per gram.

Figure 9:
FIG. 9: DMS of Compound 1 L-Glutamate Salt, Form I.

In some embodiments, the Compound 1 L-glutamate salt has a dynamic moisture sorption profile substantially as shown in FIG. 9. By "substantially" is meant that the reported DMS features can vary by about ±5% relative humidity and by about ±5% weight change.

Form I of Compound 1 L-glutamate salt can be prepared by any of the suitable procedures known in the art for preparing crystalline polymorphs. In some embodiments Form I of Compound 1 L-glutamate salt can be prepared as described in Example 3. In some embodiments, Form I of Compound 1 L-glutamate salt can be prepared by slurrying crystalline Compound 1 L-glutamate salt containing one or more crystalline forms other than Form I. In some embodiments, Form I of Compound 1 L-glutamate salt can be prepared by recrystallizing crystalline Compound 1 L-glutamate salt containing one or more crystalline forms other than Form I.

Compound 1 L-Aspartate Salt

One aspect of the present invention pertains to (R)-8-chloro-1-methyl-2,3,4,5-tetrahydro-1H-3-benzazepine L-aspartate salt, Form I (Compound 1 L-aspartate salt, Form I). The physical properties of Compound 1 L-aspartate salt, Form I are summarized in Table 7 below.

TABLE 7

Figure 10:
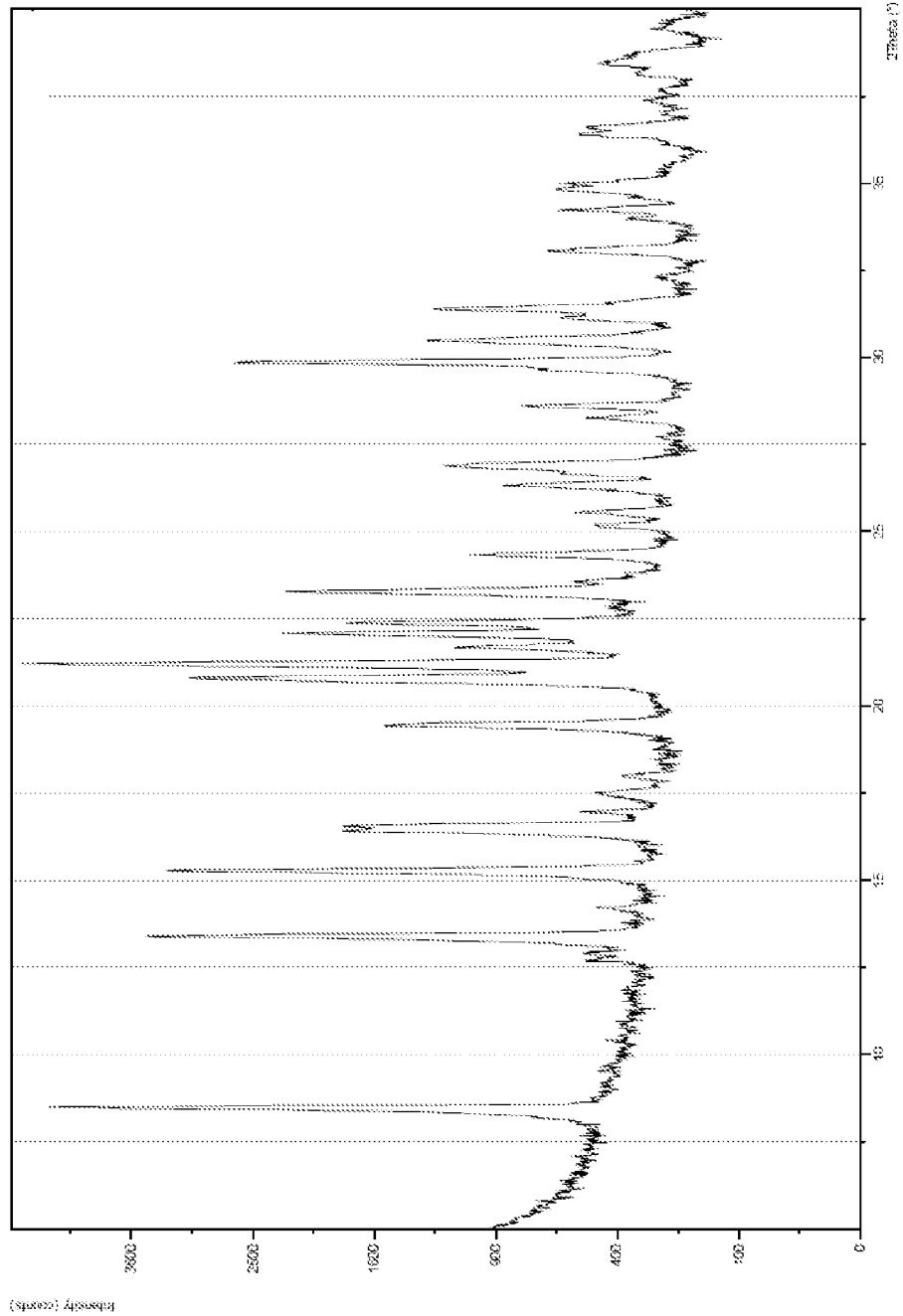
FIG. 10: PXRD of Compound 1 L-Aspartate Salt, Form I.

| | Compound 1 L-Aspartate Salt, Form I |
|---|---|
| PXRD | FIG. 10: Peaks of ≥25% relative intensity at 8.49, 13.40, 15.28, 16.43, 16.55, 19.45, 20.80, 21.22, 22.08, 22.38, 23.29, and 29.85 °2θ |
| TGA | FIG. 11: 54.9% weight from about 140° C. to about 200° C. |
| DSC | FIG. 11: extrapolated onset temperature about 174° C. |
| DMS | FIG. 12: hygroscopic at 70% RH and deliquescent above 70% RH |

Form I of Compound 1 L-aspartate salt was an anhydrous crystal phase that melted at 173.9° C. It displayed back-to-back endothermic events corresponding to simultaneous loss of a degradant or a component of the salt, and melting. The TGA showed a large step transition (weight-loss), thus DSC endothermic events are accompanied by volatilization of some portion of the sample.

DMS showed it to be slightly hygroscopic at 70% RH and deliquescent above 70% RH, picking up 28% weight during the 80% RH hold, 45% of its weight in water out to and including the 90% RH hold at 25° C.

Certain X-ray powder diffraction peaks for Form I of Compound 1 L-aspartate salt are shown in Table 8 below.

TABLE 8

| Pos. (°2θ) | Rel. Int. (%) |
|---|---|
| 5.12 | 1.93 |
| 8.49 | 89.49 |
| 12.75 | 4.03 |
| 13.40 | 71.47 |
| 14.20 | 4.37 |
| 15.28 | 68.22 |
| 16.43 | 35.18 |
| 16.55 | 35.20 |
| 16.96 | 6.96 |
| 17.49 | 5.41 |
| 17.98 | 3.56 |
| 19.45 | 29.32 |
| 20.80 | 64.93 |
| 21.22 | 100.00 |
| 21.69 | 20.38 |
| 22.08 | 45.99 |
| 22.38 | 36.19 |
| 23.29 | 45.28 |
| 23.56 | 7.19 |
| 24.33 | 17.79 |
| 25.18 | 6.08 |
| 25.56 | 7.58 |
| 26.33 | 15.10 |
| 26.66 | 9.03 |
| 26.88 | 21.72 |
| 27.71 | 1.47 |
| 28.27 | 7.21 |
| 28.60 | 13.17 |
| 29.85 | 56.07 |
| 30.49 | 24.42 |
| 31.14 | 9.83 |
| 31.38 | 24.01 |
| 32.29 | 2.26 |
| 33.06 | 11.70 |
| 33.98 | 4.21 |
| 34.23 | 10.10 |
| 34.82 | 10.62 |
| 35.02 | 8.80 |
| 36.40 | 8.61 |
| 36.60 | 8.18 |
| 37.01 | 2.54 |
| 37.35 | 3.76 |
| 37.67 | 2.82 |
| 38.13 | 4.28 |
| 38.43 | 7.61 |
| 38.74 | 4.65 |
| 39.43 | 3.29 |

One aspect of the present invention is directed to a Compound 1 L-aspartate salt having an X-ray powder diffraction pattern comprising a peak, in terms of 2θ, at about 21.22°. In some embodiments, the crystalline form has an X-ray powder diffraction pattern comprising a peak, in terms of 2θ, at about 8.49°. In some embodiments, the crystalline form has an X-ray powder diffraction pattern comprising peaks, in terms of 2θ, at about 21.22° and about 8.49°. In some embodiments, the crystalline form has an X-ray powder diffraction pattern comprising peaks, in terms of 2θ, at about 21.22° and about 13.40°. In some embodiments, the crystalline form has an X-ray powder diffraction pattern comprising peaks, in terms of 2θ, at about 21.22°, about 8.49°, and about 13.40°. In some embodiments, the crystalline form has an X-ray powder diffraction pattern comprising peaks, in terms of 2θ, at about 21.22°, about 8.49°, about 13.40°, about 15.28°, about 29.85°, about 29.85°, and about 22.08°. In some embodiments, the crystalline form has an X-ray powder diffraction pattern comprising peaks, in terms of 2θ, at about 21.22°, about 8.49°, about 13.40°, about 15.28°, about 29.85°, about 29.85°, about 22.08°, about 23.29°, about 22.38°, and about 16.55°. One aspect of the present invention is directed to a Compound 1 L-aspartate salt having an X-ray powder diffraction pattern comprising one or more peaks listed in Table 8. In some embodiments, the crystalline form has an X-ray powder diffraction pattern substantially as shown in FIG. 10, wherein by "substantially" is meant that the reported peaks can vary by about ±0.2° 2θ, and also that the relative intensities of the reported peaks can vary.

In some embodiments, the Compound 1 L-aspartate salt has a differential scanning calorimetry thermogram comprising an endotherm with an extrapolated onset temperature between about 160° C. and about 190° C. In some embodiments, the Compound 1 L-aspartate salt has a differential scanning calorimetry thermogram comprising an endotherm with an extrapolated onset temperature at about 174° C. In some embodiments, the Compound 1 L-aspartate salt has a thermogravimetric analysis profile substantially as shown in FIG. 11, wherein by "substantially" is meant that the reported TGA features can vary by about ±5° C. and by about ±2% weight change.

Figure 11:
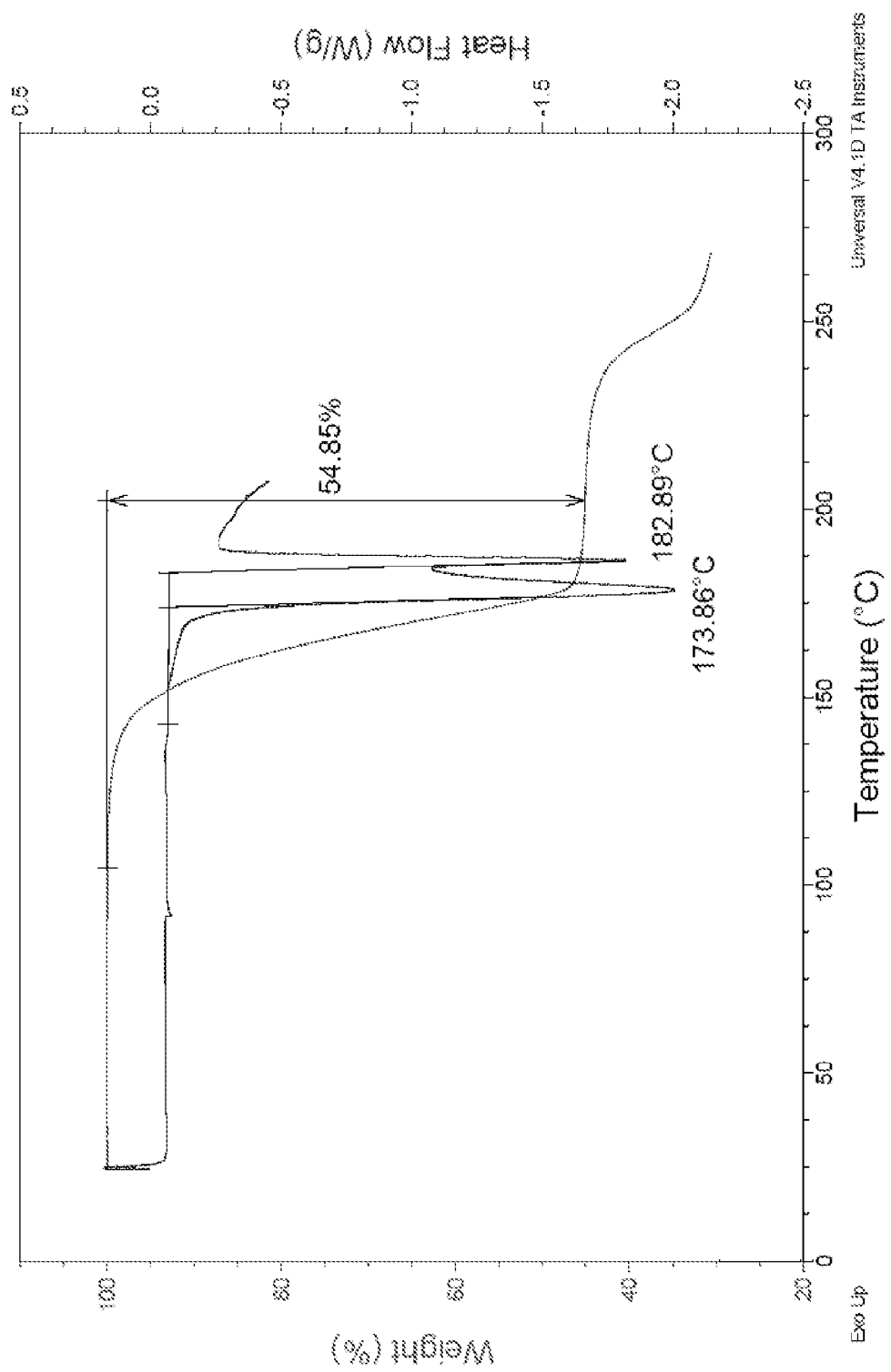
FIG. 11: DSC and TGA of Compound 1 L-Aspartate Salt, Form I.

In some embodiments, the Compound 1 L-aspartate salt has a differential scanning calorimetry thermogram substantially as shown in FIG. 11, wherein by "substantially" is meant that the reported DSC features can vary by about ±6° C. and by about ±20 joules per gram.

Figure 12:
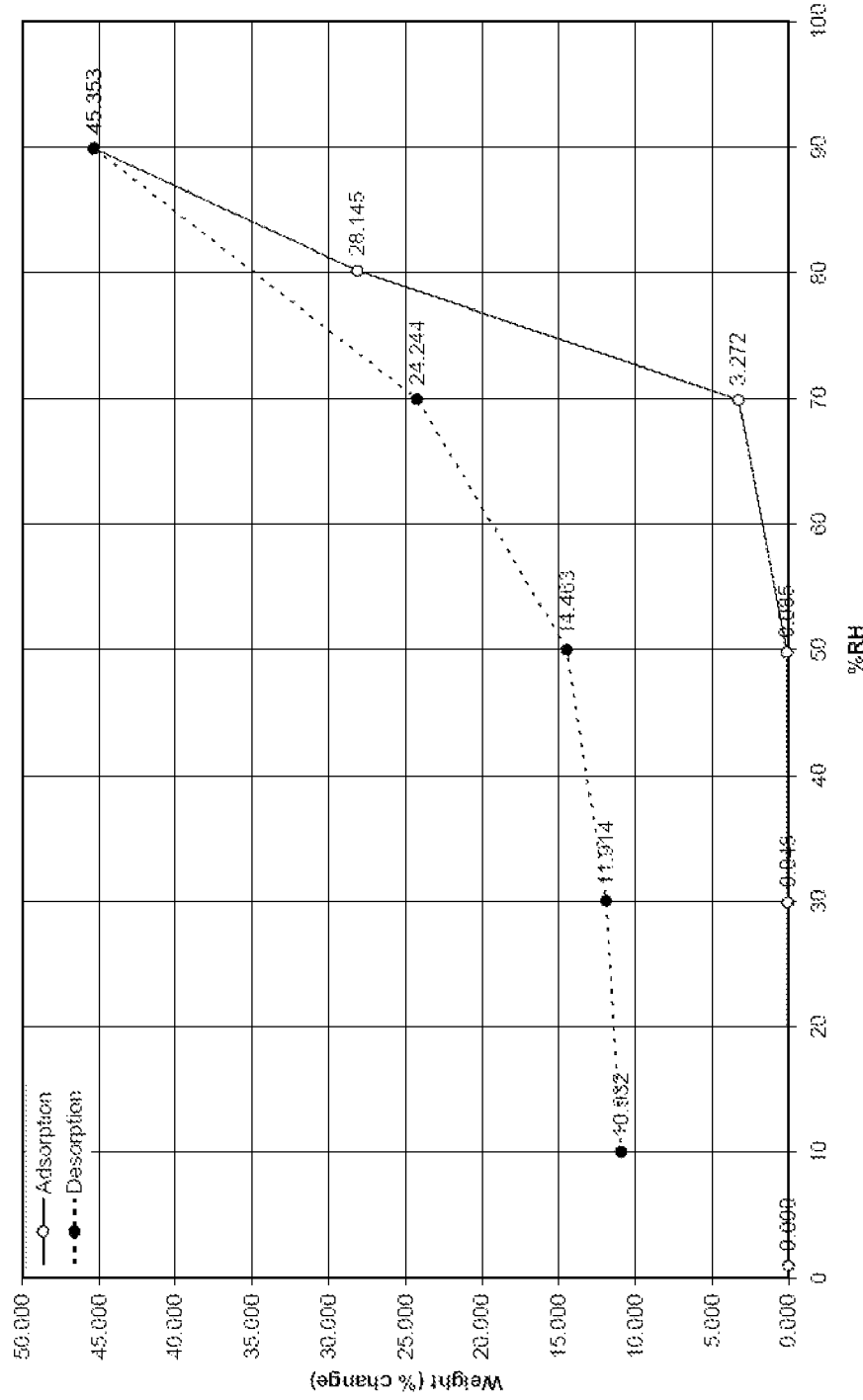
FIG. 12: DMS of Compound 1 L-Aspartate Salt, Form I.

In some embodiments, the Compound 1 L-aspartate salt has a dynamic moisture sorption profile substantially as shown in FIG. 12, wherein by "substantially" is meant that the reported DMS features can vary by about ±5% relative humidity and by about ±5% weight change.

Form I of Compound 1 L-aspartate salt can be prepared by any of the suitable procedures known in the art for preparing crystalline polymorphs. In some embodiments Form I of Compound 1 L-aspartate salt can be prepared as described in Example 4. In some embodiments, Form I of Compound 1 L-aspartate salt can be prepared by slurrying crystalline Compound 1 L-aspartate salt containing one or more crystalline forms other than Form I. In some embodiments, Form I of Compound 1 L-aspartate salt can be prepared by recrystallizing crystalline Compound 1 L-aspartate salt containing one or more crystalline forms other than Form I.

Compound 1 Hemimucate Salt.

One aspect of the present invention pertains to (R)-8-chloro-1-methyl-2,3,4,5-tetrahydro-1H-3-benzazepine hemimucate, Form I (Compound 1 hemimucate salt, Form I). The physical properties of Compound 1 hemimucate salt, Form I are summarized in Table 9 below.

TABLE 9

Figure 13:
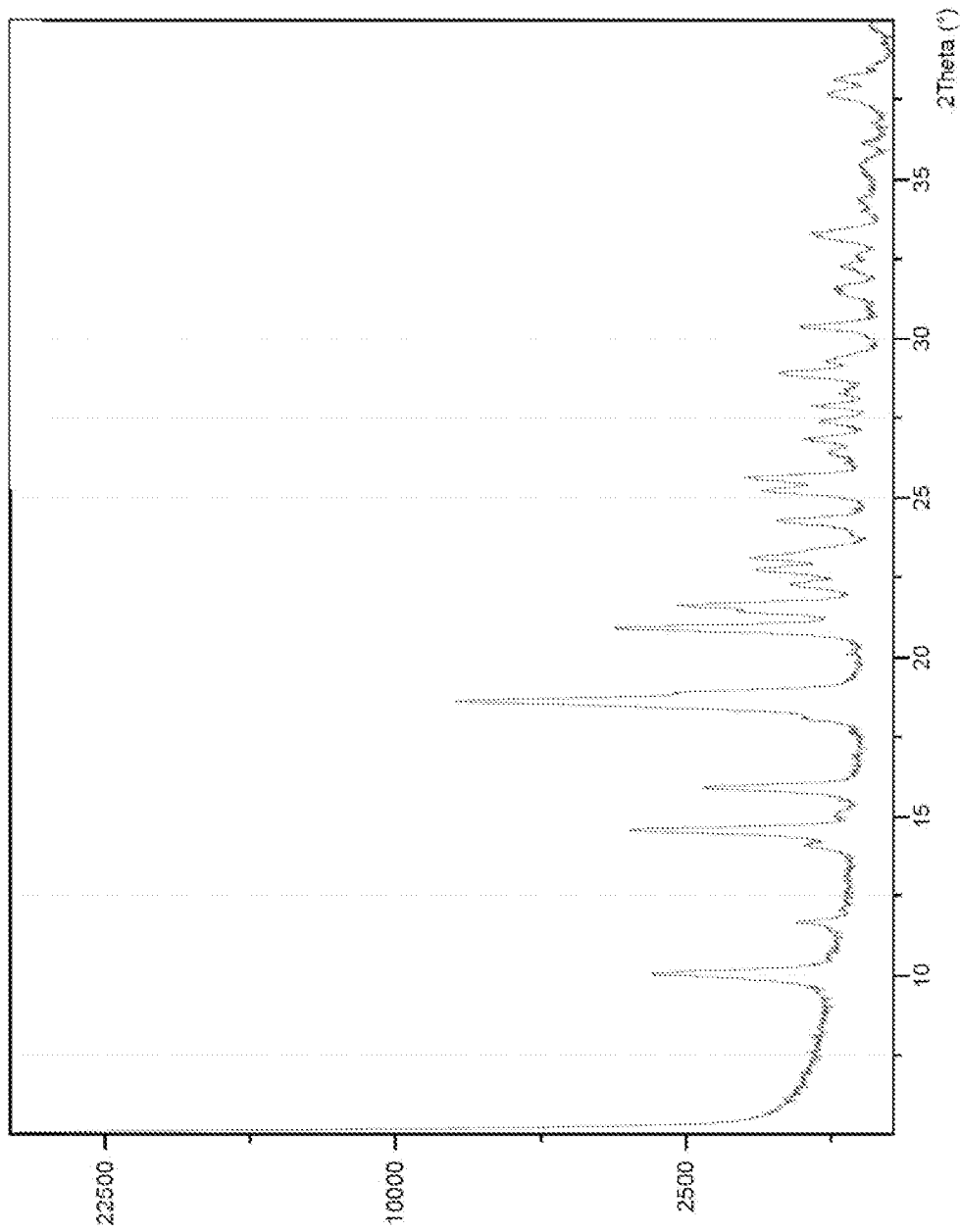
FIG. 13: PXRD of Compound 1 Hemimucate Salt, Form I.

| | Compound 1 Hemimucate Salt, Form I |
|---|---|
| PXRD | FIG. 13: Peaks of >4% relative intensity at 5.06, 10.06, 14.57, 15.90, 18.60, 18.89, 20.92, 21.46, 21.63, 22.74, 23.0980, and 25.61 °2θ |
| TGA | FIG. 14: 56% weight loss from about 175° C. to about 215° C. |
| DSC | FIG. 14: extrapolated onset temperature: 208° C.; enthalpy of fusion 358 J/g |
| DMS | FIG. 15: 0.255% weight increase out to 90% RH |

Form I of Compound 1 hemimucate salt exhibited a melting onset at 208° C. The large heat of fusion (357.5 J/g shown in FIG. 14) was due in large part to vaporization of more than half of the sample, indicating the salt melts with degradation.

Compound 1 hemimucate salt was essentially non-hygroscopic, picking up only 0.26% weight in water out to and including the 90% RH hold at 25° C.

Certain X-ray powder diffraction peaks for Form I of Compound 1 hemimucate salt are shown in Table 10 below.

TABLE 10

| Pos. (°2θ) | Rel. Int. (%) |
|---|---|
| 5.06 | 100.00 |
| 10.06 | 9.14 |
| 10.62 | 0.26 |
| 11.67 | 1.51 |
| 12.08 | 0.05 |
| 14.08 | 1.50 |
| 14.57 | 11.53 |
| 15.07 | 0.53 |
| 15.90 | 6.75 |
| 18.01 | 1.55 |
| 18.60 | 28.58 |
| 18.89 | 8.11 |
| 20.12 | 0.24 |
| 20.92 | 13.14 |
| 21.46 | 4.96 |
| 21.63 | 8.25 |
| 22.29 | 2.45 |
| 22.74 | 4.12 |
| 23.10 | 4.24 |
| 23.86 | 0.41 |
| 24.27 | 3.09 |
| 25.22 | 3.81 |
| 25.61 | 4.48 |
| 26.44 | 1.12 |
| 26.85 | 1.86 |
| 27.37 | 1.54 |
| 27.88 | 1.72 |
| 28.29 | 0.75 |
| 28.92 | 3.11 |
| 29.28 | 1.36 |
| 30.37 | 2.29 |
| 31.44 | 1.06 |
| 31.60 | 1.04 |
| 32.29 | 0.96 |
| 32.64 | 0.49 |
| 33.30 | 1.90 |
| 34.00 | 0.39 |
| 34.40 | 0.59 |
| 35.18 | 0.40 |
| 35.42 | 0.52 |
| 36.17 | 0.39 |
| 36.78 | 0.21 |
| 37.65 | 1.54 |
| 38.12 | 1.29 |
| 38.51 | 0.37 |

One aspect of the present invention is directed to a Compound 1 hemimucate salt having an X-ray powder diffraction pattern comprising a peak, in terms of 2θ, at about 5.06°. In some embodiments, the crystalline form has an X-ray powder diffraction pattern comprising a peak, in terms of 2θ, at about 18.60°. In some embodiments, the crystalline form has an X-ray powder diffraction pattern comprising peaks, in terms of 2θ, at about 5.06° and about 18.60°. In some embodiments, the crystalline form has an X-ray powder diffraction pattern comprising peaks, in terms of 2θ, at about 5.06° and about 20.92°. In some embodiments, the crystalline form has an X-ray powder diffraction pattern comprising peaks, in terms of 2θ, at about 5.06°, about 18.60°, and about 20.92°. In some embodiments, the crystalline form has an X-ray powder diffraction pattern comprising peaks, in terms of 2θ, at about 5.06°, about 18.60°, about 20.92°, about 14.57°, about 10.06°, about 21.63°, and about 18.89°. In some embodiments, the crystalline form has an X-ray powder diffraction pattern comprising peaks, in terms of 2θ, at about 5.06°, about 18.60°, about 20.92°, about 14.57°, about 10.06°, about 21.63°, about 18.89°, about 15.90°, about 21.46°, and about 25.61°. One aspect of the present invention is directed to a Compound 1 hemimucate salt having an X-ray powder diffraction pattern comprising one or more peaks listed in Table 10. In some embodiments, the crystalline form has an X-ray powder diffraction pattern substantially as shown in FIG. 13, wherein by "substantially" is meant that the reported peaks can vary by about ±0.2° 2θ, and also that the relative intensities of the reported peaks can vary.

In some embodiments, the Compound 1 hemimucate salt has a differential scanning calorimetry thermogram comprising an endotherm with an extrapolated onset temperature between about 190° C. and about 220° C. In some embodiments, the Compound 1 hemimucate salt has a differential scanning calorimetry thermogram comprising an endotherm with an extrapolated onset temperature at about 208° C. In some embodiments, the Compound 1 hemimucate salt has a differential scanning calorimetry thermogram comprising an endotherm with an associated heat flow of about 358 joules per gram. In some embodiments, the Compound 1 hemimucate salt has a differential scanning calorimetry thermogram substantially as shown in FIG. 14, wherein by "substantially" is meant that the reported DSC features can vary by about ±6° C. and by about ±20 joules per gram.

Figure 14:
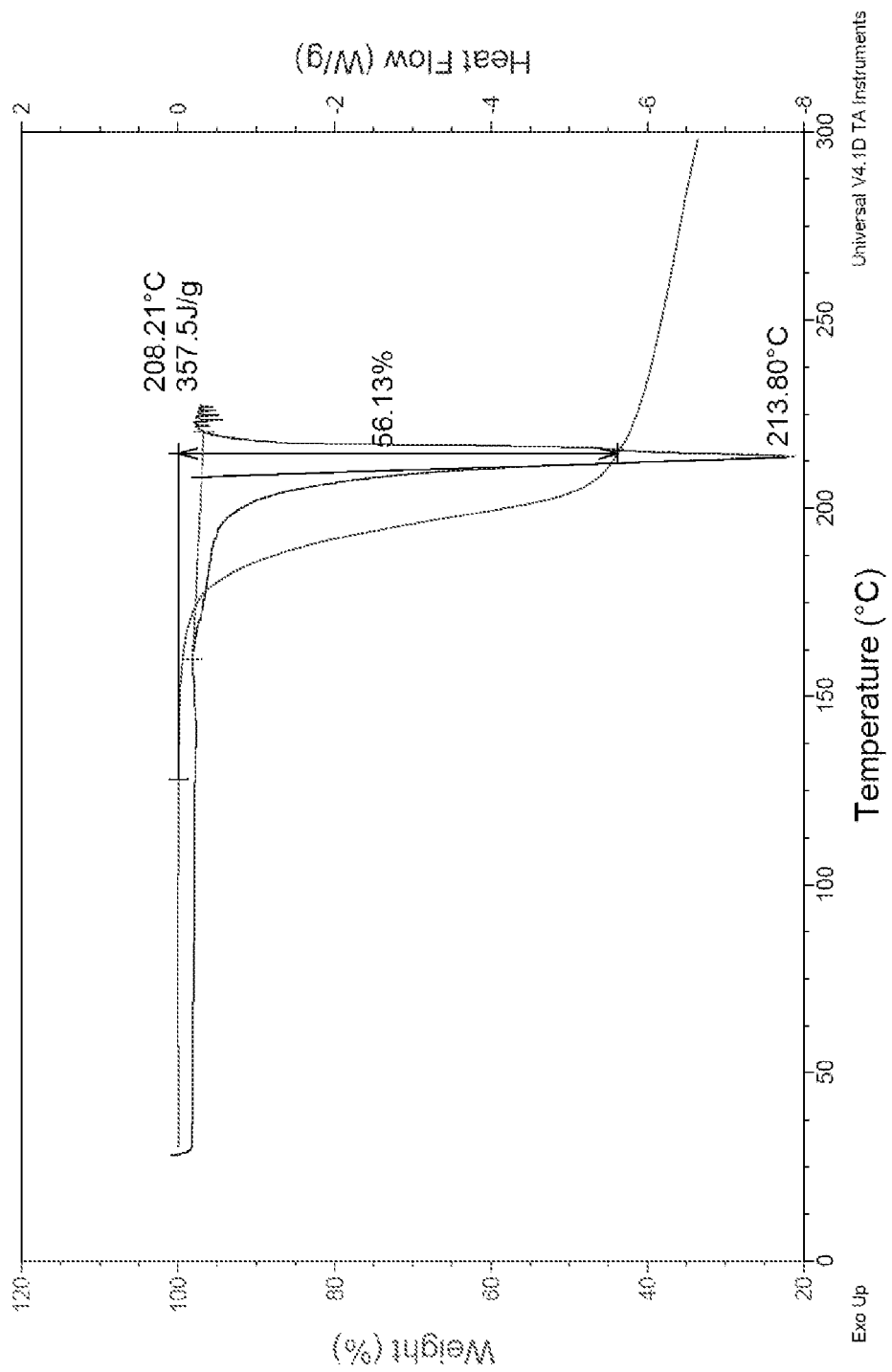
FIG. 14: DSC and TGA of Compound 1 Hemimucate Salt, Form I.

In some embodiments, the Compound 1 hemimucate salt has a thermogravimetric analysis profile substantially as shown in FIG. 14, wherein by "substantially" is meant that the reported TGA features can vary by about ±5° C. and by about ±2% weight change.

Figure 15:
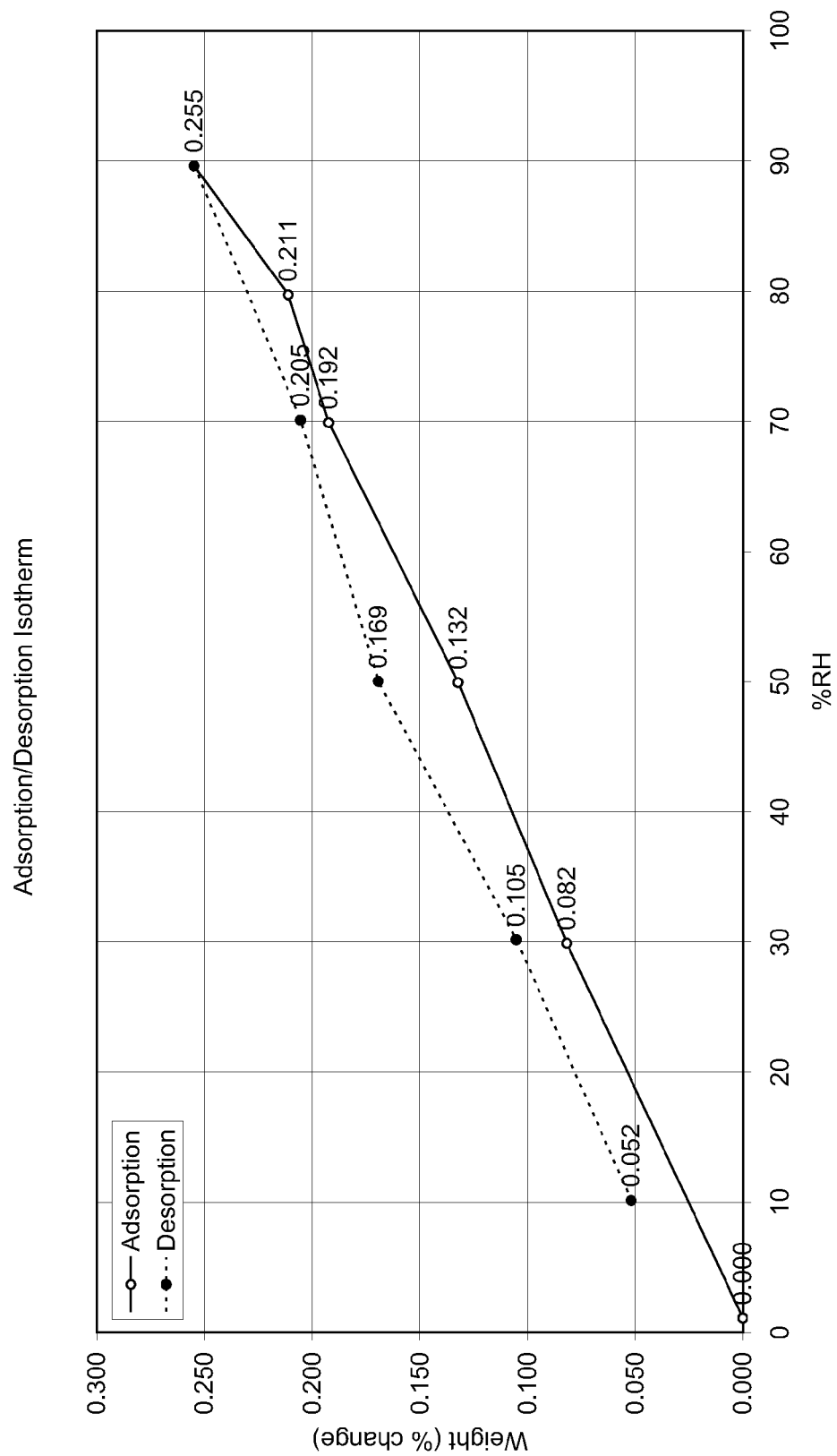
FIG. 15: DMS of Compound 1 Hemimucate Salt, Form I.

In some embodiments, the Compound 1 hemimucate salt has a dynamic moisture sorption profile substantially as shown in FIG. 15, wherein by "substantially" is meant that the reported DMS features can vary by about ±5% relative humidity and by about ±5% weight change.

Form I of Compound 1 hemimucate salt can be prepared by any of the suitable procedures known in the art for preparing crystalline polymorphs. In some embodiments Form I of Compound 1 hemimucate salt can be prepared as described in Example 5. In some embodiments, Form I of Compound 1 hemimucate salt can be prepared by slurrying crystalline Compound 1 hemimucate salt containing one or more crystalline forms other than Form I. In some embodiments, Form I of Compound 1 hemimucate salt can be prepared by recrystallizing crystalline Compound 1 hemimucate salt containing one or more crystalline forms other than Form I.

Compound 1 Glucuronate Salt.

One aspect of the present invention pertains to (R)-8-chloro-1-methyl-2,3,4,5-tetrahydro-1H-3-benzazepine glucuronate, Form I (Compound 1 glucuronate salt, Form I). The physical properties of Compound 1 glucuronate salt, Form I are summarized in Table 11 below.

TABLE 11

Figure 16:
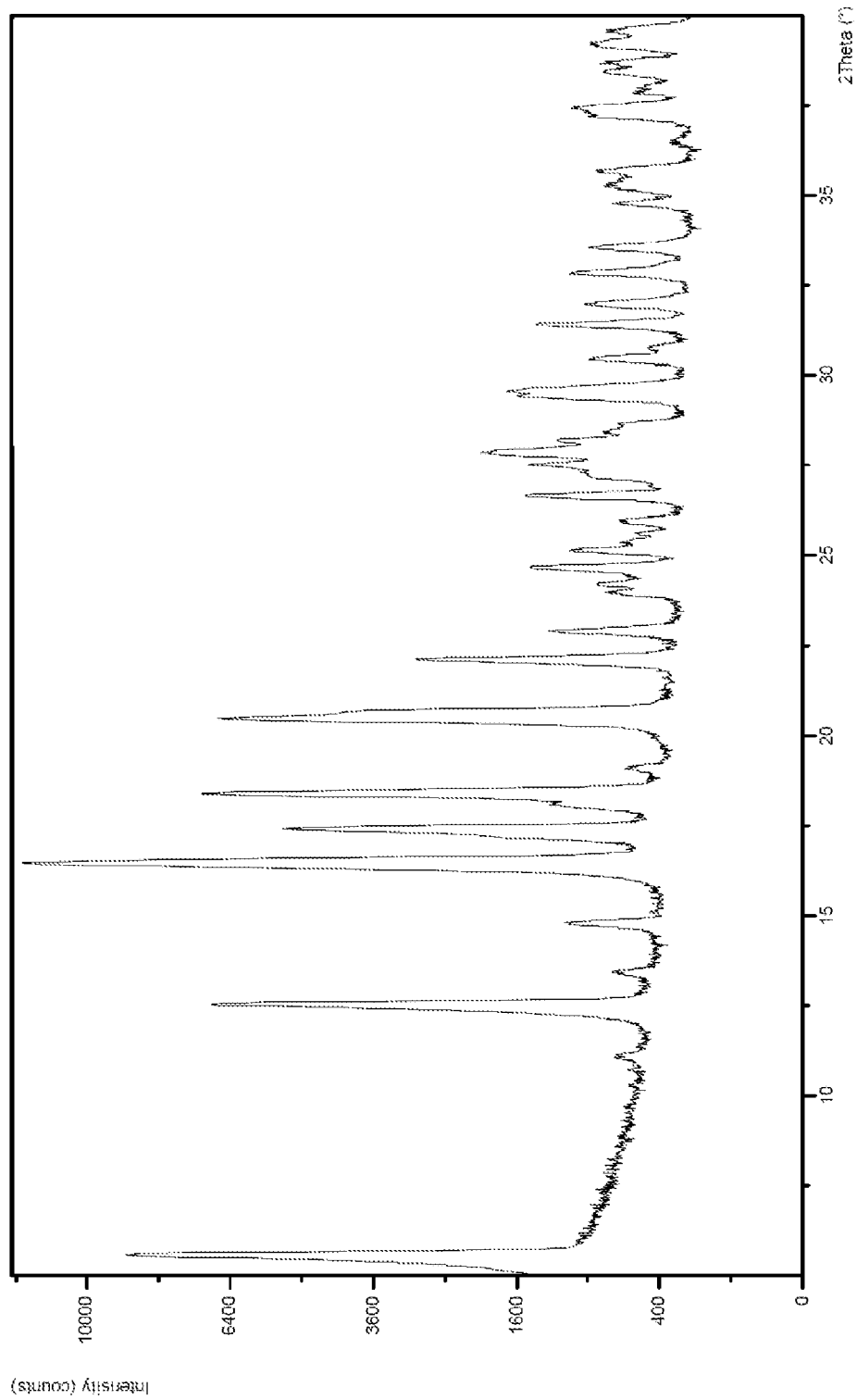
FIG. 16: PXRD of Compound 1 Pyroglutamate Salt, Form I.

|  | Compound 1 Glucuronate Salt, Form I |
|---|---|
| PXRD | FIG. 16: Peaks of 10>% relative intensity at 5.59, 12.54, 16.46, 17.41, 18.40, 20.48, 20.69, 22.12, 26.66, 27.53, 27.85, and 29.57 °2θ |
| TGA | FIG. 17: about 20% weight loss from about 150° C. to about 165° C. |
| DSC | FIG. 17: extrapolated onset temperature: 164° C.; enthalpy of fusion 124 J/g |
| DMS | FIG. 18: 0.16% weight increase out to 90% RH |

Compound 1 glucuronate salt was an anhydrous crystalline material with melting onset of ~164° C. Based on rapid weight loss of about 20% starting just prior to the melting onset, this salt melted with degradation. It was non-hygroscopic by DMS picking up about 0.16% out to and including the 90% RH hold at 25° C.

Certain X-ray powder diffraction peaks for Form I of Compound 1 glucuronate salt are shown in Table 12 below.

TABLE 12

| Pos. (°2θ) | Rel. Int. (%) |
|---|---|
| 5.59 | 71.04 |
| 11.10 | 1.23 |
| 12.54 | 55.77 |
| 13.43 | 2.10 |
| 14.79 | 5.71 |
| 16.46 | 100.00 |
| 17.41 | 42.46 |
| 18.09 | 7.55 |
| 18.40 | 58.29 |
| 19.10 | 1.99 |
| 20.48 | 55.27 |
| 20.69 | 30.98 |
| 22.12 | 22.45 |
| 22.90 | 8.02 |
| 23.98 | 3.46 |
| 24.20 | 4.29 |
| 24.68 | 9.76 |
| 25.13 | 6.41 |
| 25.94 | 2.74 |
| 26.66 | 10.40 |
| 27.26 | 5.26 |
| 27.53 | 10.09 |
| 27.85 | 14.59 |
| 28.19 | 7.69 |
| 28.64 | 2.99 |
| 29.39 | 9.66 |
| 29.57 | 12.34 |
| 30.47 | 5.19 |
| 31.42 | 9.83 |
| 31.98 | 5.74 |
| 32.84 | 6.85 |
| 33.55 | 5.41 |
| 34.78 | 3.60 |
| 35.28 | 4.12 |
| 35.68 | 4.57 |
| 37.18 | 5.03 |
| 37.42 | 6.79 |
| 38.44 | 4.53 |
| 38.68 | 4.38 |
| 39.21 | 5.43 |
| 39.58 | 4.06 |

One aspect of the present invention is directed to a Compound 1 glucuronate salt having an X-ray powder diffraction pattern comprising a peak, in terms of 2θ, at about 16.46°. In some embodiments, the crystalline form has an X-ray powder diffraction pattern comprising a peak, in terms of 2θ, at about 5.59°. In some embodiments, the crystalline form has an X-ray powder diffraction pattern comprising peaks, in terms of 2θ, at about 16.46° and about 5.59°. In some embodiments, the crystalline form has an X-ray powder diffraction pattern comprising peaks, in terms of 2θ, at about 16.46° and about 18.40°. In some embodiments, the crystalline form has an X-ray powder diffraction pattern comprising peaks, in terms of 2θ, at about 16.46°, about 5.59°, and about 18.40°. In some embodiments, the crystalline form has an X-ray powder diffraction pattern comprising peaks, in terms of 2θ, at about 16.46°, about 5.59°, about 18.40°, about 12.54°, about 20.48°, about 17.41°, and about 20.69°. In some embodiments, the crystalline form has an X-ray powder diffraction pattern comprising peaks, in terms of 2θ, at about 16.46°, about 5.59°, about 18.40°, about 12.54°, about 20.48°, about 17.41°, about 20.69°, about 22.12°, about 27.85°, and about 29.57°. One aspect of the present invention is directed to a Compound 1 glucuronate salt having an X-ray powder diffraction pattern comprising one or more peaks listed in Table 12. In some embodiments, the crystalline form has an X-ray powder diffraction pattern substantially as shown in FIG. 16, wherein by "substantially" is meant that the reported peaks can vary by about ±0.2° 2θ, and also that the relative intensities of the reported peaks can vary.

In some embodiments, the Compound 1 glucuronate salt has a differential scanning calorimetry thermogram comprising an endotherm with an extrapolated onset temperature between about 150° C. and about 180° C. In some embodiments, the Compound 1 glucuronate salt has a differential scanning calorimetry thermogram comprising an endotherm with an extrapolated onset temperature at about 164° C. In some embodiments, the Compound 1 glucuronate salt has a differential scanning calorimetry thermogram comprising an endotherm with an associated heat flow of about 124 joules per gram. In some embodiments, the Compound 1 glucuronate salt has a differential scanning calorimetry thermogram substantially as shown in FIG. 17, wherein by "substantially" is meant that the reported DSC features can vary by about ±6° C. and by about ±20 joules per gram.

Figure 17:
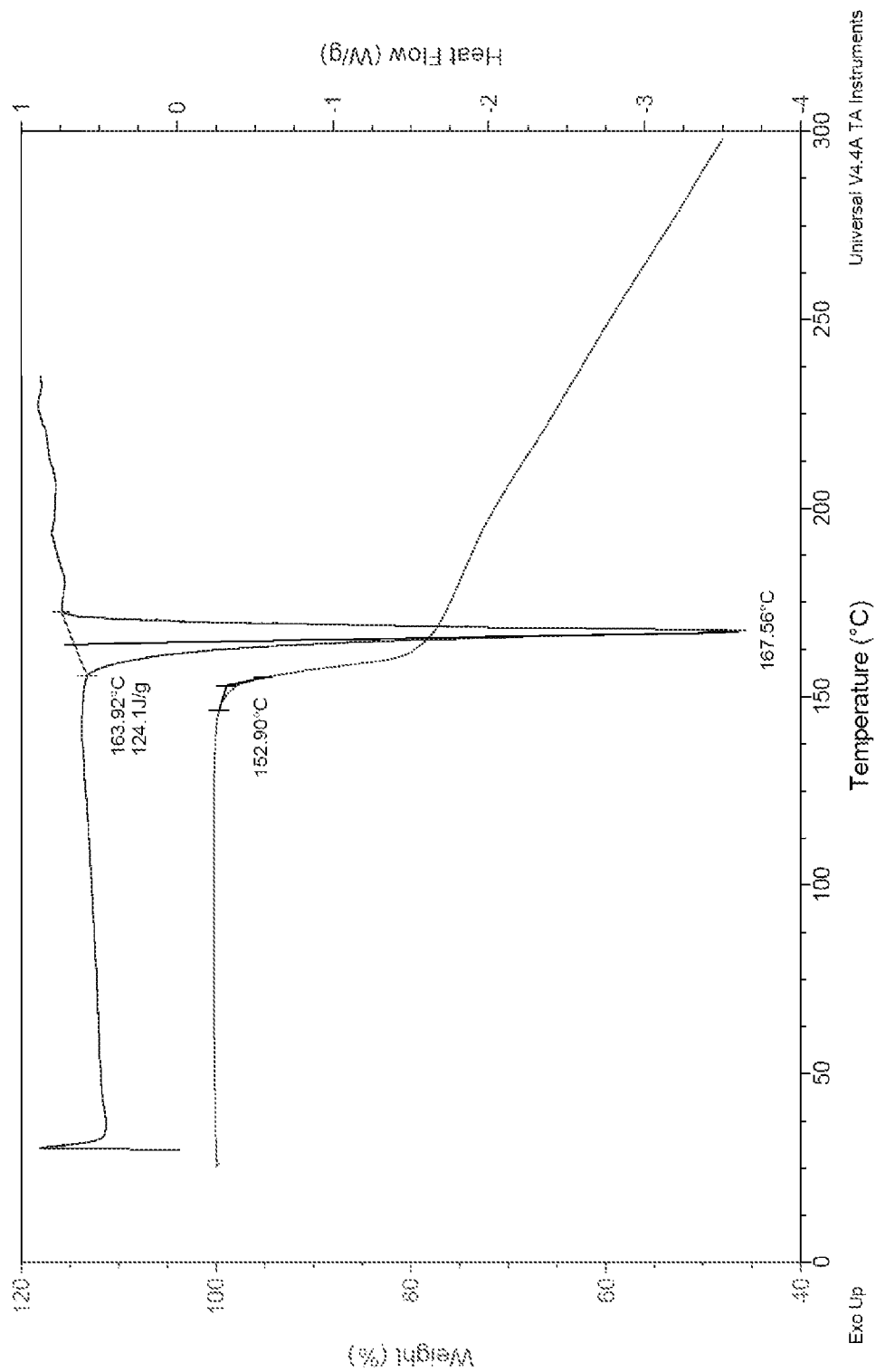
FIG. 17: DSC and TGA of Compound 1 Pyroglutamate Salt, Form I.

In some embodiments, the Compound 1 glucuronate salt has a thermogravimetric analysis profile substantially as shown in FIG. 17, wherein by "substantially" is meant that the reported TGA features can vary by about ±5° C. and by about ±2% weight change.

Figure 18:
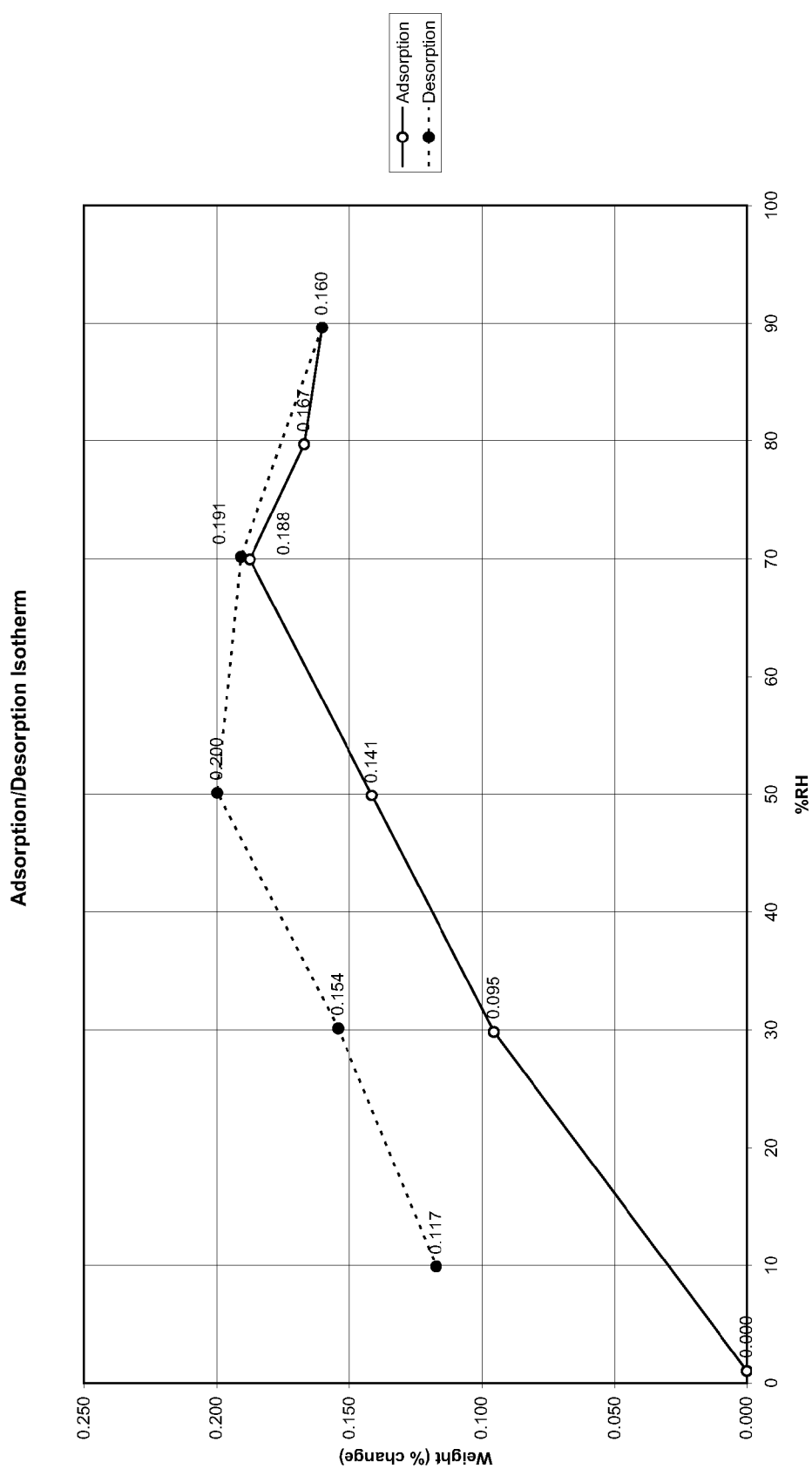
FIG. 18: DMS of Compound 1 Pyroglutamate Salt, Form I.

In some embodiments, the Compound 1 glucuronate salt has a dynamic moisture sorption profile substantially as shown in FIG. 18, wherein by "substantially" is meant that the reported DMS features can vary by about ±5% relative humidity and by about ±5% weight change.

Form I of Compound 1 glucuronate salt can be prepared by any of the suitable procedures known in the art for preparing crystalline polymorphs. In some embodiments Form I of Compound 1 glucuronate salt can be prepared as described in Example 6. In some embodiments, Form I of Compound 1 glucuronate salt can be prepared by slurrying crystalline Compound 1 glucuronate salt containing one or more crystalline forms other than Form I. In some embodiments, Form I of Compound 1 glucuronate salt can be prepared by recrystallizing crystalline Compound 1 glucuronate salt containing one or more crystalline forms other than Form I.

Compound 1 Pyrogluconate Salt.

One aspect of the present invention pertains to (R)-8-chloro-1-methyl-2,3,4,5-tetrahydro-1H-3-benzazepine pyrogluconate, Form I (Compound 1 pyrogluconate salt, Form I). The physical properties of Compound 1 pyrogluconate salt, Form I are summarized in Table 13 below.

TABLE 13

Figure 19:
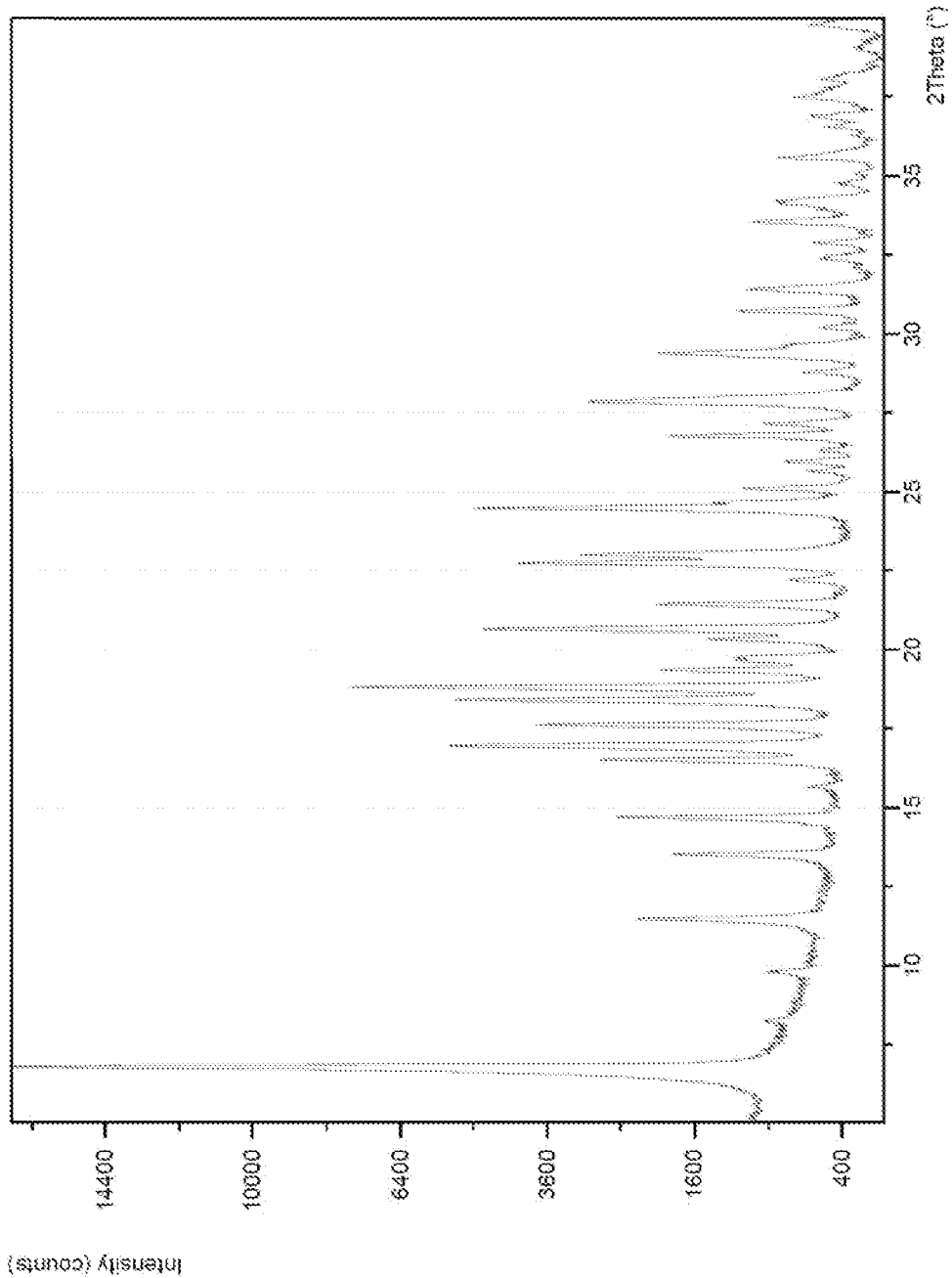
FIG. 19: PXRD of Compound 1 Glucuronate Salt, Form I.

| | Compound 1 Pyrogluconate Salt, Form I |
|---|---|
| PXRD | FIG. 19: Peaks of >12% relative intensity at 6.78, 14.69, 16.50, 16.95, 17.61, 18.40, 18.80, 20.66, 22.72, 22.99, 24.47, and 27.84 °2θ |
| TGA | FIG. 20: No significant weight loss prior to melting |
| DSC | FIG. 20: extrapolated onset temperature: 139° C.; enthalpy of fusion 70.8 J/g |
| DMS | FIG. 21: 17-24% weight increase at 70% RH, about 50% weight increase at 90% RH |

Form I of Compound 1 pyrogluconate salt was a crystalline solid with a small broad endotherm prior to a melting endotherm with an onset at 139° C. and heat of fusion of 70.8 J/g. Prior to the melting onset there was minimal weight loss by TGA and upon melting there was a gradual and complete weight loss, indicating the isolated crystal phase was not a solvate.

Compound 1 pyroglutamate salt, Form I was hygroscopic above approximately 50% RH, picking up during the adsorption cycle nearly 17% water at 70% RH, nearly 50% water out to and including the 90% RH hold at 25° C. and still gaining weight after 2 h at 90% RH. The sample subsequently retained much of the water, even down to 10% RH. The sample after removal from the dynamic moisture-sorption analyzer was a sticky oil, so no further analysis was performed.

Certain X-ray powder diffraction peaks for Form I of Compound 1 pyrogluconate salt are shown in Table 14 below.

TABLE 14

| Pos. (°2θ) | Rel. Int. (%) |
|---|---|
| 6.78 | 100.00 |
| 8.23 | 1.01 |
| 8.81 | 0.12 |
| 9.81 | 1.29 |
| 11.46 | 10.49 |
| 13.52 | 8.13 |
| 14.69 | 12.51 |
| 14.93 | 0.29 |
| 15.64 | 0.69 |
| 16.50 | 13.75 |
| 16.95 | 29.48 |
| 17.61 | 19.64 |
| 18.40 | 28.95 |
| 18.80 | 42.64 |
| 19.34 | 9.09 |
| 19.64 | 4.51 |
| 19.74 | 4.37 |
| 20.31 | 6.19 |
| 20.66 | 25.68 |
| 21.43 | 9.44 |
| 22.20 | 2.03 |
| 22.72 | 21.94 |
| 22.99 | 15.93 |
| 24.47 | 26.51 |
| 24.66 | 6.06 |
| 25.11 | 4.29 |
| 25.65 | 1.49 |
| 25.95 | 2.44 |
| 26.31 | 0.97 |
| 26.77 | 9.30 |
| 27.15 | 3.37 |
| 27.84 | 15.61 |
| 27.95 | 9.89 |
| 28.79 | 1.85 |
| 29.39 | 10.02 |
| 29.66 | 2.60 |
| 30.20 | 1.19 |
| 30.72 | 5.02 |
| 31.41 | 4.47 |
| 32.37 | 1.31 |
| 32.47 | 1.18 |
| 32.88 | 1.48 |
| 33.53 | 4.21 |
| 33.93 | 1.51 |
| 34.12 | 3.03 |
| 34.21 | 3.29 |
| 34.77 | 0.82 |
| 35.08 | 0.22 |
| 35.57 | 3.35 |
| 36.30 | 0.45 |
| 36.55 | 1.29 |
| 36.89 | 1.92 |
| 37.49 | 2.67 |
| 38.05 | 1.53 |
| 38.57 | 0.08 |
| 39.05 | 0.39 |
| 39.25 | 0.16 |
| 39.78 | 1.97 |

One aspect of the present invention is directed to a Compound 1 pyrogluconate salt having an X-ray powder diffraction pattern comprising a peak, in terms of 2θ, at about 6.78°. In some embodiments, the crystalline form has an X-ray powder diffraction pattern comprising a peak, in terms of 2θ, at about 18.80°. In some embodiments, the crystalline form has an X-ray powder diffraction pattern comprising peaks, in terms of 2θ, at about 6.78° and about 18.80°. In some embodiments, the crystalline form has an X-ray powder diffraction pattern comprising peaks, in terms of 2θ, at about 6.78° and about 16.95°. In some embodiments, the crystalline form has an X-ray powder diffraction pattern comprising peaks, in terms of 2θ, at about 6.78°, about 18.80°, and about 16.95°. In some embodiments, the crystalline form has an X-ray powder diffraction pattern comprising peaks, in terms of 2θ, at about 6.78°, about 18.80°, about 16.95°, about 18.40°, about 24.47°, about 20.66°, and about 22.72°. In some embodiments, the crystalline form has an X-ray powder diffraction pattern comprising peaks, in terms of 2θ, at about 6.78°, about 18.80°, about 16.95°, about 18.40°, about 24.47°, about 20.66°, about 22.72°, about 17.61°, about 22.99°, and about 27.84°. One aspect of the present invention is directed to a Compound 1 pyrogluconate salt having an X-ray powder diffraction pattern comprising one or more peaks listed in Table 14. In some embodiments, the crystalline form has an X-ray powder diffraction pattern substantially as shown in FIG. 19, wherein by "substantially" is meant that the reported peaks can vary by about ±0.2° 2θ, and also that the relative intensities of the reported peaks can vary.

In some embodiments, the Compound 1 pyrogluconate salt has a differential scanning calorimetry thermogram comprising an endotherm with an extrapolated onset temperature between about 120° C. and about 150° C. In some embodiments, the Compound 1 pyrogluconate salt has a differential scanning calorimetry thermogram comprising an endotherm with an extrapolated onset temperature at about 139° C. In some embodiments, the Compound 1 pyrogluconate salt has a differential scanning calorimetry thermogram comprising an endotherm with an associated heat flow of about 73 joules per gram. In some embodiments, the Compound 1 pyrogluconate salt has a differential scanning calorimetry thermogram substantially as shown in FIG. 20, wherein by "substantially" is meant that the reported DSC features can vary by about ±6° C. and by about ±20 joules per gram.

Figure 20:
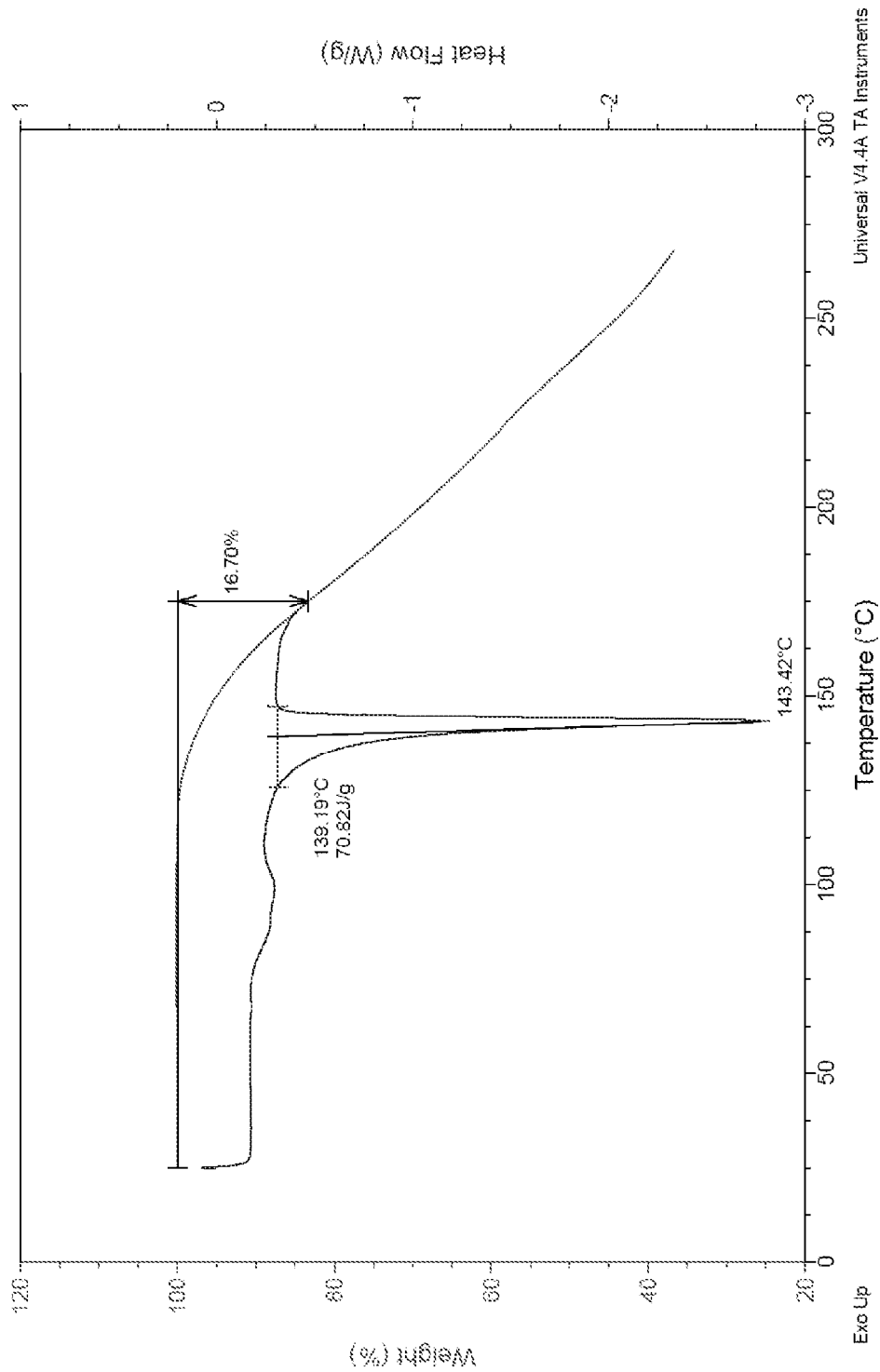
FIG. 20: DSC and TGA of Compound 1 Glucuronate Salt, Form I.

In some embodiments, the Compound 1 pyrogluconate salt has a thermogravimetric analysis profile substantially as shown in FIG. 20, wherein by "substantially" is meant that the reported TGA features can vary by about ±5° C. and by about ±2% weight change.

Figure 21:
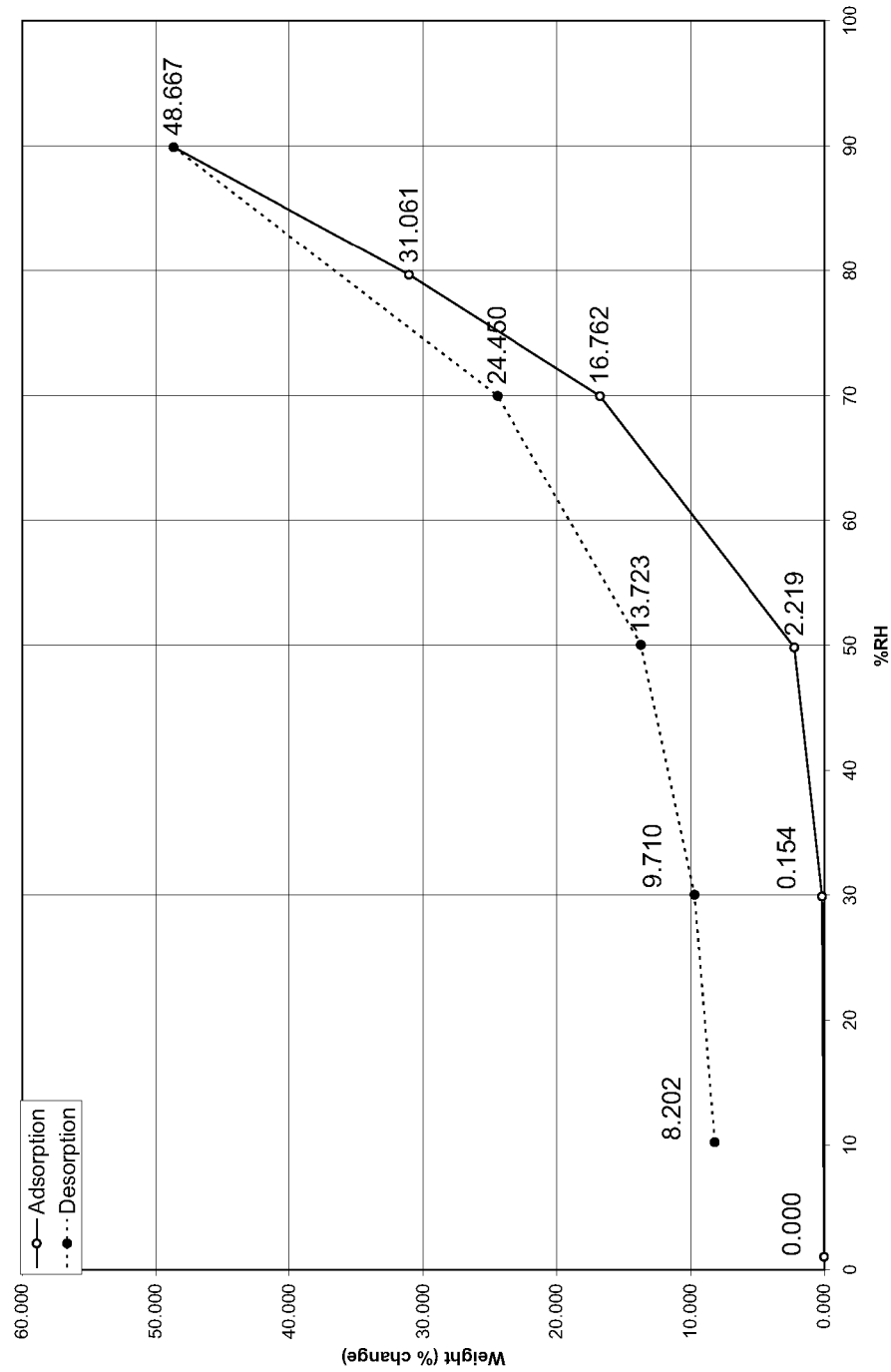
FIG. 21: DMS of Compound 1 Glucuronate Salt, Form I.

In some embodiments, the Compound 1 pyrogluconate salt has a dynamic moisture sorption profile substantially as shown in FIG. 21, wherein by "substantially" is meant that the reported DMS features can vary by about ±5% relative humidity and by about ±5% weight change.

Form I of Compound 1 pyrogluconate salt can be prepared by any of the suitable procedures known in the art for preparing crystalline polymorphs. In some embodiments Form I of Compound 1 pyrogluconate salt can be prepared as described in Example 7. In some embodiments, Form I of Compound 1 pyrogluconate salt can be prepared by slurrying crystalline Compound 1 pyrogluconate salt containing one or more crystalline forms other than Form I. In some embodiments, Form I of Compound 1 pyrogluconate salt can be prepared by recrystallizing crystalline Compound 1 pyrogluconate salt containing one or more crystalline forms other than Form I.

Compound 1 Di-Camphorate Salt Solvate.

One aspect of the present invention pertains to (R)-8-chloro-1-methyl-2,3,4,5-tetrahydro-1H-3-benzazepine di-camphorate salt solvate, Form I (Compound 1 di-camphorate salt solvate, Form I). The physical properties of Compound 1 di-camphorate salt solvate, Form I are summarized in Table 15 below.

TABLE 15

Figure 22:
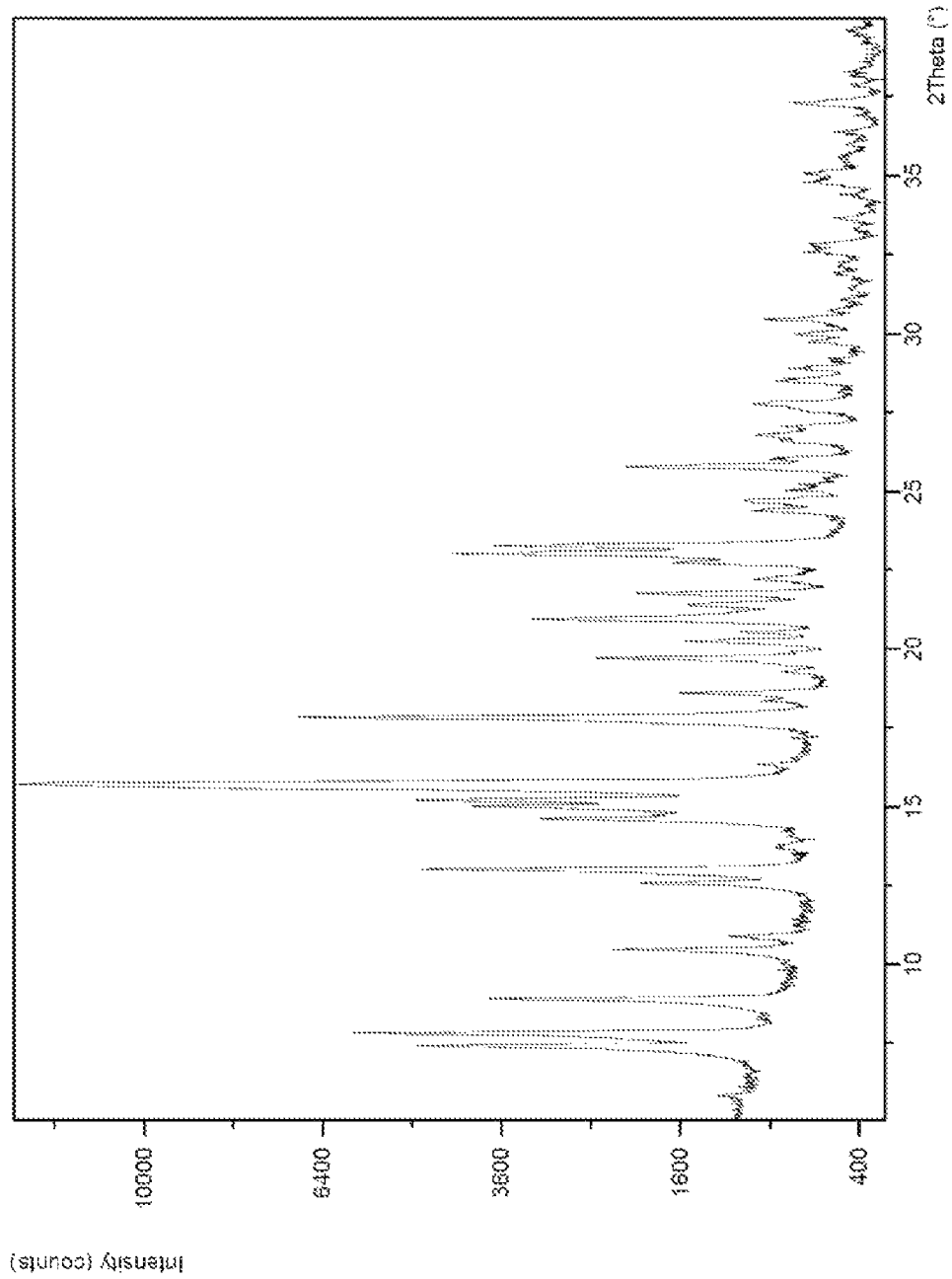
FIG. 22: PXRD of Compound 1 Di-camphorate Salt Solvate, Form I.

| Compound 1 Di-camphorate Salt Solvate, Form I | |
|---|---|
| PXRD | FIG. 22: Peaks of >25% relative intensity at 7.39, 7.80, 8.91, 13.01, 15.01, 15.20, 15.58, 15.70, 17.83, 23.00, and 23.25 °2θ |
| TGA | FIG. 23: 4.135% weight loss up to about 110° C. |
| DSC | FIG. 23: extrapolated onset temperature: 90° C.; enthalpy of fusion 55 J/g |
| DMS | FIG. 24: 1.8% weight increase out to 90% RH |

Form I of Compound 1 di-camphorate salt solvate showed a broad melting onset at approximately 90° C. and an enthalpy of fusion of 55 J/g by DSC. By TGA the sample lost approximately 4% of its weight during melting/desolvation and continued to lose weight after the melt.

During DMS analysis of Compound 1 di-camphorate salt solvate the sample gained up to 1.8% weight in water out to and including the 90% RH hold at 25° C. Hysteresis was evident on the desorption isotherm. The sample lost over 1.2% weight on the desorption phase at 25° C. and 10% RH, which had not been removed during the drying step at 40° C. and ~1% RH. After DMS analysis the sample remained a white solid, and the PXRD pattern of this material was consistent with the original material indicating that the crystalline phase did not change.

Certain X-ray powder diffraction peaks for Form I of Compound 1 di-camphorate salt solvate are shown in Table 16 below.

TABLE 16

| Pos. (°2θ) | Rel. Int. (%) |
|---|---|
| 7.39 | 35.15 |
| 7.80 | 43.69 |
| 8.91 | 27.48 |
| 10.46 | 14.91 |
| 10.86 | 6.49 |
| 12.56 | 13.13 |
| 13.01 | 34.99 |
| 14.61 | 21.92 |
| 15.01 | 29.30 |
| 15.20 | 35.92 |
| 15.58 | 66.15 |
| 15.70 | 100.00 |
| 17.83 | 52.03 |
| 18.60 | 10.25 |
| 19.69 | 16.79 |
| 20.22 | 9.67 |
| 20.95 | 23.04 |
| 21.40 | 9.52 |
| 21.75 | 13.25 |
| 22.21 | 5.09 |
| 22.72 | 10.43 |
| 23.00 | 31.07 |
| 23.25 | 26.41 |
| 24.37 | 5.27 |
| 24.70 | 5.87 |
| 25.78 | 14.42 |
| 26.73 | 4.39 |
| 27.73 | 4.76 |
| 28.52 | 3.94 |
| 30.00 | 3.04 |
| 30.43 | 3.17 |
| 32.71 | 2.08 |
| 35.07 | 2.00 |
| 37.30 | 3.13 |

One aspect of the present invention is directed to a Compound 1 di-camphorate salt solvate having an X-ray powder diffraction pattern comprising a peak, in terms of 2θ, at about 15.70°. In some embodiments, the crystalline form has an X-ray powder diffraction pattern comprising a peak, in terms of 2θ, at about 15.58°. In some embodiments, the crystalline form has an X-ray powder diffraction pattern comprising peaks, in terms of 2θ, at about 15.70° and about 15.58°. In some embodiments, the crystalline form has an X-ray powder diffraction pattern comprising peaks, in terms of 2θ, at about 15.70° and about 17.83°. In some embodiments, the crystalline form has an X-ray powder diffraction pattern comprising peaks, in terms of 2θ, at about 15.70°, about 15.58°, and about 17.83°. In some embodiments, the crystalline form has an X-ray powder diffraction pattern comprising peaks, in terms of 2θ, at about 15.70°, about 15.58°, about 17.83°, about 7.80°, about 15.20°, about 7.39°, and about 13.01°. In some embodiments, the crystalline form has an X-ray powder diffraction pattern comprising peaks, in terms of 2θ, at about 15.70°, about 15.58°, about 17.83°, about 7.80°, about 15.20°, about 7.39°, about 13.01°, about 23.00°, about 15.01°, and about 8.91°. One aspect of the present invention is directed to a Compound 1 di-camphorate salt solvate having an X-ray powder diffraction pattern comprising one or more peaks listed in Table 16. In some embodiments, the crystalline form has an X-ray powder diffraction pattern substantially as shown in FIG. 22, wherein by "substantially" is meant that the reported peaks can vary by about ±0.2° 2θ, and also that the relative intensities of the reported peaks can vary.

In some embodiments, the Compound 1 di-camphorate salt solvate has a differential scanning calorimetry thermogram comprising an endotherm with an extrapolated onset temperature between about 75° C. and about 105° C. In some embodiments, the Compound 1 di-camphorate salt solvate has a differential scanning calorimetry thermogram comprising an endotherm with an extrapolated onset temperature at about 90° C. In some embodiments, the Compound 1 di-camphorate salt solvate has a differential scanning calorimetry thermogram comprising an endotherm with an associated heat flow of about 55 joules per gram. In some embodiments, the Compound 1 di-camphorate salt solvate has a differential scanning calorimetry thermogram substantially as shown in FIG. 23, wherein by "substantially" is meant that the reported DSC features can vary by about ±6° C. and by about ±20 joules per gram.

Figure 23:
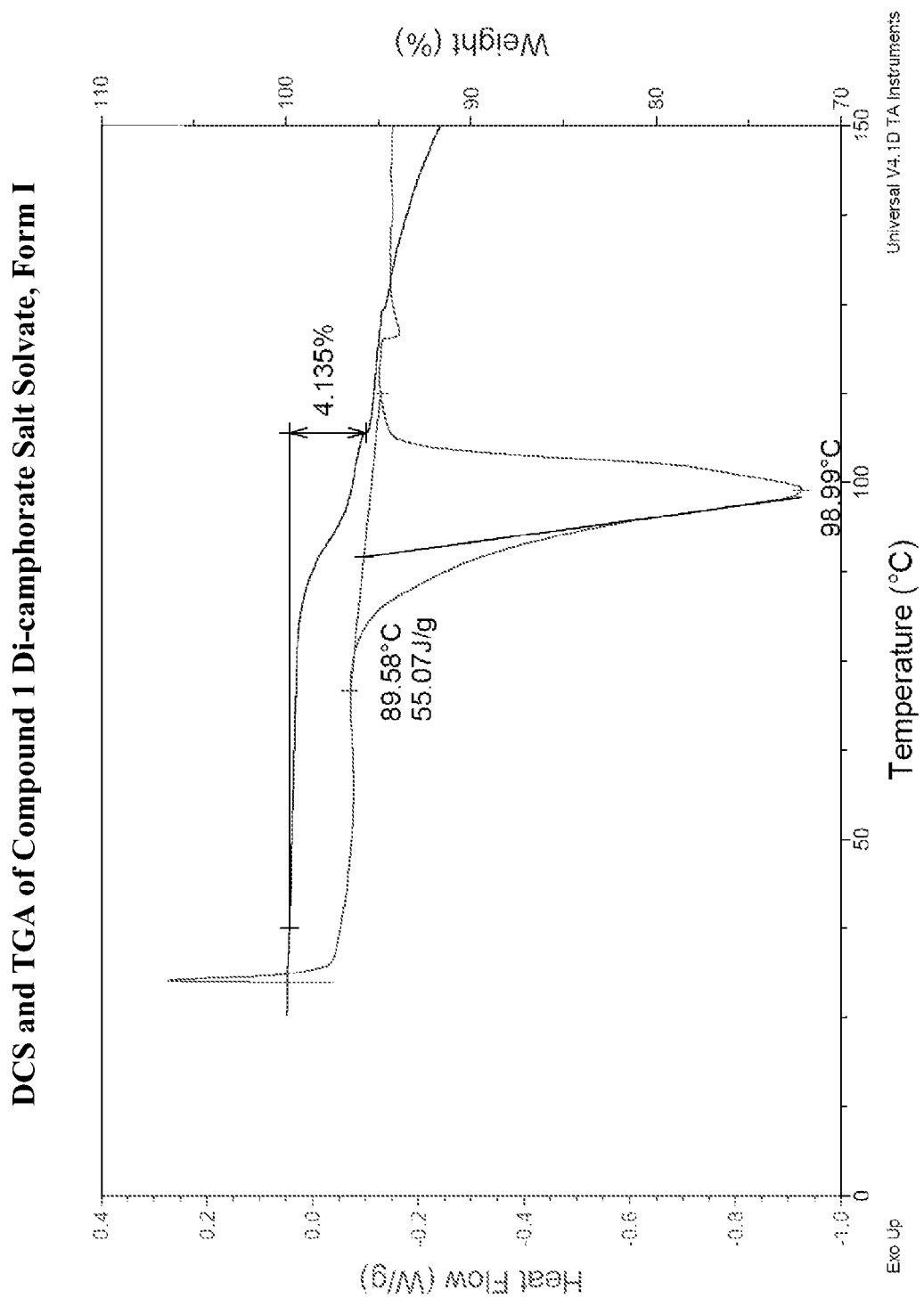
FIG. 23: DSC and TGA of Compound 1 Di-camphorate Salt Solvate, Form I.

In some embodiments, the Compound 1 di-camphorate salt solvate has a thermogravimetric analysis profile substantially as shown in FIG. 23, wherein by "substantially" is meant that the reported TGA features can vary by about ±5° C. and by about ±2% weight change.

Figure 24:
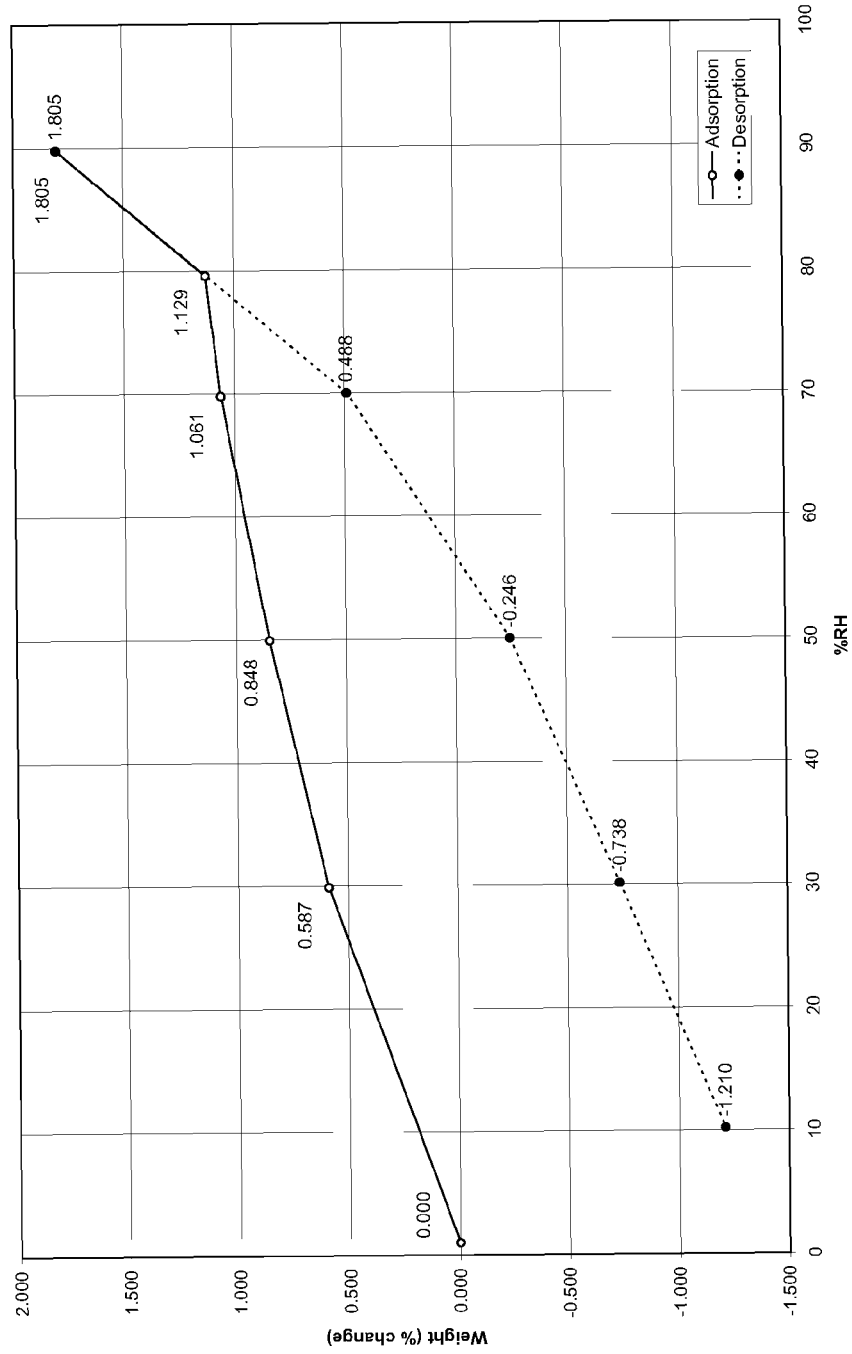
FIG. 24: DMS of Compound 1 Di-camphorate Salt Solvate, Form I.

In some embodiments, the Compound 1 di-camphorate salt solvate has a dynamic moisture sorption profile substantially as shown in FIG. 24, wherein by "substantially" is meant that the reported DMS features can vary by about ±5% relative humidity and by about ±5% weight change.

Form I of Compound 1 di-camphorate salt solvate can be prepared by any of the suitable procedures known in the art for preparing crystalline polymorphs. In some embodiments Form I of Compound 1 di-camphorate salt solvate can be prepared as described in Example 8. In some embodiments, Form I of Compound 1 di-camphorate salt solvate can be prepared by slurrying crystalline Compound 1 di-camphorate salt solvate containing one or more crystalline forms other than Form I. In some embodiments, Form I of Compound 1 di-camphorate salt solvate can be prepared by recrystallizing crystalline Compound 1 di-camphorate salt solvate containing one or more crystalline forms other than Form I.

One aspect of the present invention pertains to processes for preparing a pharmaceutical composition comprising admixing a crystalline salt of the present invention, and a pharmaceutically acceptable carrier.

One aspect of the present invention pertains to processes for preparing a bulk pharmaceutical composition comprising admixing a crystalline salt of the present invention, and a pharmaceutically acceptable carrier.

One aspect of the present invention pertains to methods for weight management, comprising administering to an individual in need thereof, a therapeutically effective amount of a crystalline salt of the present invention.

One aspect of the present invention pertains to the use of crystalline salts of the present invention, in the manufacture of a medicament for weight management in an individual.

One aspect of the present invention pertains to crystalline salts of the present invention, for use in a method of treatment of the human or animal body by therapy.

One aspect of the present invention pertains to crystalline salts of the present invention, for use in a method of weight management.

One aspect of the present invention pertains to crystalline salts of the present invention, for use in a method of weight loss.

One aspect of the present invention pertains to crystalline salts of the present invention, for use in a method of maintenance of weight loss.

One aspect of the present invention pertains to crystalline salts of the present invention, for use in a method of decreasing food consumption.

One aspect of the present invention pertains to crystalline salts of the present invention, for use in a method of increasing meal-related satiety.

One aspect of the present invention pertains to crystalline salts of the present invention, for use in a method of reducing pre-meal hunger.

One aspect of the present invention pertains to crystalline salts of the present invention, for use in a method of reducing intra-meal food intake.

One aspect of the present invention pertains to crystalline salts of the present invention, for use in a method of weight management further comprising a reduced-calorie diet.

One aspect of the present invention pertains to crystalline salts of the present invention, for use in a method of weight management further comprising a program of regular exercise.

One aspect of the present invention pertains to crystalline salts of the present invention, for use in a method of weight management further comprising a reduced-calorie diet and a program of regular exercise.

One aspect of the present invention pertains to crystalline salts of the present invention, for use in a method of weight management in an obese patient with an initial body mass index ≥30 kg/m².

One aspect of the present invention pertains to crystalline salts of the present invention, for use in a method of weight management in an overweight patient with an initial body mass index ≥27 kg/m² in the presence of at least one weight related co-morbid condition. One aspect of the present invention pertains to crystalline salts of the present invention, for use in a method of weight management in an overweight patient with an initial body mass index ≥27 kg/m² in the presence of at least one weight related co-morbid condition selected from: hypertension, dyslipidemia, cardiovascular disease, glucose intolerance, and sleep apnea.

One aspect of the present invention pertains to crystalline salts of the present invention, for use in a method of weight management in an individual with an initial body mass index ≥30 kg/m².

One aspect of the present invention pertains to crystalline salts of the present invention, for use in a method of weight management in an individual with an initial body mass index ≥27 kg/m².

One aspect of the present invention pertains to crystalline salts of the present invention, for use in a method of weight management in an individual with an initial body mass index ≥27 kg/m² in the presence of at least one weight related co-morbid condition.

One aspect of the present invention pertains to crystalline salts of the present invention, for use in a method of weight management in an individual with an initial body mass index ≥27 kg/m² in the presence of at least one weight related co-morbid condition selected from: hypertension, dyslipidemia, cardiovascular disease, glucose intolerance, and sleep apnea.

One aspect of the present invention pertains to crystalline salts of the present invention, for use in a method of weight management in an individual with an initial body mass index ≥25 kg/m².

One aspect of the present invention pertains to crystalline salts of the present invention, for use in a method of weight management in an individual with an initial body mass index ≥25 kg/m² in the presence of at least one weight related co-morbid condition.

One aspect of the present invention pertains to crystalline salts of the present invention, for use in a method of weight management in an individual with an initial body mass index ≥25 kg/m² in the presence of at least one weight related co-morbid condition selected from: hypertension, dyslipidemia, cardiovascular disease, glucose intolerance, and sleep apnea.

One aspect of the present invention pertains to crystalline salts of the present invention, for use in a method of weight management in combination with phentermine.

Optical Resolution

Despite the large number of elaborate enantioselective syntheses for the preparation of a single enantiomer to achieve industrial and scientific goals, the separation and purification of enantiomers (components of racemic compounds) is also necessary.

Methods for resolving optical isomers include, without limitation, spontaneous resolution, induced crystallization, resolution by formation of diastereoisomers, resolution by formation of non-covalent diastereoisomers, resolution by diastereoisomeric salt formation, resolution by diastereoisomeric complex formation, half equivalent methods of resolution, separation by crystallization, separation by distillation, separation by supercritical fluid extraction, resolution with mixtures of resolving agents, resolution with a derivative of the target compound, enantioselective chromatography, resolution by formation of covalent diastereoisomers, resolution by substrate selective reaction, kinetic resolution without enzymes, kinetic resolution by enzyme catalysis, resolution by hydrolytic and redox enzymes, kinetic and thermodynamic control, resolutions combined with second-order asymmetric transformations, and enrichment of partially resolved mixtures (Fogassy et al. Optical resolution methods. *Organic & Biomolecular Chemistry*, (2006), 4(16), 3011-3030).

Resolution by diastereoisomeric salt formation is a popular method for the resolution of bases. For example, dibenzoyl tartaric acid (DBTA) and di-p-toluoyl tartaric acid (DPTA) are often used to separate chiral bases (Kozma et al., *Chirality*, 1999, 11, 373). An intermediate of the potent anticancer agent flavopyridol was resolved with (R,R)-DBTA (Kim et al. *J. Med. Chem.*, 2000, 43, 4126). cis-1-Amino-2-indanol, an intermediate for indinavir, was resolved with (S)-2-phenylpropionic acid (Sakurai and Sakai, *Tetrahedron: Asymmetry*, 2003, 14, 411), 3-methylamino-1-(2-thienyl)propan-1-ol, an intermediate for duloxetine, was resolved with (S)-mandelic acid (Sakurai et al., Tetrahedron: Asymmetry, 2003, 14, 3713). Optimum conditions for the resolution of N-methylamphetamine with DPTA (molar ratio, solvent, etc.) were elaborated (Kozma et al., *Chirality*, 1999, 11, 373). A similar investigation involving N-acetyl-phenylalanine as the resolving agent for a series of benzodiazepines was recently reported (Burnouf et al., *J. Med. Chem.*, 2000, 43, 4850). Camphorsulfonic acid was the resolving agent for a metabolite [1-(3-hydroxy-4-methylphenyl)-2-methyl-3-(1-piperidyl)-propanone] of tolperisone (Bálint et al., *Tetrahedron: Asymmetry*, 2000, 11, 1323). Tolperisone enantiomers show different biological profiles: while the R enantiomer is a bronchodilator, the S enantiomer is a central muscle relaxant. (1R)-(+)-3-bromocamphor-8-sulfonic acid [(R)-BRCS] is also an efficient resolving agent e.g. for a tetrahydroquinoline intermediate of the antibacterial agent flumequine (Bálint et al., *Tetrahedron: Asymmetry*, 1999, 10, 1079). Resolution of β,γ-unsaturated amines with (S)-2,3-isopropylideneglycerol hemiphthalate is remarkable in that the chiral center of the resolving agent is separated by six bonds from the carboxyl group (Pallavicini et al., *Tetrahedron: Asymmetry*, 2000, 11, 4017).

(R)-8-Chloro-1-methyl-2,3,4,5-tetrahydro-1H-3-benzazepine can be prepared via fractional crystallization resolution of the hemi-L-tartrate salt of 8-chloro-1-methyl-2,3,4,5-tetrahydro-1H-3-benzazepine (Example 5). Lorcaserin, (R)-8-chloro-1-methyl-2,3,4,5-tetrahydro-1H-3-benzazepine hydrochloride, can be prepared by converting (R)-8-chloro-1-methyl-2,3,4,5-tetrahydro-1H-3-benzazepine hemi-L-tartrate salt to the free base and then treating with HCl.

In view of the growing demand for compounds useful in the treatment of disorders related to the 5-HT$_{2C}$ receptor, new salt forms of racemic 8-chloro-1-methyl-2,3,4,5-tetrahydro-1H-3-benzazepine and (R)-8-chloro-1-methyl-2,3,4,5-tetrahydro-1H-3-benzazepine, with optically active counterions are needed as intermediates in the preparation of the corresponding hydrochloride salt. Salt forms of (R)-8-chloro-1-methyl-2,3,4,5-tetrahydro-1H-3-benzazepine with optically active counterions are also useful for directly preparing pharmaceutical compositions for the treatment of weight loss. In such compositions the API is a salt form of (R)-8-chloro-1-methyl-2,3,4,5-tetrahydro-1H-3-benzazepine with an optically active counterion. Salt forms of (R)-8-chloro-1-methyl-2,3,4,5-tetrahydro-1H-3-benzazepine with optically active counterions can be prepared by treating Compound 1 with optically active acids, or by resolving salt forms of racemic 8-chloro-1-methyl-2,3,4,5-tetrahydro-1H-3-benzazepine with optically active counterions into their diastereoisomers using techniques well-known to one of ordinary skill in the art.

Hydrates and Solvates

It is understood that when the phrase "pharmaceutically acceptable salts, solvates, and hydrates" or the phrase "pharmaceutically acceptable salt, solvate, or hydrate" is used when referring to compounds described herein, it embraces pharmaceutically acceptable solvates and/or hydrates of the compounds, pharmaceutically acceptable salts of the compounds, as well as pharmaceutically acceptable solvates and/or hydrates of pharmaceutically acceptable salts of the compounds. It is also understood that when the phrase "pharmaceutically acceptable solvates and hydrates" or the phrase "pharmaceutically acceptable solvate or hydrate" is used when referring to compounds described herein that are salts, it embraces pharmaceutically acceptable solvates and/or hydrates of such salts.

It will be apparent to those skilled in the art that the dosage forms described herein may comprise, as the active component, either a salts or crystalline form thereof as described herein, or a solvate or hydrate thereof. Moreover, various hydrates and solvates of the salts or crystalline form thereof described herein will find use as intermediates in the manufacture of pharmaceutical compositions. Typical procedures for making and identifying suitable hydrates and solvates, outside those mentioned herein, are well known to those in the art; see for example, pages 202-209 of K. J. Guillory, "Generation of Polymorphs, Hydrates, Solvates, and Amorphous Solids," in: Polymorphism in Pharmaceutical Solids, ed. Harry G. Britain, Vol. 95, Marcel Dekker, Inc., New York, 1999.

Accordingly, one aspect of the present invention pertains to methods of administering hydrates and solvates of salts or crystalline forms thereof described herein and/or their pharmaceutically acceptable salts, that can be isolated and characterized by methods known in the art, such as, thermogravimetric analysis (TGA), TGA-mass spectroscopy, TGA-Infrared spectroscopy, powder X-ray diffraction (XRPD), Karl Fisher titration, high resolution X-ray diffraction, and the like. There are several commercial entities that provide quick and efficient services for identifying solvates and hydrates on a routine basis. Example companies offering these services include Wilmington PharmaTech (Wilmington, Del.), Avantium Technologies (Amsterdam) and Aptuit (Greenwich, Conn.).

Isotopes

The present disclosure includes all isotopes of atoms occurring in the present salts and crystalline forms thereof. Isotopes include those atoms having the same atomic number but different mass numbers. One aspect of the present invention includes every combination of one or more atoms in the present salts and crystalline forms thereof that is replaced with an atom having the same atomic number but a different mass number. One such example is the replacement of an atom that is the most naturally abundant isotope, such as $^1$H or $^{12}$C, found in one the present salts and crystalline forms thereof, with a different atom that is not the most naturally abundant isotope, such as $^2$H or $^3$H (replacing $^1$H), or $^{11}$C, $^{13}$C, or $^{14}$C (replacing $^{12}$C). A salt wherein such a replacement has taken place is commonly referred to as being isotopically-labeled. Isotopic-labeling of the present salts and crystalline forms thereof can be accomplished using any one of a variety of different synthetic methods know to those of ordinary skill in the art and they are readily credited with understanding the synthetic methods and available reagents needed to conduct such isotopic-labeling. By way of general example, and without limitation, isotopes of hydrogen include $^2$H (deuterium) and $^3$H (tritium). Isotopes of carbon include $^{11}$C, $^{13}$C, and $^{14}$C. Isotopes of nitrogen include $^{13}$N and $^{15}$N. Isotopes of oxygen include $^{15}$O, $^{17}$O, and $^{18}$C. An isotope of fluorine includes $^{18}$F. An isotope of sulfur includes $^{35}$S. An isotope of chlorine includes $^{36}$Cl. Isotopes of bromine include $^{75}$Br, $^{76}$Br, $^{77}$Br, and $^{82}$Br. Isotopes of iodine include $^{123}$I, $^{124}$I, $^{125}$I, and $^{131}$I. Another aspect of the present invention includes compositions, such as, those prepared during synthesis, preformulation, and the like, and pharmaceutical compositions, such as, those prepared with the intent of using in a mammal for the treatment of one or more of the disorders described herein, comprising one or more of the present salts and crystalline forms thereof, wherein the naturally occurring distribution of the isotopes in the composition is perturbed.

Another aspect of the present invention includes compositions and pharmaceutical compositions comprising salts and crystalline forms thereof as described herein wherein the salt is enriched at one or more positions with an isotope other than the most naturally abundant isotope. Methods are readily available to measure such isotope perturbations or enrichments, such as, mass spectrometry, and for isotopes that are radio-isotopes additional methods are available, such as, radio-detectors used in connection with HPLC or GC.

Pharmaceutical Compositions

A further aspect of the present invention pertains to pharmaceutical compositions comprising one or more salts according to any of the salt embodiments disclosed herein and one or more pharmaceutically acceptable carriers. Some embodiments pertain to pharmaceutical compositions comprising a salt according to any of the salt embodiments disclosed herein and a pharmaceutically acceptable carrier. Some embodiments pertain to pharmaceutical compositions comprising any subcombination of salts according to any of the salt embodiments disclosed herein.

Another aspect of the present invention pertains to methods of producing pharmaceutical compositions comprising admixing one or more salts according to any of the salt embodiments disclosed herein and one or more pharmaceutically acceptable carriers. Some embodiments pertain to a method of producing a pharmaceutical composition comprising admixing a salt according to any of the salt embodiments disclosed herein and a pharmaceutically acceptable carrier. Some embodiments pertain to a methods of producing pharmaceutical compositions comprising admixing any subcombination of salts according to any of the salt embodiments disclosed herein and a pharmaceutically acceptable carrier.

Formulations may be prepared by any suitable method, typically by uniformly mixing the active salt(s) with liquids or finely divided solid carriers, or both, in the required proportions and then, if necessary, forming the resulting mixture into a desired shape.

Conventional excipients, such as binding agents, fillers, acceptable wetting agents, tabletting lubricants and disintegrants may be used in tablets and capsules for oral administration. Liquid preparations for oral administration may be in the form of solutions, emulsions, aqueous or oily suspensions and syrups. Alternatively, the oral preparations may be in the form of dry powder that can be reconstituted with water or another suitable liquid vehicle before use. Additional additives such as suspending or emulsifying agents, non-aqueous vehicles (including edible oils), preservatives and flavorings and colorants may be added to the liquid preparations. Parenteral dosage forms may be prepared by dissolving the salt of the invention in a suitable liquid vehicle and filter sterilizing the solution before filling and sealing an appropriate vial or ampule. These are just a few examples of the many appropriate methods well known in the art for preparing dosage forms.

The salts of the present invention can be formulated into pharmaceutical compositions and bulk pharmaceutical compositions suitable for the manufacture of dosage forms using techniques well known to those in the art. Suitable pharmaceutically-acceptable carriers, outside those mentioned herein, are known in the art; for example, see Remington, *The Science and Practice of Pharmacy*, 20$^{th}$ Edition, 2000, Lippincott Williams & Wilkins, (Editors: Gennaro et al.)

While it is possible that, for use in the prophylaxis or treatment, a salt of the invention may, in an alternative use, be administered as a raw or pure chemical, it is preferable however to present the salt or active ingredient as a pharmaceutical formulation or composition further comprising a pharmaceutically acceptable carrier.

Pharmaceutical formulations include those suitable for oral, rectal, nasal, topical (including buccal and sub-lingual), vaginal or parenteral (including intramuscular, subcutaneous and intravenous) administration or in a form suitable for administration by inhalation, insufflation or by a transdermal patch. Transdermal patches dispense a drug at a controlled rate by presenting the drug for absorption in an efficient manner with minimal degradation of the drug. Typically, transdermal patches comprise an impermeable backing layer, a single pressure sensitive adhesive and a removable protective layer with a release liner. One of ordinary skill in the art will understand and appreciate the techniques appropriate for manufacturing a desired efficacious transdermal patch based upon the needs of the artisan.

The salts of the invention, together with a conventional adjuvant, carrier, or diluent, may thus be placed into the form of pharmaceutical formulations and unit dosages thereof and in such form may be employed as solids, such as tablets or filled capsules, or liquids such as solutions, suspensions, emulsions, elixirs, gels or capsules filled with the same, all for oral use, in the form of suppositories for rectal administration; or in the form of sterile injectable solutions for parenteral (including subcutaneous) use. Such pharmaceutical compositions and unit dosage forms thereof may comprise conventional ingredients in conventional proportions, with or without additional active compounds or principles and such unit dosage forms may contain any suitable effective amount of the active ingredient commensurate with the intended daily dosage range to be employed.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are capsules, tablets, powders, granules or a suspension, with conventional additives such as lactose, mannitol, corn starch or potato starch; with binders such as crystalline cellulose, cellulose derivatives, acacia, corn starch or gelatins; with disintegrators such as corn starch, potato starch or sodium carboxymethyl-cellulose; and with lubricants such as talc or magnesium stearate. The active ingredient may also be administered by injection as a composition wherein, for example, saline, dextrose or water may be used as a suitable pharmaceutically acceptable carrier.

Salts of the present invention or a solvate, hydrate or physiologically functional derivative thereof can be used as active ingredients in pharmaceutical compositions, specifically as $5\text{-HT}_{2C}$-receptor modulators. The term "active ingredient" as defined in the context of a "pharmaceutical composition" and is intended to mean a component of a pharmaceutical composition that provides the primary pharmacological effect, as opposed to an "inactive ingredient" which would generally be recognized as providing no pharmaceutical benefit.

The dose when using the salts of the present invention can vary within wide limits and as is customary and is known to the physician, it is to be tailored to the individual conditions in each individual case. It depends, for example, on the nature and severity of the illness to be treated, on the condition of the patient, on the salt employed or on whether an acute or chronic disease state is treated or prophylaxis conducted or on whether further active compounds are administered in addition to the salts of the present invention. Representative doses of the present invention include, but are not limited to, about 0.001 mg to about 5000 mg, about 0.001 mg to about 2500 mg, about 0.001 mg to about 1000 mg, 0.001 mg to about 500 mg, 0.001 mg to about 250 mg, about 0.001 mg to 100 mg, about 0.001 mg to about 50 mg and about 0.001 mg to about 25 mg. Multiple doses may be administered during the day, especially when relatively large amounts are deemed to be needed, for example 2, 3 or 4 doses. Depending on the individual and as deemed appropriate from the patient's physician or caregiver it may be necessary to deviate upward or downward from the doses described herein.

The amount of active ingredient, or an active salt or derivative thereof, required for use in treatment will vary not only with the particular salt selected but also with the route of administration, the nature of the condition being treated and the age and condition of the patient and will ultimately be at the discretion of the attendant physician or clinician. In general, one skilled in the art understands how to extrapolate in vivo data obtained in a model system, typically an animal model, to another, such as a human. In some circumstances, these extrapolations may merely be based on the weight of the animal model in comparison to another, such as a mammal, preferably a human, however, more often, these extrapolations are not simply based on weights, but rather incorporate a variety of factors. Representative factors include the type, age, weight, sex, diet and medical condition of the patient, the severity of the disease, the route of administration, pharmacological considerations such as the activity, efficacy, pharmacokinetic and toxicology profiles of the particular salt employed, whether a drug delivery system is utilized, on whether an acute or chronic disease state is being treated or prophylaxis conducted or on whether further active compounds are administered in addition to the salts of the present invention and as part of a drug combination. The dosage regimen for treating a disease condition with the salts and/or compositions of this invention is selected in accordance with a variety factors as cited above. Thus, the actual dosage regimen employed may vary widely and therefore may deviate from a preferred dosage regimen and one skilled in the art will recognize that dosage and dosage regimen outside these typical ranges can be tested and, where appropriate, may be used in the methods of this invention.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations. The daily dose can be divided, especially when relatively large amounts are administered as deemed appropriate, into several, for example 2, 3 or 4 part administrations. If appropriate, depending on individual behavior, it may be necessary to deviate upward or downward from the daily dose indicated.

The salts of the present invention can be administrated in a wide variety of oral and parenteral dosage forms. It will be obvious to those skilled in the art that the following dosage forms may comprise, as the active component, either a salt of the invention or a solvate or hydrate of a salt of the invention.

For preparing pharmaceutical compositions from the compounds of the present invention, the selection of a suitable pharmaceutically acceptable carrier can be either solid, liquid or a mixture of both. Solid form preparations include powders, tablets, pills, capsules, cachets, suppositories and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding capacity in suitable proportions and compacted to the desire shape and size.

The powders and tablets may contain varying percentage amounts of the active salt. A representative amount in a powder or tablet may contain from 0.5 to about 90 percent of the active salt; however, an artisan would know when amounts outside of this range are necessary. Suitable carriers for powders and tablets are magnesium carbonate, magnesium stearate, talc, sugar, lactose, pectin, dextrin, starch, gelatin, tragacanth, methylcellulose, sodium carboxymethylcellulose, a low melting wax, cocoa butter and the like. The term "preparation" is intended to include the formulation of the active salt with encapsulating material as carrier providing a capsule in which the active component, with or without carriers, is surrounded by a carrier, which is thus in association with it. Similarly, cachets and lozenges are included. Tablets, powders, capsules, pills, cachets and lozenges can be used as solid forms suitable for oral administration.

For preparing suppositories, a low melting wax, such as an admixture of fatty acid glycerides or cocoa butter, is first melted and the active component is dispersed homogeneously therein, as by stirring. The molten homogenous mixture is then poured into convenient sized molds, allowed to cool and thereby to solidify.

Formulations suitable for vaginal administration may be presented as pessaries, tampons, creams, gels, pastes, foams or sprays containing in addition to the active ingredient such carriers as are known in the art to be appropriate.

Liquid form preparations include solutions, suspensions and emulsions, for example, water or water-propylene glycol solutions. For example, parenteral injection liquid preparations can be formulated as solutions in aqueous polyethylene glycol solution. Injectable preparations, for example, sterile injectable aqueous or oleaginous suspensions may be formulated according to the known art using suitable dispersing or wetting agents and suspending agents. The sterile injectable preparation may also be a sterile injectable solution or suspension in a nontoxic parenterally acceptable diluent or solvent, for example, as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

The compounds according to the present invention may thus be formulated for parenteral administration (e.g. by injection, for example bolus injection or continuous infusion) and may be presented in unit dose form in ampoules, prefilled syringes, small volume infusion or in multi-dose containers with an added preservative. The pharmaceutical compositions may take such forms as suspensions, solutions, or emulsions in oily or aqueous vehicles and may contain formulatory agents such as suspending, stabilizing and/or dispersing agents. Alternatively, the active ingredient may be in powder form, obtained by aseptic isolation of sterile solid or by lyophilization from solution, for constitution with a suitable vehicle, e.g. sterile, pyrogen-free water, before use.

Aqueous formulations suitable for oral use can be prepared by dissolving or suspending the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, or other well-known suspending agents.

Also included are solid form preparations which are intended to be converted, shortly before use, to liquid form preparations for oral administration. Such liquid forms include solutions, suspensions and emulsions. These preparations may contain, in addition to the active component, colorants, flavors, stabilizers, buffers, artificial and natural sweeteners, dispersants, thickeners, solubilizing agents and the like.

For topical administration to the epidermis the salts according to the invention may be formulated as ointments, creams or lotions, or as a transdermal patch.

Ointments and creams may, for example, be formulated with an aqueous or oily base with the addition of suitable thickening and/or gelling agents. Lotions may be formulated with an aqueous or oily base and will in general also contain one or more emulsifying agents, stabilizing agents, dispersing agents, suspending agents, thickening agents, or coloring agents.

Formulations suitable for topical administration in the mouth include lozenges comprising active agent in a flavored base, usually sucrose and acacia or tragacanth; pastilles comprising the active ingredient in an inert base such as gelatin and glycerin or sucrose and acacia; and mouthwashes comprising the active ingredient in a suitable liquid carrier.

Solutions or suspensions are applied directly to the nasal cavity by conventional means, for example with a dropper, pipette or spray. The formulations may be provided in single or multi-dose form. In the latter case of a dropper or pipette, this may be achieved by the patient administering an appropriate, predetermined volume of the solution or suspension. In the case of a spray, this may be achieved for example by means of a metering atomizing spray pump.

Administration to the respiratory tract may also be achieved by means of an aerosol formulation in which the active ingredient is provided in a pressurized pack with a suitable propellant. If the salts of the present invention or pharmaceutical compositions comprising them are administered as aerosols, for example as nasal aerosols or by inhalation, this can be carried out, for example, using a spray, a nebulizer, a pump nebulizer, an inhalation apparatus, a metered inhaler or a dry powder inhaler. Pharmaceutical forms for administration of the salts of the present invention as an aerosol can be prepared by processes well known to the person skilled in the art. For their preparation, for example, solutions or dispersions of the salts of the present invention in water, water/alcohol mixtures or suitable saline solutions can be employed using customary additives, for example benzyl alcohol or other suitable preservatives, absorption enhancers for increasing the bioavailability, solubilizers, dispersants and others and, if appropriate, customary propellants, for example include carbon dioxide, CFCs, such as, dichlorodifluoromethane, trichlorofluoromethane, or dichlorotetrafluoroethane; and the like. The aerosol may conveniently also contain a surfactant such as lecithin. The dose of drug may be controlled by provision of a metered valve.

In formulations intended for administration to the respiratory tract, including intranasal formulations, the salt will generally have a small particle size for example of the order of 10 microns or less. Such a particle size may be obtained by means known in the art, for example by micronization. When desired, formulations adapted to give sustained release of the active ingredient may be employed.

Alternatively the active ingredients may be provided in the form of a dry powder, for example, a powder mix of the salt in a suitable powder base such as lactose, starch, starch derivatives such as hydroxypropylmethyl cellulose and polyvinylpyrrolidone (PVP). Conveniently the powder carrier will form a gel in the nasal cavity. The powder composition may be presented in unit dose form for example in capsules or cartridges of, e.g., gelatin, or blister packs from which the powder may be administered by means of an inhaler.

The pharmaceutical preparations are preferably in unit dosage forms. In such form, the preparation is subdivided into unit doses containing appropriate quantities of the active component. The unit dosage form can be a packaged preparation, the package containing discrete quantities of preparation, such as packeted tablets, capsules and powders in vials or ampoules. Also, the unit dosage form can be a capsule, tablet, cachet, or lozenge itself, or it can be the appropriate number of any of these in packaged form.

Tablets or capsules for oral administration and liquids for intravenous administration are preferred compositions.

Some embodiments of the present invention include a method of producing a pharmaceutical composition for "combination-therapy" comprising admixing at least one salt according to any of the salt embodiments disclosed herein, together with at least one known pharmaceutical agent as described herein and a pharmaceutically acceptable carrier.

It is noted that when the salts of the present invention are utilized as active ingredients in a pharmaceutical composition, these are not intended for use only in humans, but in other non-human mammals as well. Indeed, recent advances in the area of animal health-care mandate that consideration be given for the use of active agents, such as 5-$HT_{2C}$-receptor modulators, for the treatment of a 5-$HT_{2C}$-receptor-associated disease or disorders in companionship animals (e.g., cats, dogs, etc.) and in livestock animals (e.g., cows, chickens, fish, etc.). Those of ordinary skill in the art are readily credited with understanding the utility of such salts in such settings.

One aspect of the present invention pertains to methods for weight management, comprising administering to an individual in need thereof, a therapeutically effective amount of a pharmaceutical composition of the present invention.

One aspect of the present invention pertains to pharmaceutical compositions of the present invention, for use in a method of treatment of the human or animal body by therapy.

One aspect of the present invention pertains to pharmaceutical compositions of the present invention, for use in a method of weight management.

One aspect of the present invention pertains to pharmaceutical compositions of the present invention, for use in a method of weight loss.

One aspect of the present invention pertains to pharmaceutical compositions of the present invention, for use in a method of maintenance of weight loss.

One aspect of the present invention pertains to pharmaceutical compositions of the present invention, for use in a method of decreasing food consumption.

One aspect of the present invention pertains to pharmaceutical compositions of the present invention, for use in a method of increasing meal-related satiety.

One aspect of the present invention pertains to pharmaceutical compositions of the present invention, for use in a method of reducing pre-meal hunger.

One aspect of the present invention pertains to pharmaceutical compositions of the present invention, for use in a method of reducing intra-meal food intake.

One aspect of the present invention pertains to pharmaceutical compositions of the present invention, for use in a method of weight management further comprising a reduced-calorie diet.

One aspect of the present invention pertains to pharmaceutical compositions of the present invention, for use in a method of weight management further comprising a program of regular exercise.

One aspect of the present invention pertains to pharmaceutical compositions of the present invention, for use in a method of weight management further comprising a reduced-calorie diet and a program of regular exercise.

One aspect of the present invention pertains to pharmaceutical compositions of the present invention, for use in a method of weight management in an obese patient with an initial body mass index $\geq 30$ kg/m$^2$.

One aspect of the present invention pertains to pharmaceutical compositions of the present invention, for use in a method of weight management in an overweight patient with an initial body mass index $\geq 27$ kg/m$^2$ in the presence of at least one weight related co-morbid condition.

One aspect of the present invention pertains to pharmaceutical compositions of the present invention, for use in a method of weight management in an overweight patient with an initial body mass index $\geq 27$ kg/m$^2$ in the presence of at least one weight related co-morbid condition selected from: hypertension, dyslipidemia, cardiovascular disease, glucose intolerance, and sleep apnea.

One aspect of the present invention pertains to pharmaceutical compositions of the present invention, for use in a method of weight management in an individual with an initial body mass index $\geq 30$ kg/m$^2$.

One aspect of the present invention pertains to pharmaceutical compositions of the present invention, for use in a method of weight management in an individual with an initial body mass index $\geq 27$ kg/m$^2$.

One aspect of the present invention pertains to pharmaceutical compositions of the present invention, for use in a method of weight management in an individual with an initial body mass index $\geq 27$ kg/m$^2$ in the presence of at least one weight related co-morbid condition.

One aspect of the present invention pertains to pharmaceutical compositions of the present invention, for use in a method of weight management in an individual with an initial body mass index $\geq 27$ kg/m$^2$ in the presence of at least one weight related co-morbid condition selected from: hypertension, dyslipidemia, cardiovascular disease, glucose intolerance, and sleep apnea.

One aspect of the present invention pertains to pharmaceutical compositions of the present invention, for use in a method of weight management in an individual with an initial body mass index $\geq 25$ kg/m$^2$.

One aspect of the present invention pertains to pharmaceutical compositions of the present invention, for use in a method of weight management in an individual with an initial body mass index $\geq 25$ kg/m$^2$ in the presence of at least one weight related co-morbid condition.

One aspect of the present invention pertains to pharmaceutical compositions of the present invention, for use in a method of weight management in an individual with an initial body mass index $\geq 25$ kg/m$^2$ in the presence of at least one weight related co-morbid condition selected from: hypertension, dyslipidemia, cardiovascular disease, glucose intolerance, and sleep apnea.

One aspect of the present invention pertains to pharmaceutical compositions of the present invention, for use in a method of weight management in combination with phentermine.

Indications

Obesity is a life-threatening disorder in which there is an increased risk of morbidity and mortality arising from concomitant diseases such as, but not limited to, type II diabetes, hypertension, stroke, certain forms of cancers and gallbladder disease.

Obesity has become a major healthcare issue in the Western World and increasingly in some third world countries. The increase in the number of obese people is due largely to the increasing preference for high fat content foods but also, and this can be a more important factor, the decrease in activity in most people's lives. In spite of the growing awareness of the health concerns linked to obesity the percentage of individuals that are overweight or obese continues to increase. The most significant concern, from a public health perspective, is that children who are overweight grow up to be overweight or obese adults, and accordingly are at greater risk for major health problems. Therefore, it appears that the number of individuals that are overweight or obese will continue to increase.

Whether someone is classified as overweight or obese is generally determined on the basis of his or her body mass index (BMI) which is calculated by dividing body weight (kg) by height squared (m$^2$). Thus, the units for BMI are kg/m$^2$. BMI is more highly correlated with body fat than any other indicator of height and weight. A person is considered overweight when they have a BMI in the range of 25-30 kg/m$^2$, whereas a person with a BMI over 30 kg/m$^2$ is classified as obese. Obesity is further divided into three classes: Class I (BMI of about 30 to about 34.9 kg/m$^2$), Class II (BMI of about 35 to 39.9 kg/m$^2$) and Class III (about 40 kg/m$^2$ or greater); see Table below for complete classifications.

| Classification Of Weight By Body Mass Index (BMI) | |
|---|---|
| BMI | CLASSIFICATION |
| <18.5 | Underweight |
| 18.5-24.9 | Normal |
| 25.0-29.9 | Overweight |
| 30.0-34.9 | Obesity (Class I) |
| 35.0-39.9 | Obesity (Class II) |
| >40 | Extreme Obesity (Class III) |

As the BMI increases for an individual there is an increased risk of morbidity and mortality relative to an individual with normal BMI. Accordingly, overweight and obese individuals (BMI of about 25 kg/m$^2$ and above) are at increased risk for physical ailments such as, but not limited to, high blood pressure, cardiovascular disease (particularly hypertension), high blood cholesterol, dyslipidemia, type II (non-insulin dependent) diabetes, insulin resistance, glucose intolerance, hyperinsulinemia, coronary heart disease, angina pectoris, congestive heart failure, stroke, gallstones, cholescystitis and cholelithiasis, gout, osteoarthritis, obstructive sleep apnea and respiratory problems, some types of cancer (such as endometrial, breast, prostate, and colon), complications of pregnancy, poor female reproductive health (such as menstrual irregularities, infertility, irregular ovulation), diseases of reproduction (such as sexual dysfunction, both male and female, including male erectile dysfunction), bladder control problems (such as stress incontinence), uric acid nephrolithiasis, psychological disorders (such as depression, eating disorders, distorted body image, and low self esteem). Research has shown that even a modest reduction in body weight can correspond to a significant reduction in the risk of developing other ailments, such as, but not limited to, coronary heart disease.

As mentioned above, obesity increases the risk of developing cardiovascular diseases. Coronary insufficiency, atheromatous disease, and cardiac insufficiency are at the forefront of the cardiovascular complications induced by obesity. The incidence of coronary diseases is doubled in subjects less than 50 years of age who are 30% overweight. The diabetes patient faces a 30% reduced lifespan. After age 45, people with diabetes are about three times more likely than people without diabetes to have significant heart disease and up to five times more likely to have a stroke. These findings emphasize the inter-relations between risks factors for type 2 diabetes and coronary heart disease and the potential value of an integrated approach to the prevention of these conditions based on the prevention of obesity [Perry, I. J., et al. *BMJ* 310, 560-564 (1995)]. It is estimated that if the entire population had an ideal weight, the risk of coronary insufficiency would decrease by 25% and the risk of cardiac insufficiency and of cerebral vascular accidents by 35%.

Diabetes has also been implicated in the development of kidney disease, eye diseases and nervous-system problems. Kidney disease, also called nephropathy, occurs when the kidney's "filter mechanism" is damaged and protein leaks into urine in excessive amounts and eventually the kidney fails. Diabetes is also a leading cause of damage to the retina and increases the risk of cataracts and glaucoma. Finally, diabetes is associated with nerve damage, especially in the legs and feet, which interferes with the ability to sense pain and contributes to serious infections. Taken together, diabetes complications are one of the nation's leading causes of death.

The first line of treatment for individuals that are overweight or obese is to offer diet and life style advice, such as, reducing the fat content of their diet and increasing their physical activity. However many patients find these difficult to maintain and need additional help from drug therapy to sustain results from these efforts.

Most currently marketed products have been unsuccessful as treatments for obesity owing to a lack of efficacy or unacceptable side-effect profiles. The most successful drug so far was the indirectly acting 5-hydroxytryptamine (5-HT) agonist d-fenfluramine (Redux™) but reports of cardiac valve defects in up to one third of the patient population led to its withdrawal by the FDA in 1998.

The 5-HT$_{2C}$ receptor is recognized as a well-accepted receptor target for the treatment of obesity, psychiatric, and other disorders. See, for example, Halford et al., *Serotonergic Drugs Effects on Appetite Expression and Use for the Treatment of Obesity*, Drugs 2007; 67 (1): 27-55; Naughton et al., *A Review Of The Role Of Serotonin Receptors In Psychiatric Disorders*. Human Psychopharmacology (2000), 15(6), 397-415.

(R)-8-Chloro-1-methyl-2,3,4,5-tetrahydro-1H-3-benzazepine hydrochloride (lorcaserin hydrochloride) is an agonist of the 5-HT$_{2C}$ receptor and shows effectiveness at reducing obesity in animal models and humans. In a phase 3 human clinical trial evaluating the safety and efficacy of lorcaserin for weight management, statistical significance (p<0.0001) was achieved on all three of the hierarchically ordered co-primary endpoints for patients treated with lorcaserin versus placebo. Treatment with lorcaserin was generally very well tolerated. An assessment of echocardiograms indicated no apparent drug-related effect on the development of US Food and Drug Administration (FDA)-defined valvulopathy over the two-year treatment period. The hierarchically ordered endpoints were the proportion of patients achieving 5% or greater weight loss after 12 months, the difference in mean weight loss compared to placebo after 12 months, and the proportion of patients achieving 10% or greater weight loss after 12 months. Compared to placebo, using an intent-to-treat last observation carried forward (ITT-LOCF) analysis, treatment with lorcaserin was associated with highly statistically significant (p <0.0001) categorical and average weight loss from baseline after 12 months: 47.5% of lorcaserin patients lost greater than or equal to 5% of their body weight from baseline compared to 20.3% in the placebo group. This result satisfied the efficacy benchmark in the most recent FDA draft guidance. Average weight loss of 5.8% of body weight, or 12.7 pounds, was achieved in the lorcaserin group, compared to 2.2% of body weight, or 4.7 pounds, in the placebo group. Statistical separation from placebo was observed by Week 2, the first post-baseline measurement. 22.6% of lorcaserin patients lost greater than or equal to 10% of their body weight from baseline, compared to 7.7% in the placebo group. Lorcaserin patients who completed 52 weeks of treatment according to the protocol lost an average of 8.2% of body weight, or 17.9 pounds, compared to 3.4%, or 7.3 pounds, in the placebo group (p<0.0001).

In addition, the $5\text{-HT}_{2C}$ receptor is also involved in other diseases, conditions and disorders, such as, obsessive compulsive disorder, some forms of depression, and epilepsy. Accordingly, $5\text{-HT}_{2C}$ receptor agonists can have anti-panic properties, and properties useful for the treatment of sexual dysfunction. In addition, $5\text{-HT}_{2C}$ receptor agonists are useful for the treatment of psychiatric symptoms and behaviors in individuals with eating disorders such as, but not limited to, anorexia nervosa and bulimia nervosa. Individuals with anorexia nervosa often demonstrate social isolation. Anorexic individuals often present symptoms of being depressed, anxious, obsession, perfectionistic traits, and rigid cognitive styles as well as sexual disinterest. Other eating disorders include, anorexia nervosa, bulimia nervosa, binge eating disorder (compulsive eating) and ED-NOS (i.e., eating disorders not otherwise specified—an official diagnosis). An individual diagnosed with ED-NOS possess atypical eating disorders including situations in which the individual meets all but a few of the criteria for a particular diagnosis. What the individual is doing with regard to food and weight is neither normal nor healthy.

The $5\text{-HT}_{2C}$ receptor plays a role in Alzheimer Disease (AD). Therapeutic agents currently prescribed for Alzheimer's disease (AD) are cholinomimetic agents that act by inhibiting the enzyme acetylcholinesterase. The resulting effect is increased levels of acetylcholine, which modestly improves neuronal function and cognition in patients with AD. Although, dysfunction of cholinergic brain neurons is an early manifestation of AD, attempts to slow the progression of the disease with these agents have had only modest success, perhaps because the doses that can be administered are limited by peripheral cholinergic side effects, such as tremors, nausea, vomiting, and dry mouth. In addition, as AD progresses, these agents tend to lose their effectiveness due to continued cholinergic neuronal loss.

Therefore, there is a need for agents that have beneficial effects in AD, particularly in alleviating symptoms by improving cognition and slowing or inhibiting disease progression, without the side effects observed with current therapies. Therefore, serotonin $5\text{-HT}_{2C}$ receptors, which are exclusively expressed in brain, are attractive targets.

Another disease, disorder or condition that can is associated with the function of the $5\text{-HT}_{2C}$ receptor is erectile dysfunction (ED). Erectile dysfunction is the inability to achieve or maintain an erection sufficiently rigid for intercourse, ejaculation, or both. An estimated 20-30 million men in the United States have this condition at some time in their lives. The prevalence of the condition increases with age. Five percent of men 40 years of age report ED. This rate increases to between 15% and 25% by the age of 65, and to 55% in men over the age of 75 years.

Erectile dysfunction can result from a number of distinct problems. These include loss of desire or libido, the inability to maintain an erection, premature ejaculation, lack of emission, and inability to achieve an orgasm. Frequently, more than one of these problems presents themselves simultaneously. The conditions may be secondary to other disease states (typically chronic conditions), the result of specific disorders of the urogenital system or endocrine system, secondary to treatment with pharmacological agents (e.g. antihypertensive drugs, antidepressant drugs, antipsychotic drugs, etc.) or the result of psychiatric problems. Erectile dysfunction, when organic, is primarily due to vascular irregularities associated with atherosclerosis, diabetes, and hypertension.

There is evidence for use of a serotonin $5\text{-HT}_{2C}$ agonist for the treatment of sexual dysfunction in males and females. The serotonin $5\text{-HT}_{2C}$ receptor is involved with the processing and integration of sensory information, regulation of central monoaminergic systems, and modulation of neuroendocrine responses, anxiety, feeding behavior, and cerebrospinal fluid production [Tecott, L. H., et al. *Nature* 374: 542-546 (1995)]. In addition, the serotonin $5\text{-HT}_{2C}$ receptor has been implicated in the mediation of penile erections in rats, monkeys, and humans.

In summary, the $5\text{-HT}_{2C}$ receptor is a validated and well-accepted receptor target for the prophylaxis and/or treatment of $5\text{-HT}_{2C}$ mediated receptor diseases and disorders, such as, obesity, eating disorders, psychiatric disorders, Alzheimer Disease, sexual dysfunction and disorders related thereto. It can be seen that there exists a need for selective $5\text{-HT}_{2C}$ receptor agonists that can safely address these needs. The present invention is directed to these, as well as other, important ends.

One aspect of the present invention pertains to methods for weight management, comprising administering to an individual in need thereof, a therapeutically effective amount of a salt, a pharmaceutical composition, or a dosage form of the present invention.

One aspect of the present invention pertains to methods for weight management, comprising administering to an individual in need thereof, a therapeutically effective amount of a salt or a pharmaceutical composition of the present invention.

In some embodiments, the weight management comprises weight loss.

In some embodiments, the weight management comprises maintenance of weight loss.

In some embodiments, the weight management comprises decreased food consumption.

In some embodiments, the weight management comprises increasing meal-related satiety.

In some embodiments, the weight management comprises reducing pre-meal hunger.

In some embodiments, the weight management comprises reducing intra-meal food intake.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual in need of weight management is an obese patient with an initial body mass index $\geq 30$ kg/m$^2$.

In some embodiments, the individual in need of weight management is an overweight patient with an initial body mass index ≥27 kg/m² in the presence of at least one weight related comorbid condition.

In some embodiments, the individual in need of weight management is an overweight patient with an initial body mass index ≥27 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥30 kg/m².

In some embodiments, the individual in need of weight management has an initial body mass index ≥27 kg/m².

In some embodiments, the individual in need of weight management has an initial body mass index ≥27 kg/m² in the presence of at least one weight related comorbid condition.

In some embodiments, the individual in need of weight management has an initial body mass index ≥27 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥25 kg/m².

In some embodiments, the individual in need of weight management has an initial body mass index ≥25 kg/m² in the presence of at least one weight related comorbid condition.

In some embodiments, the individual in need of weight management has an initial body mass index ≥25 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 20 kg/m² in the presence of at least one weight related comorbid condition.

In some embodiments, the individual in need of weight management has an initial body mass index ≥about 20 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 21 kg/m² in the presence of at least one weight related comorbid condition.

In some embodiments, the individual in need of weight management has an initial body mass index ≥about 21 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 22 kg/m² in the presence of at least one weight related comorbid condition.

In some embodiments, the individual in need of weight management has an initial body mass index ≥about 22 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 23 kg/m² in the presence of at least one weight related comorbid condition.

In some embodiments, the individual in need of weight management has an initial body mass index ≥about 23 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 24 kg/m² in the presence of at least one weight related comorbid condition.

In some embodiments, the individual in need of weight management has an initial body mass index ≥about 24 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 25 kg/m² in the presence of at least one weight related comorbid condition.

In some embodiments, the individual in need of weight management has an initial body mass index ≥about 25 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 26 kg/m² in the presence of at least one weight related comorbid condition.

In some embodiments, the individual in need of weight management has an initial body mass index ≥about 26 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 27 kg/m² in the presence of at least one weight related comorbid condition.

In some embodiments, the individual in need of weight management has an initial body mass index ≥about 27 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 28 kg/m² in the presence of at least one weight related comorbid condition.

In some embodiments, the individual in need of weight management has an initial body mass index ≥about 28 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 29 kg/m² in the presence of at least one weight related comorbid condition.

In some embodiments, the individual in need of weight management has an initial body mass index ≥about 29 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 30 kg/m² in the presence of at least one weight related comorbid condition.

In some embodiments, the individual in need of weight management has an initial body mass index ≥about 30 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 31 kg/m² in the presence of at least one weight related comorbid condition.

In some embodiments, the individual in need of weight management has an initial body mass index ≥about 31 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 32 kg/m² in the presence of at least one weight related comorbid condition.

In some embodiments, the individual in need of weight management has an initial body mass index ≥about 32 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 33 kg/m² in the presence of at least one weight related comorbid condition.

In some embodiments, the individual in need of weight management has an initial body mass index ≥about 33 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 34 kg/m² in the presence of at least one weight related comorbid condition.

In some embodiments, the individual in need of weight management has an initial body mass index ≥about 34 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 35 kg/m² in the presence of at least one weight related comorbid condition.

In some embodiments, the individual in need of weight management has an initial body mass index ≥about 35 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 36 kg/m² in the presence of at least one weight related comorbid condition.

In some embodiments, the individual in need of weight management has an initial body mass index ≥about 36 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 37 kg/m² in the presence of at least one weight related comorbid condition.

In some embodiments, the individual in need of weight management has an initial body mass index ≥about 37 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 38 kg/m² in the presence of at least one weight related comorbid condition.

In some embodiments, the individual in need of weight management has an initial body mass index ≥about 38 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 39 kg/m² in the presence of at least one weight related comorbid condition.

In some embodiments, the individual in need of weight management has an initial body mass index ≥about 39 kg/m² in the presence of at least one weight related comorbid condition selected from: hypertension, dyslipidemia, cardiovascular disease, glucose intolerance, and sleep apnea.

In some embodiments, the individual in need of weight management has an initial body mass index ≥about 40 kg/m² in the presence of at least one weight related comorbid condition.

In some embodiments, the individual in need of weight management has an initial body mass index ≥about 40 kg/m² in the presence of at least one weight related comorbid condition selected from: hypertension, dyslipidemia, cardiovascular disease, glucose intolerance, and sleep apnea.

In some embodiments, the method for weight management further comprises administering phentermine to the individual.

One aspect of the present invention pertains to methods for the treatment of a disorder related to 5-HT$_{2C}$ receptor activity in an individual, comprising administering to an individual in need thereof, a therapeutically effective amount of a salt or a pharmaceutical composition of the present invention.

One aspect of the present invention pertains to methods for the treatment of obesity, comprising administering to an individual in need thereof, a therapeutically effective amount of a salt or a pharmaceutical composition of the present invention.

In some embodiments, the method for the treatment of obesity further comprises the administration or prescription of phentermine.

In some embodiments, the method for the treatment of obesity further comprises gastric electrical stimulation.

One aspect of the present invention pertains to methods for inducing weight loss, BMI loss, waist circumference loss or body fat percentage loss, comprising administering to an individual in need thereof, a therapeutically effective amount of a salt or a pharmaceutical composition of the present invention.

One aspect of the present invention pertains to methods for inducing weight loss, BMI loss, waist circumference loss or body fat percentage loss in an individual in preparation of the individual for bariatric surgery, comprising administering to an individual in need thereof, a therapeutically effective amount of a salt or a pharmaceutical composition of the present invention.

One aspect of the present invention pertains to methods for maintaining weight loss, BMI loss, waist circumference loss or body fat percentage loss in an individual, comprising administering to an individual in need thereof, a therapeutically effective amount of a salt or a pharmaceutical composition of the present invention.

One aspect of the present invention pertains to methods for maintaining weight loss, BMI loss, waist circumference loss or body fat percentage loss in an individual following bariatric surgery, comprising administering to an individual in need thereof, a therapeutically effective amount of a salt or a pharmaceutical composition of the present invention.

One aspect of the present invention pertains to methods for inducing satiety in an individual, comprising administering to an individual in need thereof, a therapeutically effective amount of a salt or a pharmaceutical composition of the present invention.

One aspect of the present invention pertains to methods for decreasing food intake in an individual, comprising administering to an individual in need thereof, a therapeutically effective amount of a salt or a pharmaceutical composition of the present invention.

One aspect of the present invention pertains to methods for decreasing hunger in an individual, comprising administering to an individual in need thereof, a therapeutically effective amount of a salt or a pharmaceutical composition of the present invention.

One aspect of the present invention pertains to methods for decreasing food cravings in an individual, comprising administering to an individual in need thereof, a therapeutically effective amount of a salt or a pharmaceutical composition of the present invention.

One aspect of the present invention pertains to methods for increasing intermeal interval in an individual, comprising administering to an individual in need thereof, a therapeutically effective amount of a salt or a pharmaceutical composition of the present invention.

One aspect of the present invention pertains to methods for the treatment of a disorder selected from: schizophrenia, anxiety, depression, psychoses and alcohol addiction, comprising administering to an individual in need thereof, a therapeutically effective amount of a salt or a pharmaceutical composition of the present invention.

In some embodiments, the disorder is schizophrenia.

In some embodiments, the disorder is anxiety.

In some embodiments, the disorder is depression.

In some embodiments, the disorder is psychoses.

In some embodiments, the disorder is alcohol addiction.

One aspect of the present invention pertains to the use of salts of the present invention, in the manufacture of a medicament for weight management in an individual.

In some embodiments, the weight management comprises weight loss.

In some embodiments, the weight management comprises maintenance of weight loss.

In some embodiments, the weight management comprises decreased food consumption.

In some embodiments, the weight management comprises increasing meal-related satiety.

In some embodiments, the weight management comprises reducing pre-meal hunger.

In some embodiments, the weight management comprises reducing intra-meal food intake.

In some embodiments, the weight management further comprises a reduced-calorie diet.

In some embodiments, the weight management further comprises a program of regular exercise.

In some embodiments, the weight management further comprises both a reduced-calorie diet and a program of regular exercise.

In some embodiments, the individual is an obese patient with an initial body mass index ≥30 kg/m$^2$.

In some embodiments, the individual is an overweight patient with an initial body mass index ≥27 kg/m$^2$ in the presence of at least one weight related comorbid condition.

In some embodiments, the individual is an overweight patient with an initial body mass index ≥27 kg/m$^2$ in the presence of at least one weight related comorbid condition selected from: hypertension, dyslipidemia, cardiovascular disease, glucose intolerance, and sleep apnea.

In some embodiments, the individual has an initial body mass index ≥30 kg/m$^2$.

In some embodiments, the individual has an initial body mass index ≥27 kg/m$^2$.

In some embodiments, the individual has an initial body mass index ≥27 kg/m$^2$ in the presence of at least one weight related comorbid condition.

In some embodiments, the individual has an initial body mass index ≥27 kg/m$^2$ in the presence of at least one weight related comorbid condition selected from: hypertension, dyslipidemia, cardiovascular disease, glucose intolerance, and sleep apnea.

In some embodiments, the individual has an initial body mass index ≥25 kg/m$^2$.

In some embodiments, the individual has an initial body mass index ≥25 kg/m$^2$ in the presence of at least one weight related comorbid condition.

In some embodiments, the individual has an initial body mass index ≥25 kg/m$^2$ in the presence of at least one weight related comorbid condition selected from: hypertension, dyslipidemia, cardiovascular disease, glucose intolerance, and sleep apnea.

In some embodiments, the medicament for weight management is used in combination with phentermine.

One aspect of the present invention pertains to the use of salts of the present invention, in the manufacture of a medicament for a disorder related to 5-HT$_{2C}$ receptor activity in an individual.

One aspect of the present invention pertains to the use of salts of the present invention, in the manufacture of a medicament for the treatment of obesity in an individual.

In some embodiments, the treatment of obesity further comprises the administration or prescription of phentermine.

In some embodiments, the treatment of obesity further comprises gastric electrical stimulation.

One aspect of the present invention pertains to the use of salts of the present invention, in the manufacture of a medicament for inducing weight loss, BMI loss, waist circumference loss or body fat percentage loss in an individual.

One aspect of the present invention pertains to the use of salts of the present invention, in the manufacture of a medicament for inducing weight loss, BMI loss, waist circumference loss or body fat percentage loss in an individual in preparation of the individual for bariatric surgery.

One aspect of the present invention pertains to the use of salts of the present invention, in the manufacture of a medicament for maintaining weight loss, BMI loss, waist circumference loss or body fat percentage loss in an individual.

One aspect of the present invention pertains to the use of salts of the present invention, in the manufacture of a medicament for maintaining weight loss, BMI loss, waist circumference loss or body fat percentage loss in an individual following bariatric surgery.

One aspect of the present invention pertains to the use of salts of the present invention, in the manufacture of a medicament for inducing satiety in an individual.

One aspect of the present invention pertains to the use of salts, or crystalline forms of the present invention, in the manufacture of a medicament for decreasing food intake in an individual.

One aspect of the present invention pertains to the use of salts of the present invention, in the manufacture of a medicament for decreasing hunger in an individual.

One aspect of the present invention pertains to the use of salts of the present invention, in the manufacture of a medicament for decreasing food cravings in an individual.

One aspect of the present invention pertains to the use of salts of the present invention, in the manufacture of a medicament for increasing intermeal interval in an individual.

One aspect of the present invention pertains to the use of salts of the present invention, in the manufacture of a medicament for the treatment of a disorder selected from: schizophrenia, anxiety, depression, psychoses and alcohol addiction in an individual.

In some embodiments, the disorder is schizophrenia.
In some embodiments, the disorder is anxiety.
In some embodiments, the disorder is depression.
In some embodiments, the disorder is psychoses.
In some embodiments, the disorder is alcohol addiction.

One aspect of the present invention pertains to salts of the present invention, for use in a method of treatment of a disorder related to 5-$HT_{2C}$ receptor activity in an individual.

One aspect of the present invention pertains to salts of the present invention, for use in a method of treatment of obesity in an individual.

In some embodiments, the method of treatment of obesity further comprises the administration or prescription of phentermine.

In some embodiments, the method of treatment of obesity further comprises gastric electrical stimulation.

One aspect of the present invention pertains to salts of the present invention, for use in a method of inducing weight loss, BMI loss, waist circumference loss or body fat percentage loss in an individual.

One aspect of the present invention pertains to salts of the present invention, for use in a method of inducing weight loss, BMI loss, waist circumference loss or body fat percentage loss in an individual in preparation of the individual for bariatric surgery.

One aspect of the present invention pertains to salts of the present invention, for use in a method of maintaining weight loss, BMI loss, waist circumference loss or body fat percentage loss in an individual.

One aspect of the present invention pertains to salts of the present invention, for use in a method of maintaining weight loss, BMI loss, waist circumference loss or body fat percentage loss in an individual following bariatric surgery.

One aspect of the present invention pertains to salts of the present invention, for use in a method of inducing satiety in an individual.

One aspect of the present invention pertains to salts of the present invention, for use in a method of decreasing food intake in an individual.

One aspect of the present invention pertains to salts of the present invention, for use in a method of decreasing hunger in an individual.

One aspect of the present invention pertains to salts of the present invention, for use in a method of decreasing food cravings in an individual.

One aspect of the present invention pertains to salts of the present invention, for use in a method of increasing intermeal interval in an individual.

One aspect of the present invention pertains to salts of the present invention, for use in a method of treatment of a disorder selected from: schizophrenia, anxiety, depression, psychoses and alcohol addiction in an individual.

In some embodiments, the disorder is schizophrenia.
In some embodiments, the disorder is anxiety.
In some embodiments, the disorder is depression.
In some embodiments, the disorder is psychoses.
In some embodiments, the disorder is alcohol addiction.

One aspect of the present invention pertains to salts and pharmaceutical compositions of the present invention, for use in a method of treatment of the human or animal body by therapy.

One aspect of the present invention pertains to salts and pharmaceutical compositions of the present invention, for use in a method of weight management.

One aspect of the present invention pertains to salts and pharmaceutical compositions of the present invention, for use in a method of weight loss.

One aspect of the present invention pertains to salts and pharmaceutical compositions of the present invention, for use in a method of maintenance of weight loss.

One aspect of the present invention pertains to salts and pharmaceutical compositions of the present invention, for use in a method of decreasing food consumption.

One aspect of the present invention pertains to salts and pharmaceutical compositions of the present invention, for use in a method of increasing meal-related satiety.

One aspect of the present invention pertains to salts and pharmaceutical compositions of the present invention, for use in a method of reducing pre-meal hunger.

One aspect of the present invention pertains to salts and pharmaceutical compositions of the present invention, for use in a method of reducing intra-meal food intake.

One aspect of the present invention pertains to salts and pharmaceutical compositions of the present invention, for use in a method of weight management further comprising a reduced-calorie diet.

One aspect of the present invention pertains to salts and pharmaceutical compositions of the present invention, for use in a method of weight management further comprising a program of regular exercise.

One aspect of the present invention pertains to salts and pharmaceutical compositions of the present invention, for use in a method of weight management further comprising a reduced-calorie diet and a program of regular exercise.

One aspect of the present invention pertains to salts and pharmaceutical compositions of the present invention, for use in a method of weight management in an obese patient with an initial body mass index ≥30 kg/m².

One aspect of the present invention pertains to salts and pharmaceutical compositions of the present invention, for use in a method of weight management in an overweight patient with an initial body mass index ≥27 kg/m² in the presence of at least one weight related co-morbid condition.

One aspect of the present invention pertains to salts and pharmaceutical compositions of the present invention, for use in a method of weight management in an overweight patient with an initial body mass index ≥27 kg/m² in the presence of at least one weight related co-morbid condition selected from: hypertension, dyslipidemia, cardiovascular disease, glucose intolerance, and sleep apnea.

One aspect of the present invention pertains to salts and pharmaceutical compositions of the present invention, for use in a method of weight management in an individual with an initial body mass index ≥30 kg/m².

One aspect of the present invention pertains to salts and pharmaceutical compositions of the present invention, for use in a method of weight management in an individual with an initial body mass index ≥27 kg/m².

One aspect of the present invention pertains to salts and pharmaceutical compositions of the present invention, for use in a method of weight management in an individual with an initial body mass index ≥27 kg/m² in the presence of at least one weight related co-morbid condition.

One aspect of the present invention pertains to salts and pharmaceutical compositions of the present invention, for use in a method of weight management in an individual with an initial body mass index ≥27 kg/m² in the presence of at least one weight related co-morbid condition selected from: hypertension, dyslipidemia, cardiovascular disease, glucose intolerance, and sleep apnea.

One aspect of the present invention pertains to salts and pharmaceutical compositions of the present invention, for use in a method of weight management in an individual with an initial body mass index ≥25 kg/m².

One aspect of the present invention pertains to salts and pharmaceutical compositions of the present invention, for use in a method of weight management in an individual with an initial body mass index ≥25 kg/m² in the presence of at least one weight related co-morbid condition.

One aspect of the present invention pertains to salts and pharmaceutical compositions of the present invention, for use in a method of weight management in an individual with an initial body mass index ≥25 kg/m² in the presence of at least one weight related co-morbid condition selected from: hypertension, dyslipidemia, cardiovascular disease, glucose intolerance, and sleep apnea.

One aspect of the present invention pertains to salts and pharmaceutical compositions of the present invention, for use in a method of weight management in combination with phentermine.

One aspect of the present invention pertains to salts and pharmaceutical compositions of the present invention, for use in a method of treatment of a disorder related to $5\text{-HT}_{2C}$ receptor activity in an individual.

One aspect of the present invention pertains to salts and pharmaceutical compositions of the present invention, for use in a method of treatment of obesity in an individual.

In some embodiments, the method of treatment of obesity further comprises the administration or prescription of phentermine.

In some embodiments, the method of treatment of obesity further comprises gastric electrical stimulation.

One aspect of the present invention pertains to salts and pharmaceutical compositions of the present invention, for use in a method of inducing weight loss, BMI loss, waist circumference loss or body fat percentage loss in an individual.

One aspect of the present invention pertains to salts and pharmaceutical compositions of the present invention, for use in a method of inducing weight loss, BMI loss, waist circumference loss or body fat percentage loss in an individual in preparation of the individual for bariatric surgery.

One aspect of the present invention pertains to salts and pharmaceutical compositions of the present invention, for use in a method of maintaining weight loss, BMI loss, waist circumference loss or body fat percentage loss in an individual.

One aspect of the present invention pertains to salts and pharmaceutical compositions of the present invention, for use in a method of maintaining weight loss, BMI loss, waist circumference loss or body fat percentage loss in an individual following bariatric surgery.

One aspect of the present invention pertains to salts and pharmaceutical compositions of the present invention, for use in a method of inducing satiety in an individual.

One aspect of the present invention pertains to salts and pharmaceutical compositions of the present invention, for use in a method of decreasing food intake in an individual.

One aspect of the present invention pertains to salts and pharmaceutical compositions of the present invention, for use in a method of decreasing hunger in an individual.

One aspect of the present invention pertains to salts and pharmaceutical compositions of the present invention, for use in a method of decreasing food cravings in an individual.

One aspect of the present invention pertains to salts and pharmaceutical compositions of the present invention, for use in a method of increasing intermeal interval in an individual.

One aspect of the present invention pertains to salts and pharmaceutical compositions of the present invention, for use in a method of treatment of a disorder selected from: schizophrenia, anxiety, depression, psychoses and alcohol addiction in an individual.

In some embodiments, the disorder is schizophrenia.

In some embodiments, the disorder is anxiety.

In some embodiments, the disorder is depression.

In some embodiments, the disorder is psychoses.

In some embodiments, the disorder is alcohol addiction.

One aspect of the present invention pertains to methods for weight management, comprising administering to an individual in need thereof, a therapeutically effective amount of a salt or a pharmaceutical composition of the present invention.

In some embodiments, the weight management comprises one or more of: weight loss, maintenance of weight loss, decreased food consumption, increasing meal-related satiety, reducing pre-meal hunger, and reducing intra-meal food intake.

In some embodiments, the weight management is as an adjunct to diet and exercise.

In some embodiments, the individual in need of weight management is selected from: an obese patient with an initial body mass index ≥30 kg/m²; an overweight patient with an initial body mass index ≥27 kg/m² in the presence of at least one weight related comorbid condition; an overweight patient with an initial body mass index ≥27 kg/m² in the presence of at least one weight related comorbid condition; wherein the weight related co-morbid condition is selected from: hypertension, dyslipidemia, cardiovascular disease, glucose intolerance, and sleep apnea.

In some embodiments, the method further comprises administering a second anti-obesity agent to the individual.

In some embodiments, the second anti-obesity agent is selected from: chlorphentermine, clortermine, phenpentermine, and phentermine, and pharmaceutically acceptable salts, solvates, and hydrates thereof.

In some embodiments, the method further comprises administering an anti-diabetes agent to the individual.

In some embodiments, the anti-diabetes agent is metformin.

One aspect of the present invention pertains to uses of a salt of the present invention, in the manufacture of a medicament for weight management in an individual.

In some embodiments, the weight management comprises one or more of: weight loss, maintenance of weight loss, decreased food consumption, increasing meal-related satiety, reducing pre-meal hunger, and reducing intra-meal food intake.

In some embodiments, the medicament is used as an adjunct to diet and exercise.

In some embodiments, the individual in need of weight management is selected from:
an obese patient with an initial body mass index ≥30 kg/m²; an overweight patient with an initial body mass index ≥27 kg/m² in the presence of at least one weight related comorbid condition; and an overweight patient with an initial body mass index ≥27 kg/m² in the presence of at least one weight related comorbid condition; wherein the weight related comorbid condition is selected from: hypertension, dyslipidemia, cardiovascular disease, glucose intolerance, and sleep apnea.

In some embodiments, the medicament is used in combination with a second anti-obesity agent.

In some embodiments, the second anti-obesity agent is selected from: chlorphentermine, clortermine, phenpentermine, and phentermine, and pharmaceutically acceptable salts, solvates, and hydrates thereof.

In some embodiments, the medicament is used in combination with an anti-diabetes agent.

In some embodiments, the medicament is used in combination with an anti-diabetes agent; wherein the anti-diabetes agent is metformin.

One aspect of the present invention pertains to salts and pharmaceutical compositions of the present invention, for use in a method of treatment of the human or animal body by therapy.

One aspect of the present invention pertains to salts and pharmaceutical compositions of the present invention, for use in a method of weight management.

One aspect of the present invention pertains to salts and pharmaceutical compositions of the present invention, for use in a method of weight management; wherein the weight management comprises one or more of: weight loss, maintenance of weight loss, decreased food consumption, increasing meal-related satiety, reducing pre-meal hunger, and reducing intra-meal food intake.

One aspect of the present invention pertains to salts and pharmaceutical compositions of the present invention, for use as an adjunct to diet and exercise for weight management.

One aspect of the present invention pertains to salts and pharmaceutical compositions of the present invention, for use in a method of weight management; wherein the individual in need of weight management is selected from: an obese patient with an initial body mass index ≥30 kg/m$^2$; an overweight patient with an initial body mass index ≥27 kg/m$^2$ in the presence of at least one weight related comorbid condition; and an overweight patient with an initial body mass index ≥27 kg/m$^2$ in the presence of at least one weight related comorbid condition; wherein the weight related co-morbid condition is selected from: hypertension, dyslipidemia, cardiovascular disease, glucose intolerance, and sleep apnea.

One aspect of the present invention pertains to salts and pharmaceutical compositions of the present invention, for use in a method of weight management in combination with a second anti-obesity agent.

One aspect of the present invention pertains to salts and pharmaceutical compositions of the present invention, for use in a method of weight management in combination with a second anti-obesity agent selected from: chlorphentermine, clortermine, phenpentermine, and phentermine, and pharmaceutically acceptable salts, solvates, and hydrates thereof.

One aspect of the present invention pertains to salts and pharmaceutical compositions of the present invention, for use in a method of weight management in combination with an anti-diabetes agent; wherein the anti-diabetes agent is metformin.

Combination Therapies

The salts of the present invention can be used in combination with suitable pharmaceutical agents.

In some embodiments the salts of the present invention can be used in combination with a second anti-obesity agent. Anti-obesity agents include, for example, adrenergic reuptake inhibitors, apolipoprotein-B secretion/microsomal triglyceride transfer protein inhibitors, β3 adrenergic receptor agonists, bombesin agonists, cannabinoid 1 receptor antagonists, cholescystokinin-A agonists, ciliary neutrotrophic factors, dopamine agonists, galanin antagonists, ghrelin receptor antagonists, glucagon-like peptide-1 receptor agonists, glucocorticoid receptor agonists or antagonists, histamine-3 receptor antagonists or reverse agonists, human agouti-related proteins, leptin receptor agonists, lipase inhibitors, MCR-4 agonists, melanin concentrating hormone antagonists, melanocyte-stimulating hormone receptor analogs, monoamine reuptake inhibitors, neuromedin U receptor agonists, neuropeptide-Y antagonists, orexin receptor antagonists, stimulants, sympathomimetic agents, thyromimetic agents, and urocortin binding protein antagonists.

In some embodiments, the second anti-obesity agent is selected from: 4-methylamphetamine, 5-HTP, amfecloral, amfepentorex, amfepramone, aminorex, amphetamine, amphetaminil, atomoxetine, benfluorex, benzphetamine, bromocriptine, bupropion, cathine, cathinone, cetilistat, chlorphentermine, ciclazindol, clobenzorex, cloforex, clominorex, clortermine, dapiclermin, dehydroepiandrosterone, dehydroepiandrosterone analogues, dexmethylphenidate, dextroamphetamine, dextromethamphetamine, difemetorex, dimethylcathinone, dinitrophenol, diphemethoxidine, ephedra, ephedrine, ethylamphetamine, etolorex, fenbutrazate, fencamfamine, fenethylline, fenproporex, fludorex, fluminorex, furfenorex, galactomannan, glucomannan, ibipinabant, indanorex, khat, L-dopa, leptin, a leptin analog, levopropylhexedrine, lisdexamfetamine, L-phenylalanine, L-tryptophan, L-tyrosine, N-[[trans-4-[(4,5-dihydro[1]benzothiepino[5,4-d]thiazol-2-yl)amino]cyclohexyl]methyl] methanesulfonamide, manifaxine, mazindol, mefenorex, metformin, methamphetamine, methylphenidate, naloxone, naltrexone, oleoyl-estrone, orlistat, otenabant, oxyntomodulin, P57, pemoline, peptide YY, phendimetrazine, phenethylamine, phenmetrazine, phenpentermine, phentermine, phenylpropanolamine, pipradrol, prolintane, propylhexedrine, pseudoephedrine, pyrovalerone, radafaxine, reboxetine, rimonabant, setazindol, sibutramine, simmondsin, sterculia, surinabant, synephrine, taranabant, tesofensine, topiramate, viloxazine, xylopropamine, yohimbine, zonisamide, and zylofuramine, and pharmaceutically acceptable salts, solvates, and hydrates thereof.

In some embodiments, the second anti-obesity agent is selected from: 4-methylamphetamine, amfecloral, amfepentorex, amfepramone, aminorex, amphetamine, amphetaminil, atomoxetine, benfluorex, benzphetamine, bupropion, cathine, cathinone, chlorphentermine, ciclazindol, clobenzorex, cloforex, clominorex, clortermine, dexmethylphenidate, dextroamphetamine, dextromethamphetamine, difemetorex, dimethylcathinone, diphemethoxidine, ephedra, ephedrine, ethylamphetamine, etolorex, fenbutrazate, fencamfamine, fenethylline, fenproporex, fludorex, fluminorex, furfenorex, indanorex, khat, levopropylhexedrine, lisdexamfetamine, manifaxine, mazindol, mefenorex, methamphetamine, methylphenidate, pemoline, phendimetrazine, phenethylamine, phenmetrazine, phenpentermine, phentermine, phenylpropanolamine, pipradrol, prolintane, propylhexedrine, pseudoephedrine, pyrovalerone, radafaxine, reboxetine, setazindol, sibutramine, synephrine, taranabant, tesofensine, viloxazine, xylopropamine, and zylofuramine, and pharmaceutically acceptable salts, solvates, and hydrates thereof.

In some embodiments, the second anti-obesity agent is selected from: chlorphentermine, clortermine, phenpentermine, and phentermine, and pharmaceutically acceptable salts, solvates, and hydrates thereof.

In some embodiments the salts of the present invention can be used in combination with an anti-diabetes agent. Anti-diabetes agents include, for example, DPP-IV inhibitors, biguanides, alpha-glucosidase inhibitors, insulin analogues, sulfonylureas, SGLT2 inhibitors, meglitinides, thiazolidinediones, anti-diabetic peptide analogues, and GPR119 agonists.

In some embodiments, the anti-diabetes agent is selected from: sitagliptin, vildagliptin, saxagliptin, alogliptin, linagliptin, phenformin, metformin, buformin, proguanil, acarbose, miglitol, voglibose, tolbutamide, acetohexamide, tolazamide, chlorpropamide, glipizide, glibenclamide, glimepiride, gliclazide, dapagliflozin, remigliflozin, sergliflozin, and 4-[6-(6-methanesulfonyl-2-methyl-pyridin-3-ylamino)-5-methoxy-pyrimidin-4-yloxy]-piperidine-1-carboxylic acid isopropyl ester.

In some embodiments, the anti-diabetes agent is a DPP-IV inhibitor selected from the following compounds and pharmaceutically acceptable salts, solvates, and hydrates thereof: 3(R)-amino-1-[3-(trifluoromethyl)-5,6,7,8-tetrahydro[1,2,4]triazolo[4,3-a]pyrazin-7-yl]-4-(2,4,5-trifluorophenyl)butan-1-one; 1-[2-(3-hydroxyadamant-1-ylamino)acetyl]pyrrolidine-2(S)-carbonitrile; (1S,3S,5S)-2-[2(S)-amino-2-(3-hydroxyadamantan-1-yl)acetyl]-2-azabicyclo[3.1.0]hexane-3-carbonitrile; 2-[6-[3(R)-aminopiperidin-1-yl]-3-methyl-2,4-dioxo-1,2,3,4-tetrahydropyrimidin-1-ylmethyl]benzonitrile; 8-[3(R)-aminopiperidin-1-yl]-7-(2-butynyl)-3-methyl-1-(4-methylquinazolin-2-ylmethyl)xanthine; 1-[N-[3(R)-pyrrolidinyl]glycyl]pyrrolidin-2(R)-yl boronic acid; 4(S)-fluoro-1-[2-[(1R,3S)-3-(1H-1,2,4-triazol-1-ylmethyl)cyclopentylamino]acetyl]pyrrolidine-2(S)-carbonitrile; 1-[(2S,3S,11bS)-2-amino-9,10-dimethoxy-2,3,4,6,7,11b-hexahydro-1H-pyrido[2,1-a]isoquinolin-3-yl]-4(S)-(fluoromethyl)pyrrolidin-2-one; (2S,4S)-2-cyano-4-fluoro-1-[(2-hydroxy-1,1-dimethyl) ethylamino]acetylpyrrolidine; 8-(cis-hexahydro-pyrrolo[3,2-b]pyrrol-1-yl)-3-methyl-7-(3-methyl-but-2-enyl)-1-(2-oxo-2-phenylethyl)-3,7-dihydro-purine-2,6-dione; 1-((3S,4S)-4-amino-1-(4-(3,3-difluoropyrrolidin-1-yl)-1,3,5-triazin-2-yl)pyrrolidin-3-yl)-5,5difluoropiperidin-2-one; (R)-2-((6-(3-aminopiperidin-1-yl)-3-methyl-2,4-dioxo-3,4-dihydropyrimidin-1(2H)-yl)methyl)-4-fluorobenzonitrile; 5-{(S)-2-[2-((S)-2-cyano-pyrrolidin-1-yl)-2-oxo-ethylamino]-propyl}-5-(1H-tetrazol-5-yl)10,11-dihydro-5H-dibenzo[a,d]cycloheptene-2,8-dicarboxylic acid bis-dimethylamide; ((2S,4S)-4-(4-(3-methyl-1-phenyl-1H-pyrazol-5-yl)piperazin-1-yl)pyrrolidin-2-yl)(thiazolidin-3-yl)methanone; (2S,4S)-1-[2-[(4-ethoxycarbonylbicyclo[2.2.2]oct-1-yl)amino]acetyl]-4-fluoropyrrolidine-2-carbonitrile; 6-[(3R)-3-amino-piperidin-1-yl]-5-(2-chloro-5-fluoro-benzyl)-1,3-dimethyl-1,5dihydro-pyrrolo[3,2-d]pyrimidine-2,4-dione; 2-({6-[(3R)-3-amino-3-methylpiperidin-1-yl]-1,3-dimethyl-2,4-dioxo-1,2,3,4-tetrahydro-5H-pyrrolo[3,2-d]pyrimidin-5-yl}methyl)-4-fluorobenzonitrile; (2S)-1-{[2-(5-methyl-2-phenyl-oxazol-4-yl)-ethylamino]-acetyl}-pyrrolidine-2-carbonitrile; (2S)-1-{[1,1-dimethyl-3-(4-pyridin-3-yl-imidazol-1-yl)-propylamino]-acetyl}-pyrrolidine-2-carbonitrile; (3,3-difluoropyrrolidin-1-yl)-((2S,4S)-4-(4-(pyrimidin-2-yl)piperazin-1-yl)pyrrolidin-2-yl)methanone; (2S,4S)-1-[(2S)-2-amino-3,3-bis(4-fluorophenyl)propanoyl]-4-fluoropyrrolidine-2-carbonitrile; (2S,5R)-5-ethynyl-1-{N-(4-methyl-1-(4-carboxy-pyridin-2-yl)piperidin-4-yl)glycyl}pyrrolidine-2-carbonitrile; and (1S,6R)-3-{[3-(trifluoromethyl)-5,6-dihydro[1,2,4]triazolo[4,3-a]pyrazin-7(8H)-yl]carbonyl}-6-(2,4,5-trifluorophenyl)cyclohex-3-en-1-amine.

In some embodiments, the anti-diabetes agent is an alpha-glucosidase inhibitor selected from the following compounds and pharmaceutically acceptable salts, solvates, and hydrates thereof: (2R,3R,4R,5R)-4-((2R,3R,4R,5S,6R)-5-((2R,3R,4S,5S,6R)-3,4-dihydroxy-6-methyl-5-((1S,4R,5S,6S)-4,5,6-trihydroxy-3-(hydroxymethyl)cyclohex-2-enylamino)tetrahydro-2H-pyran-2-yloxy)-3,4-dihydroxy-6-(hydroxymethyl)tetrahydro-2H-pyran-2-yloxy)-2,3,5,6-tetrahydroxyhexanal; (2R,3R,4R,5S)-1-(2-hydroxyethyl)-2-(hydroxymethyl)piperidine-3,4,5-triol; and (1S,2S,3R,4S,5S)-5-(1,3-dihydroxypropan-2-ylamino)-1-(hydroxymethyl)cyclohexane-1,2,3,4-tetraol.

In some embodiments, the anti-diabetes agent is a sulfonylurea selected from the following compounds and pharmaceutically acceptable salts, solvates, and hydrates thereof: N-(4-(N-(cyclohexylcarbamoyl)sulfamoyl)phenethyl)-5-methylpyrazine-2-carboxamide); 5-chloro-N-(4-(N-(cyclohexylcarbamoyl)sulfamoyl)phenethyl)-2-methoxybenzamide; and 3-ethyl-4-methyl-N-(4-(N-((1r,4r)-4-methylcyclohexylcarbamoyl)sulfamoyl)phenethyl)-2-oxo-2,5-dihydro-1H-pyrrole-1-carboxamide.

In some embodiments, the anti-diabetes agent is an SGLT2 inhibitor selected from the following compounds and pharmaceutically acceptable salts, solvates, and hydrates thereof: (2S,3R,4R,5S,6R)-2-(4-chloro-3-(4-ethoxybenzyl)phenyl)-6-(hydroxymethyl)tetrahydro-2H-pyran-3,4,5-triol; ethyl ((2R,3S,4S,5R,6S)-3,4,5-trihydroxy-6-(4-(4-isopropoxybenzyl)-1-isopropyl-5-methyl-1H-pyrazol-3-yloxy)tetrahydro-2H-pyran-2-yl)methyl carbonate; and ethyl ((2R,3S,4S,5R,6S)-3,4,5-trihydroxy-6-(2-(4-methoxybenzyl)phenoxy)tetrahydro-2H-pyran-2-yl)methyl carbonate.

In some embodiments, the anti-diabetes agent is a meglitinide selected from the following compounds and pharmaceutically acceptable salts, solvates, and hydrates thereof: (S)-2-ethoxy-4-(2-(3-methyl-1-(2-(piperidin-1-yl)phenyl)butylamino)-2-oxoethyl)benzoic acid; (R)-2-((1r,4R)-4-isopropylcyclohexanecarboxamido)-3-phenylpropanoic acid; and (S)-2-benzyl-4-((3aR,7aS)-1H-isoindol-2(3H,3aH,4H,5H,6H,7H,7aH)-yl)-4-oxobutanoic acid.

In some embodiments, the anti-diabetes agent is a biguanide selected from the following compounds and pharmaceutically acceptable salts, solvates, and hydrates thereof: metformin, phenformin, buformin, and proguanil.

In some embodiments, the anti-diabetes agent is metformin.

In some embodiments, the anti-diabetes agent is a GPR119 agonist selected from the GPR119 agonists disclosed in the following PCT applications: WO2006083491, WO 2008081204, WO2009123992, WO2010008739, WO2010029089, and WO2010149684.

In some embodiments, the anti-diabetes agent is 4-[6-(6-methanesulfonyl-2-methyl-pyridin-3-ylamino)-5-methoxy-pyrimidin-4-yloxy]-piperidine-1-carboxylic acid isopropyl ester.

In some embodiments, the anti-diabetes agent is 5-(4-(4-(3-fluoro-4-(methylsulfonyl)phenoxy)butan-2-yl)piperidin-1-yl)-3-isopropyl-1,2,4-oxadiazole.

Other anti-obesity agents, and anti-diabetes agents including the agents set forth infra, are well known, or will be readily apparent in light of the instant disclosure, to one of ordinary skill in the art. It will be understood that the scope of combination therapy of the salts of the present invention with other anti-obesity agents and with anti-diabetes agents is not limited to those listed above, but includes in principle any combination with any pharmaceutical agent or pharmaceutical composition useful for the treatment of overweight, obese, and diabetic individuals.

One aspect of the present invention pertains to salts of the present invention, characterized in that the salts is administered in conjunction with a second anti-obesity agent as described herein.

One aspect of the present invention pertains to salts of the present invention, characterized in that the salt is administered in conjunction with an anti-diabetes agent as described herein.

One aspect of the present invention pertains to salts of the present invention for use in combination with a second anti-obesity agent for use in weight management.

One aspect of the present invention pertains to salts of the present invention for use in combination with an anti-diabetes agent for use in weight management and the treatment of diabetes.

One aspect of the present invention pertains to methods of weight management in an individual in need thereof, comprising administering to the individual a salt of the present invention and a second anti-obesity agent wherein the salt and the second anti-obesity agent are administered to the individual simultaneously, separately, or sequentially.

One aspect of the present invention pertains to methods of weight management and treating diabetes in an individual in need thereof, comprising administering to the individual a salt of the present invention and an anti-diabetes agent wherein the salt and the anti-diabetes agent are administered to the individual simultaneously, separately, or sequentially.

One aspect of the present invention pertains to methods of weight management in an individual in need thereof, wherein the individual has been or is being treated with a second anti-obesity agent, the method comprising administering to the individual a therapeutically effective amount of a salt of the present invention.

One aspect of the present invention pertains to methods of weight management and treatment of diabetes in an individual in need thereof, wherein the individual has been or is being treated with an anti-diabetes agent, the method comprising administering to the individual a therapeutically effective amount of a salt of the present invention.

One aspect of the present invention pertains to anti-obesity agents, characterized in that the anti-obesity agent is administered in conjunction with a salt of the present invention.

One aspect of the present invention pertains to anti-diabetes agents, characterized in that the anti-diabetes agent is administered in conjunction with a salt of the present invention.

One aspect of the present invention pertains to anti-obesity agents for use in combination with a salt of the present invention for use in weight management.

One aspect of the present invention pertains to anti-diabetes agents for use in combination with a salt of the present invention for use in weight management and the treatment of diabetes.

One aspect of the present invention pertains to methods of weight management in an individual in need thereof, comprising administering to the individual an anti-obesity agent and a salt of the present invention wherein the anti-obesity agent and the salt are administered to the individual simultaneously, separately, or sequentially.

One aspect of the present invention pertains to methods of weight management and treating diabetes in an individual in need thereof, comprising administering to the individual an anti-diabetes agent and a salt of the present invention wherein the anti-diabetes agent and the salt are administered to the individual simultaneously, separately, or sequentially.

One aspect of the present invention pertains to methods of weight management in an individual in need thereof, wherein the individual has been or is being treated with a salt of the present invention, the method comprising administering to the individual a therapeutically effective amount of a second anti-obesity agent.

One aspect of the present invention pertains to methods of weight management and treatment of diabetes in an individual in need thereof, wherein the individual has been or is being treated with a salt of the present invention, the method comprising administering to the individual a therapeutically effective amount of an anti-diabetes agent.

The invention will be described in greater detail by way of specific examples. The following examples are offered for illustrative purposes, and are not intended to limit the invention in any manner. Those of skill in the art will readily recognize a variety of noncritical parameters which can be changed or modified to yield essentially the same results.

EXAMPLES

The following examples are provided to further define the invention without, however, limiting the invention to the particulars of these examples. The compounds and salts thereof described herein, supra and infra, are named according to the CS ChemDraw Ultra Version 7.0.1, AutoNom version 2.2, or CS ChemDraw Ultra Version 9.0.7. In certain instances common names are used and it is understood that these common names would be recognized by those skilled in the art.

Powder X-ray Diffraction (PXRD) studies were conducted using an X'Pert PRO MPD powder diffractometer (PANalytical, Inc.; EQ0233) with a Cu source set at 45 kV and 40 mA, Cu(Kα) radiation and an X'Celerator detector. Samples were placed on a PXRD sample plate either as-is or ground slightly to reduce the size of large particles or crystals. Data were collected with the samples spinning from 5° to 40° 2θ. Data were analyzed by X'Pert Data Viewer software, version 1.0a, to determine crystallinity and/or crystal form, and by X'Pert HighScore software, version 1.0b, to generate the tables of PXRD peaks.

Differential scanning calorimetry (DSC) studies were conducted using a TA Instruments, Q2000 (EQ1980) at heating rate 10° C./min. The instruments were calibrated by the vendor for temperature and energy using the melting point and enthalpy of fusion of an indium standard.

Thermogravimetric analyses (TGA) were conducted using a TA Instruments TGA Q5000 (EQ1982) at heating rate 10° C./min. The instrument was calibrated by the vendor using Alumel and Nickel Curie points for the furnace temperature and a standard weight for the balance.

Dynamic moisture-sorption (DMS) studies were conducted using a dynamic moisture-sorption analyzer, VTI Corporation, SGA-100, equipment #0228. Samples were prepared for DMS analysis by placing 5 mg to 20 mg of a sample in a tared sample holder. The sample was placed on the hang-down wire of the VTI balance. A drying step was run, typically at 40° C. and 0.5-1% RH for 1-2 h. The isotherm temperature is 25° C. Defined % RH holds typically ranged from 10% RH to 90% RH or 95% RH, with intervals of 10 to 20% RH. A % weight change smaller than 0.010% over a specified number of minutes (typically 10-20), or up to 2 h, whichever occurs first, is required before continuing to the next % RH hold. The water content of the sample equilibrated as described above was determined at each % RH hold.

If saturated in water with excess solid, a deliquescing compound or salt thereof equilibrated in a closed system at a given temperature produces a % RH in that closed system that is equal to its deliquescing % RH (DRH) at that temperature. Fractional relative humidity is equal to water activity ($a_w$) in the vapor phase and at equilibrium in a closed system, the $a_w$ in an aqueous solution is equal to the aw in the vapor phase above the solution (see Equation 1).

$$\frac{DRH}{100\%} = \frac{\% RH}{100\%} \text{(above enclosed } sat\ aq\ sol'n\ at\ equil\text{)} \quad \text{Equation 1}$$
$$= a_w\text{(vapor)}$$
$$= a_w\text{(liquid)}$$

A water activity meter was used to measure DRH for selected salts described herein. The instrument used for this study is a Decagon Devices AquaLab 4TE water activity meter, equipment #2169. This instrument is designed with temperature control and a small headspace above the enclosed sample to establish equilibrium between solution and vapor phases quickly. Measured $a_w$ values at 25° C. for samples of aqueous-saturated Compound 1 salts with excess solid were multiplied by 100% to get DRH values in % RH.

Acquity ultra performance liquid chromatography (UPLC) from Waters was used for solubility and stoichiometry determination. Instrument number is SY-EQ 1889. UPLC was equipped with Acquity PDA detector. UPLC mobile phase solvent A was 0.1% TFA in DI-water, solvent B was 0.1% TFA in acetonitrile. The mobile phase gradient as shown in the table below:

| Time (min) | Flow (mL/min) | % A | % B | Curve |
|---|---|---|---|---|
|  | 0.600 | 95.0 | 5.0 |  |
| 2.00 | 0.600 | 5.0 | 95.0 | 6 |
| 2.50 | 0.600 | 5.0 | 95.0 | 6 |
| 2.75 | 0.600 | 95.0 | 5.0 | 1 |
| 5.00 | 0.000 | 95.0 | 5.0 | 11 |

Column temperature was 40±5° C. Acquity UPLC® HSS T3 1.8 μm, 2.1×50 mm column was used.

A known amount of sample was dissolved in water and analyzed by UPLC. The weight percent of Compound 1 in the salt samples was determined by comparing the UV signal to that of a standard, Compound 1 hydrochloride salt hemihydrate, or Compound 1 free base. The percentage of Compound 1 or the percentage of the counterion determined was compared to the theoretical values to establish the stoichiometry.

Example 1

Preparation of Form I of (R)-8-Chloro-1-methyl-2,3,4,5-tetrahydro-1H-3-benzazepine (1S)-(+)-10-Camsylate Salt (Compound 1 (1S)-(+)-10-Camsylate Salt, Form I)

The title salt was prepared by the dropwise addition of 1 mole equivalent of ~3.6 M aqueous (1S)-(+)-10-camphorsulfonic acid to a solution of (R)-8-chloro-1-methyl-2,3,4,5-tetrahydro-1H-3-benzazepine in acetonitrile with vigorous stirring Immediate precipitation was observed and the solid was collected by filtration and washed with isopropyl alcohol.

The DRH of the title salt was determined to be 99.8% RH by water activity measurement of a saturated aqueous solution with excess solid at 25° C., indicating that it was not deliquescent.

A known amount of the title salt was dissolved in water and analyzed by UPLC. The amount of Compound 1 in the salt sample was determined to be 39.7%. This is slightly lower than the theoretical value, 45.7%. Solubility of the title salt in water was determined by UPLC to be 20 mg/mL, with a final pH of 7.

The powder X-ray diffraction pattern of the title salt is shown in FIG. 1. Thermal analysis (TGA and DSC) of the title salt is shown in FIG. 2. DMS analysis of the title salt is shown in FIG. 3.

Example 2

Preparation of Form I of (R)-8-Chloro-1-methyl-2,3,4,5-tetrahydro-1H-3-benzazepine Hemi-L-malate Salt (Compound 1 Hemi-L-malate Salt, Form I)

The title salt was prepared by the dropwise addition of L-malic acid (0.5 eq.), either in solution in hot MeOH or as a solid, to a solution of (R)-8-chloro-1-methyl-2,3,4,5-tetrahydro-1H-3-benzazepine in isopropyl acetate. The mixture was heated to ~60° C. and held at that temperature for ~1 h. The mixture was then allowed to cool to room temperature and stirred for 1-3 days. The solid product was isolated by vacuum filtration and dried on the filter or in an oven at 40° C. for. An attempt to make a 1:1 salt produced a mixture of mono-L-malate and hemi-L-malate salts.

The DRH of the title salt was measured by water activity determination for a saturated aqueous solution with excess solid to be 89.9% RH at 25° C.

A known amount of the title salt was dissolved in water and analyzed by UPLC. The amount of Compound 1 in the sample was 76.5%. This is in acceptable agreement with the theoretical amount for a hemi-L-malate salt of Compound 1, 74.5%. Aqueous solubility of the title salt was 486.3 mg/mL, final pH 6.0.

The powder X-ray diffraction pattern of the title salt is shown in FIG. 4. Thermal analysis (TGA and DSC) of the title salt is shown in FIG. 5. DMS analysis of the title salt is shown in FIG. 6.

Example 3

Preparation of Form I of (R)-8-Chloro-1-methyl-2,3,4,5-tetrahydro-1H-3-benzazepine L-Glutamate Salt (Compound 1 L-Glutamate Salt, Form I)

Method 1

The title salt was prepared by addition of L-glutamic acid (0.5-1 eq.) in hot EtOH/$H_2O$ (~2:1) to a solution of (R)-8-chloro-1-methyl-2,3,4,5-tetrahydro-1H-3-benzazepine in isopropyl acetate, followed by evaporation of the solvent overnight to produce a solid. The solid was slurried in isopropyl acetate and then isolated by filtration.

Method 2

The title salt was prepared by addition of a solution of L-glutamic acid (1 eq.) in hot $H_2O$ to a solution of (R)-8-chloro-1-methyl-2,3,4,5-tetrahydro-1H-3-benzazepine. The product crystallized without the need for evaporation or the solvent.

The products of both methods produced crystalline solids with essentially the same PXRD pattern.

The DRH of the title salt was measured by water activity determination for a saturated aqueous solution with excess solid to be 98.3% RH at 25° C.

A known amount of the title salt was dissolved in water and analyzed by UPLC. The amount of Compound 1 in the sample was 59-60%. This is in acceptable agreement with calculated amount, 57.1%. Aqueous solubility of the title salt was 176.2 mg/mL, with a final pH 5.5.

The powder X-ray diffraction pattern of the title salt is shown in FIG. 7. Thermal analysis (TGA and DSC) of the title salt is shown in FIG. 8. DMS analysis of the title salt is shown in FIG. 9.

Example 4

Preparation of Form I of (R)-8-Chloro-1-methyl-2,3,4,5-tetrahydro-1H-3-benzazepine L-Aspartate Salt (Compound 1 L-Aspartate Salt, Form I)

The title salt was prepared by addition of a solution of (R)-8-chloro-1-methyl-2,3,4,5-tetrahydro-1H-3-benzazepine in either acetone or acetonitrile to one equivalent of aspartic acid solid. The mixture was heated to 50° C. then slow-cooled and stirred overnight.

A known amount of the title salt was dissolved in water and analyzed by UPLC. The amount of Compound 1 in the sample was 59.5%. This is in good agreement with the theoretical value, 61.7%. Aqueous solubility of the title salt was 42 mg/mL. The final pH of a near saturated solution of this salt was 4.82.

The powder X-ray diffraction pattern of the title salt is shown in FIG. 10. Thermal analysis (TGA and DSC) of the title salt is shown in FIG. 11. DMS analysis of the title salt is shown in FIG. 12.

Example 5

Preparation of Form I of (R)-8-Chloro-1-methyl-2,3,4,5-tetrahydro-1H-3-benzazepine Hemimucate (Compound 1 Hemimucate Salt, Form I)

The title compound was synthesized from (R)-8-chloro-1-methyl-2,3,4,5-tetrahydro-1H-3-benzazepine (2 equivalents) and mucic acid (1 equivalent) in THF, acetone or IPA (~10 mg/mL) with 4% water.

A known amount of Compound 1 hemimucate salt, was dissolved in methanol and analyzed by UPLC. The percent of Compound 1 in the salt sample was determined to be 64.4%. This is close to the theoretical percent Compound 1 in a 1:0.5 Compound 1 hemimucate salt (65.1%).

The aqueous solubility of Compound 1 hemimucate was determined to be 0.85 mg/mL at a pH of 1.48.

The powder X-ray diffraction pattern of the title salt is shown in FIG. 13. Thermal analysis (TGA and DSC) of the title salt is shown in FIG. 13. DMS analysis of the title salt is shown in FIG. 15.

Example 6

Preparation of Form I of (R)-8-Chloro-1-methyl-2,3,4,5-tetrahydro-1H-3-benzazepine Glucuronate Salt (Compound 1 Glucuronate Salt, Form I)

The title salt was prepared by addition of a molar equivalent of D-glucuronic acid to a solution of (R)-8-chloro-1-methyl-2,3,4,5-tetrahydro-1H-3-benzazepine in isopropanol, acetonitrile, ethyl acetate, or acetone at 60° C. D-glucuronic acid, dissolved in the corresponding solvent at 60° C., was added dropwise with vigorous stirring. Precipitation occurred immediately and the suspension was allowed to cool and stir overnight. The resulting solid was recovered by filtration and dried in a fume hood overnight.

A known amount of Compound 1 glucuronate salt was dissolved in methanol and analyzed by UPLC. The percentage of Compound 1 in the salt sample was determined to be 56.9%. This is slightly higher than the theoretical percentage of Compound 1 in an anhydrous Compound 1 glucuronate salt (50.2%).

The solubility of Compound 1 glucuronate in water was determined by UPLC to be 2.5 mg/mL, with a final pH of 6.80.

The powder X-ray diffraction pattern of the title salt is shown in FIG. 16. Thermal analysis (TGA and DSC) of the title salt is shown in FIG. 17. DMS analysis of the title salt is shown in FIG. 18.

Example 7

Preparation of Form I of (R)-8-Chloro-1-methyl-2,3,4,5-tetrahydro-1H-3-benzazepine Pyroglutamate Salt (Compound 1 Pyroglutamate Salt, Form I)

The title salt was prepared by combining one equivalent of pyroglutamic acid with (R)-8-chloro-1-methyl-2,3,4,5-tetrahydro-1H-3-benzazepine in ethyl acetate at 60° C. then cooling slowly and stirring overnight. The resulting white solid was isolated by filtration and dried.

A known amount of Compound 1 pyroglutamate was dissolved in methanol and analyzed by UPLC. The percentage of Compound 1 in the salt sample was determined to be 61.1%. This is close to the theoretical percentage of Compound 1 in a 1:1 Compound 1 pyroglutamate salt, (60.3%).

The aqueous solubility of Compound 1 pyroglutamate was determined to be >161.5 mg/mL at pH 3.94.

The powder X-ray diffraction pattern of the title salt is shown in FIG. 19. Thermal analysis (TGA and DSC) of the title salt is shown in FIG. 20. DMS analysis of the title salt is shown in FIG. 21.

Example 8

Preparation of Form I of (R)-8-Chloro-1-methyl-2,3,4,5-tetrahydro-1H-3-benzazepine Di-camphorate Salt Solvate (Compound 1 Di-camphorate Salt Solvate, Form I)

The title salt was prepared by combining equal molar amounts of (R)-8-chloro-1-methyl-2,3,4,5-tetrahydro-1H-3-benzazepine and (1R,3S)-(+)-camphoric acid in ethyl acetate with 4% water. The solution was heated to 50° C. then slowly cooled. Upon cooling the sample was a clear solution and did not change after addition of MTBE. The sample was evaporated to a clear oil which formed a white solid after standing at room temperature.

A known amount of Compound 1 di-camphorate salt (solvated) was dissolved in methanol and analyzed by UPLC. Percent of Compound 1 in the salt sample was determined to be 28.9%. This is close to the theoretical percent Compound 1 in a Compound 1 di-camphorate hydrate, 31.9%.

The aqueous solubility of Compound 1 di-camphorate salt solvate was determined to be 38.6 mg/mL (12.3 mg/mL of the free base) at a pH of 5.2.

The powder X-ray diffraction pattern of the title salt is shown in FIG. 22. Thermal analysis (TGA and DSC) of the title salt is shown in FIG. 23. DMS analysis of the title salt is shown in FIG. 24.

Example 9

Preparation of (R)-8-Chloro-1-methyl-2,3,4,5-tetrahydro-1H-3-benzazepine Hydrochloride Salt Hemihydrate, Form III

Step A: Preparation of 8-Chloro-1-methyl-2,3,4,5-tetrahydro-1H-3-benzazepine.

To a reactor equipped with overhead agitation, jacket temperature control, a nitrogen inlet, and a caustic scrubber vent were charged, in the specified order, 2-chloro-N-(4-chlorophenethyl)propan-1-amine hydrochloride (1.00 kg, 3.72 mol), aluminum chloride (0.745 kg, 5.58 mol), and 1,2-dichlorobenzene (2.88 kg). The stirred reactor contents were heated to 125-130° C., and stirring was continued at that temperature for 14-18 h. At 60-70° C., a dark colored solution was obtained. After reaction completion (<1.0% starting material by HPLC peak area) had been verified, the stirred reactor contents were cooled to 30-35° C. To a second reactor vented to a caustic scrubber was charged purified water (1.60 L) and silica gel (0.160 kg). The Friedel-Crafts reaction mixture was transferred from the first reactor to the second reactor sufficiently slowly to maintain the stirred contents of the second reactor at <60° C. After the transfer is completed, the next step may be executed without any hold period. The silica gel was filtered on a medium to coarse filter element at 55-60° C., and the filtered solids were subsequently washed with purified water (800 mL) preheated to 50-60° C. The combined mother and wash liquor filtrates were cooled to 20-25° C. with vigorous agitation. Then the stirring was stopped, and the phases were allowed to separate at 20-25° C. (Process volume peaked at this point at 5.68 L). Three phases separated after 1-2 hours of standing. The lowest layer was drained to waste disposal. This dark layer consisted mostly of 1,2-dichlorobenzene (1.64 kg, 1.33 L) at pH 3-4. About 1% of the product was lost to this layer. The remaining two phases were allowed to stand without agitation for another 2-4 h. The lower layer was drained and saved (Layer A). This light colored phase (2.64 kg, 2.00 L, pH 2-3) contained ~90% 8-chloro-1-methyl-2,3,4,5-tetrahydro-1H-benzazepine. The upper layer (2.24 kg of a turbid water phase at pH 0-1) contains ~1-4% 8-chloro-1-methyl-2,3,4,5-tetrahydro-1H-benzazepine and remained in the reactor for back-extraction. The reactor was charged with cyclohexane (1.10 kg) and then 30% aqueous NaOH (2.44 kg, 18.3 mol). The resulting mixture (5.60 L) was stirred vigorously for 30 min at room temperature. The stirring was stopped, and the phases were allowed to separate for 25-40 min. If the pH of the lower (aqueous) phase was ≥13, it was drained to waste disposal. Otherwise, more 30% aqueous NaOH was added, and this extraction was repeated. At pH 14, the aqueous phase contains <0.1% 8-chloro-1-methyl-2,3,4,5-tetrahydro-1H-benzazepine free base. The remaining upper (organic) phase from the reactor was drained and saved (Layer B). The reactor was rinsed with purified water and followed by a suitable organic solvent to remove residual salts. The lower, light-colored product phase (the middle of the original three phases, Layer A) and the upper phase (organic, Layer B) were returned to the reactor. To the stirred reactor contents was added 30% aqueous NaOH (1.60 kg, 12.0 mol). The reactor contents were stirred vigorously for 0.5 hours. The stirring was discontinued and the phases were allowed to separate over 15-30 minutes. The lower (aqueous) layer was drained to waste disposal. To the upper (organic) phase remaining in the reactor was added purified water (2.40 kg). The reactor contents were stirred vigorously at 60-65° C. for 0.5 h. The stirring was discontinued, and the phases were allowed to separate at 60-65° C. over 1.5-2 h. The lower (aqueous) layer was drained to waste disposal. With a reactor jacket temperature of 55-60° C., solvent from the upper (organic) layer was removed by vacuum distillation at pressures starting at 115-152 torr and falling to 40 torr. The crude product, 8-chloro-1-methyl-2,3,4,5-tetrahydro-1H-benzazepine as the free base, was obtained as a yellow to brown oil distillation residue.

Step B: Preparation of (R)-8-Chloro-1-methyl-2,3,4,5-tetrahydro-1H-3-benzazepine Hemitartrate Salt.

The distillation residue from Step A (crude 8-chloro-1-methyl-2,3,4,5-tetrahydro-1H-benzazepine as the free base) was dissolved in acetone (0.400 kg). The resulting solution was drained and weighed to assay the 8-chloro-1-methyl-2,3,4,5-tetrahydro-1H-benzazepine content by HPLC. Results of the assay were used to calculate charges of acetone, L-tartaric acid, and water. The quantities indicated below are typical for achievement of the target 8-chloro-1-methyl-2,3,4,5-tetrahydro-1H-benzazepine:acetone:L-tartaric acid:water mole ratio of 1.00:9.6:0.25:3.6 prior to addition of seed crystals. More acetone (1.415 kg) was added to the reactor and the stirred reactor contents were heated to 47-52° C. To the resulting solution was added a solution of L-tartaric acid (0.1223 kg, 0.815 mol) in purified water (0.211 kg) at a steady rate over 5-15 min. A thin suspension formed during the addition but then redissolved when the mixture temperature was reestablished at 50° C. Hemitartrate seed crystals (0.80 g) were added to the 50° C. solution to achieve cloudiness and to initiate nucleation. Nucleation was allowed to continue for 2-3 h with agitation at 47-52° C. Acetone (0.473 kg) was added to the reactor while the stirred reactor contents were maintained at 50° C. The resulting suspension was cooled to 0-5° C. slowly over 3-5 h. Stirring was continued at 0° C. for another 1-3 h. The resulting white precipitate was collected on a medium-to-fine filter element and then washed with a mixture of acetone (0.900 kg) and purified water (0.054 kg). The enantiomeric excess (ee) of the wet cake was determined.

If the ee was <98%, the wet cake was transferred back into the reactor and reslurried in a mixture of acetone (1.90 kg) and purified water (0.400 kg) at 55-60° C. for 0.5-1 h. If dissolution had not been achieved after one h, then water (approximately 0.160 kg) was added until a clear solution was achieved. The resulting mixture was then cooled to 0-5° C. slowly over 2-3 h. Stirring at 0° C. was continued for another 3-5 h. The resulting white precipitate was collected on a medium-to-fine filter element and then washed with acetone (0.400 kg) at 0-4° C.

The washed solid product (296 g wet) was dried at 60-65° C. under full vacuum for 15-20 hours. The yield of (R)-8-chloro-1-methyl-2,3,4,5-tetrahydro-1H-3-benzazepine hemitartrate salt, with about 99.7% ee and 7.5 wt. % water content, was 295 g (27.1% based on racemic 2-chloro-N-(4-chlorophenethyl)propan-1-amine hydrochloride and corrected for product water content).

Step C: Preparation of (R)-8-Chloro-1-methyl-2,3,4,5-tetrahydro-1H-3-benzazepine Hydrochloride Salt Hemihydrate, Form III.

To a reactor equipped with overhead agitation and a nitrogen inlet was charged, in the specified order, (R)-8-chloro-1-methyl-2,3,4,5-tetrahydro-1H-3-benzazepine hemitartrate (1.00 kg containing 7.5 wt % water, 1.71 mol), potassium carbonate (0.508 kg, 3.68 moles), ethyl acetate (2.68 kg), and purified water (2.68 kg). The resulting mixture was stirred at 20-25° C. for 30-40 min, and then the phases were allowed to separate over 0.5-1 h. The lower (aqueous) phase was drained to waste disposal. Purified water (2.68 kg) was added to the reactor, and the resulting mixture was vigorously stirred for 10-20 min. The phases were allowed to separate over 1-1.5 h. The lower (aqueous) phase was drained to waste disposal. With the reactor contents at a temperature of 40-45° C., the solvent was removed by vacuum distillation at pressures falling from 153 torr to 46 torr. The residue was cooled to 20-25° C. Ethyl acetate (3.81 kg) was charged to the reactor, and the distillation residue was dissolved with stirring. The water content of the resulting solution was verified by Karl Fischer analysis to be <0.8 wt. %. The solution was filtered through a polishing filter. The reactor was rinsed through the filter with ethyl acetate (2.33 kg) previously verified by Karl Fischer analysis to have <0.05 wt. % water content. Both the solution and rinse filtrates were charged back into the reactor. Purified water (39.9 g) was added to the reactor. The stirred reactor contents were cooled to 0-5° C., and then HCl gas (19.0 g, 0.521 mol) was added while the stirred reactor contents were maintained at 0-5° C. (R)-8-Chloro-1-methyl-2,3,4,5-tetrahydro-1H-3-benzazepine hydrochloride salt hemihydrate seed crystals (1.33 g) were added to the stirred reactor contents to initiate nucleation at 0-5° C. The remaining HCl gas (107.6 g, 2.95 mol) was charged to the reactor at a steady rate over at least 1.5-2 h while the stirred reactor contents were maintained at 0-5° C. The resulting suspension was stirred at 0-5° C. for 2 h. The resulting white precipitate was collected on a medium-to-fine filter element. The reactor and then the filtered solid product were washed with ethyl acetate (1.33 kg). The wet cake (ca. 867 g) was dried at full vacuum and 33-37° C. for 20 h or until the cake temperature had been stable for 4 hours, whichever occurred first. The resulting (R)-8-chloro-1-methyl-2,3,4,5-tetrahydro-1H-3-benzazepine hydrochloride salt hemihydrate (3.7 wt. % water content, 14.7% chloride content, <0.01% ROI, >99.6% ee, >99% HPLC purity, and <0.1% wrong isomer content) was obtained in a yield of about 741 g (89.9%).

Those skilled in the art will recognize that various modifications, additions, substitutions, and variations to the illustrative examples set forth herein can be made without departing from the spirit of the invention and are, therefore, considered within the scope of the invention.

The invention claimed is:

1. A salt selected from:
   (R)-8-chloro-1-methyl-2,3,4,5-tetrahydro-1H-3-benzazepine (1 S)-(+)-10-camsylate salt;
   (R)-8-chloro-1-methyl-2,3,4,5-tetrahydro-1H-3-benzazepine hemi-L-malate salt;
   (R)-8-chloro-1-methyl-2,3,4,5-tetrahydro-1H-3-benzazepine L-glutamate salt;
   (R)-8-chloro-1-methyl-2,3,4,5-tetrahydro-1H-3-benzazepine L-aspartate salt;
   (R)-8-chloro-1-methyl-2,3,4,5-tetrahydro-1H-3-benzazepine hemimucate salt;
   (R)-8-chloro-1-methyl-2,3,4,5-tetrahydro-1H-3-benzazepine pyroglutamate salt; and
   (R)-8-chloro-1-methyl-2,3,4,5-tetrahydro-1H-3-benzazepine glucuronate salt;
   and pharmaceutically acceptable solvates and hydrates thereof.

2. The salt according to claim 1, that is (R)-8-chloro-1-methyl-2,3,4,5-tetrahydro-1H-3-benzazepine (1S)-(+)-10-camsylate salt.

3. The salt according to claim 2, having an X-ray powder diffraction pattern comprising peaks, in terms of 2θ, at about 18.25°, about 16.45°, and about 18.57°.

4. The salt according to claim 2, having an X-ray powder diffraction pattern substantially as shown in FIG. 1.

5. The salt according to claim 1, that is (R)-8-chloro-1-methyl-2,3,4,5-tetrahydro-1H-3-benzazepine hemi-L-malate salt.

6. The salt according to claim 5, having an X-ray powder diffraction pattern comprising peaks, in terms of 2θ, at about 10.84°, about 11.7932°, and about 21.97°.

7. The salt according to claim 5, having an X-ray powder diffraction pattern substantially as shown in FIG. 4.

8. The salt according to claim 1, that is (R)-8-chloro-1-methyl-2,3,4,5-tetrahydro-1H-3-benzazepine L-glutamate salt.

9. The salt according to claim 8, having an X-ray powder diffraction pattern comprising peaks, in terms of 2θ, at about 25.59°, about 17.63°, and about 21.78°.

10. The salt according to claim 8, having an X-ray powder diffraction pattern substantially as shown in FIG. 7.

11. The salt according to claim 1, that is (R)-8-chloro-1-methyl-2,3,4,5-tetrahydro-1H-3-benzazepine L-aspartate salt.

12. The salt according to claim 11, having an X-ray powder diffraction pattern comprising peaks, in terms of 2θ, at about 21.22°, about 8.49°, and about 13.40°.

13. The salt according to claim 11, having an X-ray powder diffraction pattern substantially as shown in FIG. 10.

14. The salt according to claim 1, that is (R)-8-chloro-1-methyl-2,3,4,5-tetrahydro-1H-3-benzazepine hemimucate salt.

15. The salt according to claim 14, having an X-ray powder diffraction pattern comprising a peak, in terms of 2θ, at about 5.06°, about 18.60°, and about 20.92°.

16. The salt according to claim 14, having an X-ray powder diffraction pattern substantially as shown in FIG. 13.

17. The salt according to claim 1, that is (R)-8-chloro-1-methyl-2,3,4,5-tetrahydro-1H-3-benzazepine glucuronate salt.

18. The salt according to claim 17, having an X-ray powder diffraction pattern comprising peaks, in terms of 2θ, at about 16.46°, about 5.59°, and about 18.40°.

19. The salt according to claim 17, having an X-ray powder diffraction pattern substantially as shown in FIG. 16.

20. The salt according to claim 1, that is (R)-8-chloro-1-methyl-2,3,4,5-tetrahydro-1H-3-benzazepine pyroglutamate salt.

21. The salt according to claim 20, having an X-ray powder diffraction pattern comprising peaks, in terms of 2θ, at about 6.78°, about 18.80°, and about 16.95°.

22. The salt according to claim 20, having an X-ray powder diffraction pattern substantially as shown in FIG. 19.

23. A pharmaceutical composition comprising a salt according to claim 1 and a pharmaceutically acceptable carrier.

24. A process for preparing a pharmaceutical composition comprising admixing a salt according to claim 1 and a pharmaceutically acceptable carrier.

* * * * *